US012799403B2

(12) United States Patent
Urayama et al.

(10) Patent No.: US 12,799,403 B2
(45) Date of Patent: Nov. 17, 2026

(54) METHOD FOR CONVERTING ETHANOL AND METHODS FOR PRODUCING OTHER HYDROCARBONS

(71) Applicant: ASAHI KASEI KABUSHIKI KAISHA, Tokyo (JP)

(72) Inventors: Teppei Urayama, Tokyo (JP); Ryusuke Miyazaki, Tokyo (JP); Takashi Tsunoda, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 219 days.

(21) Appl. No.: 18/728,322

(22) PCT Filed: Jan. 30, 2023

(86) PCT No.: PCT/JP2023/002899
§ 371 (c)(1),
(2) Date: Jul. 11, 2024

(87) PCT Pub. No.: WO2023/145941
PCT Pub. Date: Aug. 3, 2023

(65) Prior Publication Data

US 2026/0167872 A1 Jun. 18, 2026

(30) Foreign Application Priority Data

Jan. 31, 2022 (JP) ................................ 2022-012969
May 31, 2022 (JP) ................................ 2022-088596
Aug. 30, 2022 (JP) ................................ 2022-137041

(51) Int. Cl.
*C10G 3/00* (2006.01)
*C07C 2/86* (2006.01)
(Continued)

(52) U.S. Cl.
CPC ............... *C10G 3/49* (2013.01); *C10G 55/06* (2013.01); *C07C 2/862* (2013.01); *C07C 2/864* (2013.01);
(Continued)

(58) Field of Classification Search
CPC .. C10G 3/49; C10G 55/06; C10G 2300/1003; C10G 2300/1088; C10G 2300/4006;
(Continued)

(56) References Cited

U.S. PATENT DOCUMENTS 4,232,179 A * 11/1980 Valladares Barrocas .................... C07C 1/24 585/639
4,698,452 A 10/1987 Le Van Mao et al.
(Continued)

FOREIGN PATENT DOCUMENTS

CN 101239870 A 8/2008
CN 101659592 A 3/2010
(Continued)

OTHER PUBLICATIONS

International Preliminary Report on Patentability, dated Aug. 6, 2024, and Written Opinion of the International Searching Authority, dated Apr. 4, 2023, for International Application No. PCT/JP2023/002899, with English translation.
(Continued)

*Primary Examiner* — Ali Z Fadhel
(74) *Attorney, Agent, or Firm* — Birch, Stewart, Kolasch & Birch, LLP

(57) ABSTRACT

Provided are (1) a method for converting ethanol, comprising contacting a raw material mixture containing ethylene and ethanol with a catalyst in an adiabatic reactor to obtain a reaction gas containing an olefin having 3 or more carbon atoms, (2) a method for converting ethanol, comprising
(Continued)

contacting a raw material mixture containing methanol and ethanol with a catalyst in an adiabatic reactor to obtain a reaction gas containing an olefin having 3 or more carbon atoms, and (3) a method for converting ethanol, comprising: contacting a raw material mixture containing ethanol and ethylene with a catalyst in an adiabatic reactor to obtain a reaction gas containing an olefin having 3 or more carbon atoms; separating the reaction gas into fraction A mainly containing a hydrocarbon having 2 to 3 carbon atoms and fraction B mainly containing a hydrocarbon having 4 to 6 carbon atoms by a first distillation column; and recycling at least a portion of the fraction A as a portion of the raw material mixture to the reaction step.

19 Claims, 5 Drawing Sheets

(51) Int. Cl.
*C07C 6/02* (2006.01)
*C07C 6/04* (2006.01)
*C10G 55/06* (2006.01)

(52) U.S. Cl.
CPC .................. *C07C 6/02* (2013.01); *C07C 6/04* (2013.01); *C10G 2300/1003* (2013.01); *C10G 2300/1088* (2013.01); *C10G 2300/4006* (2013.01); *C10G 2300/4081* (2013.01); *C10G 2400/30* (2013.01)

(58) Field of Classification Search
CPC ........ C10G 2300/4081; C10G 2400/30; C07C 2/862; C07C 2/864; C07C 6/02; C07C 6/04
See application file for complete search history.

(56) References Cited

U.S. PATENT DOCUMENTS

| | | | |
|---|---|---|---|
| 2006/0229482 | A1 | 10/2006 | Setoyama et al. |
| 2007/0027351 | A1 | 2/2007 | Dath et al. |
| 2007/0265482 | A1 | 11/2007 | Tsunoda et al. |
| 2009/0082605 | A1 | 3/2009 | Bailey et al. |
| 2010/0022810 | A1 | 1/2010 | Sekiguchi et al. |
| 2010/0069691 | A1 | 3/2010 | Morschbacker |
| 2010/0145125 | A1 | 6/2010 | Xie et al. |
| 2010/0197986 | A1 * | 8/2010 | Midorikawa ........ B01J 37/0036 502/64 |
| 2010/0204532 | A1 | 8/2010 | Minoura et al. |
| 2011/0098518 | A1 | 4/2011 | Minoux et al. |
| 2011/0137096 | A1 | 6/2011 | Minoux et al. |
| 2011/0288358 | A1 | 11/2011 | Buchold et al. |
| 2013/0245290 | A1 | 9/2013 | Vijayakumari et al. |
| 2014/0018593 | A1 | 1/2014 | Birke et al. |
| 2015/0152024 | A1 | 6/2015 | Iitsuka et al. |
| 2016/0199824 | A1 | 7/2016 | Yoshida et al. |
| 2016/0310934 | A1 | 10/2016 | Braunsmann et al. |
| 2020/0316574 | A1 | 10/2020 | Casci et al. |

FOREIGN PATENT DOCUMENTS

| | | | |
|---|---|---|---|
| CN | 101939276 | A | 1/2011 |
| CN | 103012031 | A | 4/2013 |
| CN | 110560155 | A | 12/2019 |
| CN | 110871107 | A | 3/2020 |
| EP | 0 123 449 | A | 10/1984 |
| JP | 54-36203 | A | 3/1979 |
| JP | 58-146515 | A | 9/1983 |
| JP | 59-19927 | A | 2/1984 |
| JP | 59-199639 | A | 11/1984 |
| JP | 60-132650 | A | 7/1985 |
| JP | 3-123739 | A | 5/1991 |
| JP | 2007-29107 | A | 2/2007 |
| JP | 2007-502796 | A | 2/2007 |
| JP | 2007-290991 | A | 11/2007 |
| JP | 2007-291076 | A | 11/2007 |
| JP | 2007-302652 | A | 11/2007 |
| JP | 2008-74764 | A | 4/2008 |
| JP | 2008-81417 | A | 4/2008 |
| JP | 2008-106056 | A | 5/2008 |
| JP | 2010-511634 | A | 4/2010 |
| JP | 2011-511037 | A | 4/2011 |
| JP | 2014-46273 | A | 3/2014 |
| JP | 2014-47176 | A | 3/2014 |
| JP | 2014-65674 | A | 4/2014 |
| JP | 2015-189720 | A | 11/2015 |
| JP | 2015-189766 | A | 11/2015 |
| JP | 2015-224249 | A | 12/2015 |
| JP | 2017-507773 | A | 3/2017 |
| JP | 2022-523138 | A | 4/2022 |
| TW | 200724521 | A | 7/2007 |
| WO | WO 2005/056504 | A1 | 6/2005 |
| WO | WO 2006/009099 | A1 | 1/2006 |
| WO | WO 2007/080957 | A1 | 7/2007 |
| WO | WO 2007/114195 | A1 | 10/2007 |
| WO | WO 2008/111480 | A1 | 9/2008 |
| WO | WO 2009/031445 | A1 | 3/2009 |
| WO | WO 2009/037992 | A1 | 3/2009 |
| WO | WO 2012/005864 | A1 | 1/2012 |
| WO | WO 2014/025021 | A1 | 2/2014 |
| WO | WO 2015/029355 | A1 | 3/2015 |
| WO | WO 2021/006245 | A1 | 1/2021 |

OTHER PUBLICATIONS

International Search Report for International Application No. PCT/JP2023/002899, dated Apr. 4, 2023, with English translation.
Baba et al., "Selective synthesis of propylene from ethylene or ethanol using SAP O-34 as a catalyst," Special Edition, vol. 37, No. 4, 2008, pp. 66-74 (17 pages total), with an English translation.
Takahashi et al., "H-ZSM-5 catalyzed synthesis of propylene from ethanol and ethylene," SCEJ 41st Autumn Meeting, Higashi-Hiroshima, 2009, p. 584 (2 pages total), with an English translation.
Takahashi et al., "Zeolite Catalyzed Propylene Conversion Reaction from Ethanol," SCEJ 40th Autumn Meeting, Sendai, 2008, 2 pages total, with an English translation.
Takahashi et al., "Zeolite Catalyzed Synthesis of Lower Olefins from Bioethanol," Solid Catalyst Group, Technical Research Department of Environmental Chemistry, vol. 27, No. 4, 2010, pp. 145-152 (16 pages total), with an English translation.
European Search Report for European Application No. 23747151.1, dated Jan. 19, 2026.
Machine translation of JP-58-146515-A, published on Sep. 1, 1983.

* cited by examiner

[Figure 1]
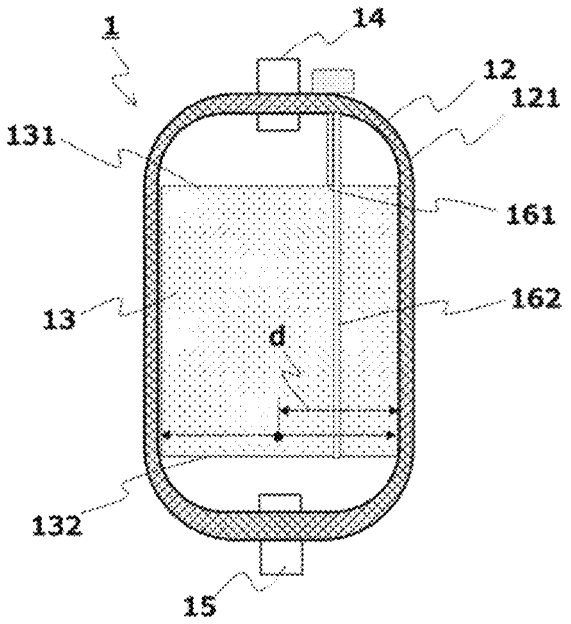
[Figure 2]
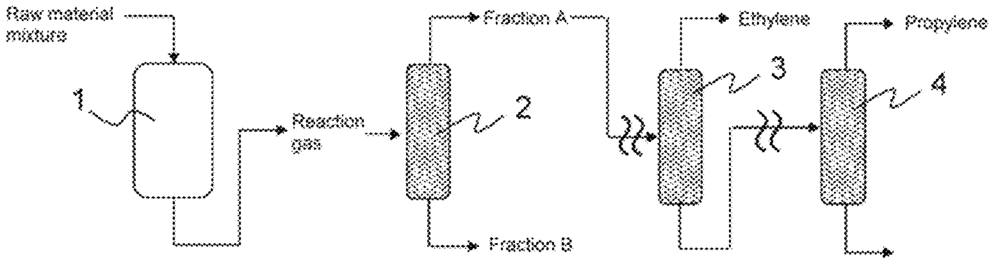
[Figure 3]
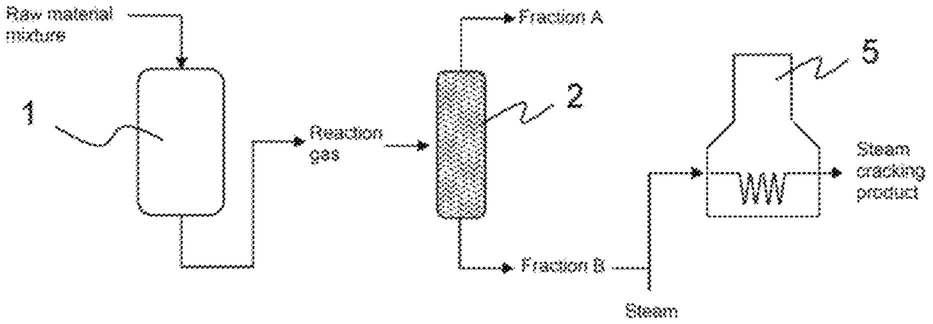

[Figure 4]
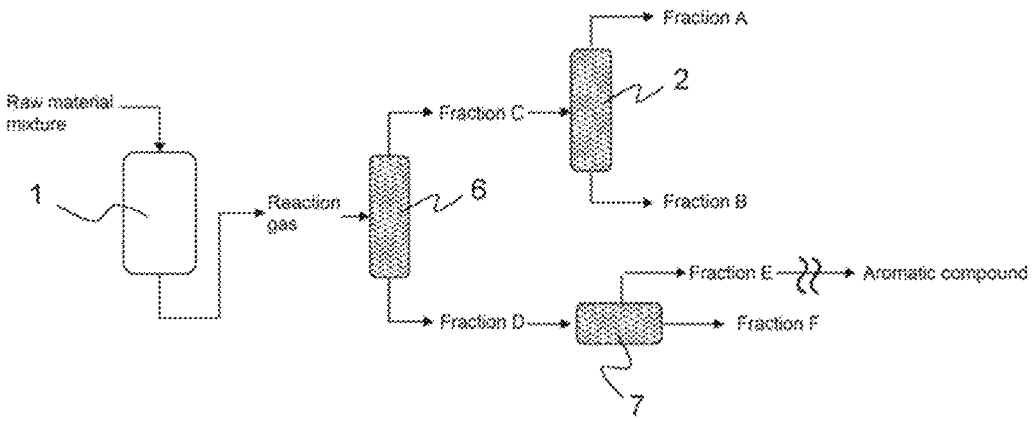
[Figure 5]
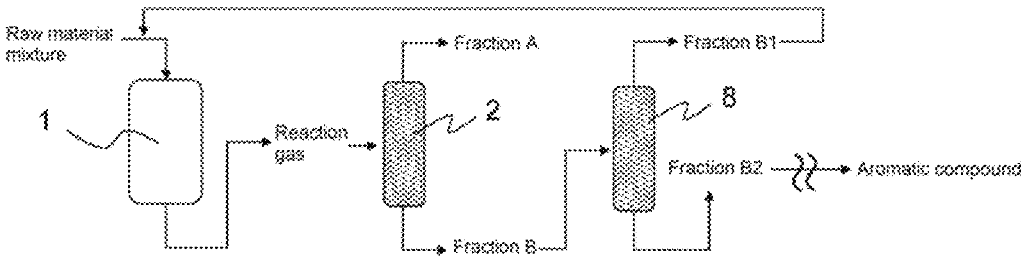
[Figure 6]
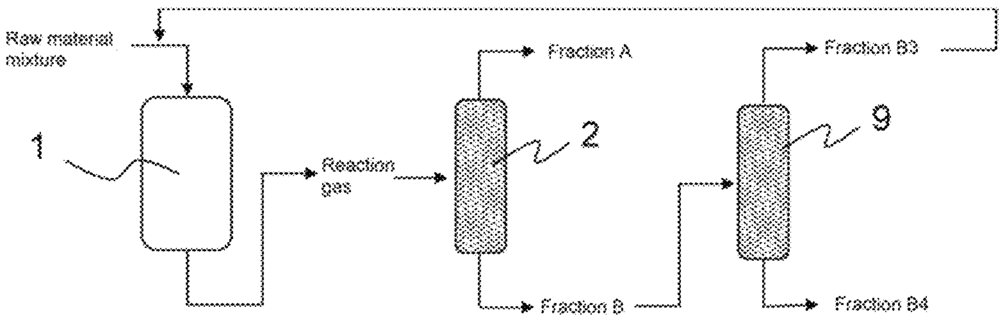

[Figure 7]
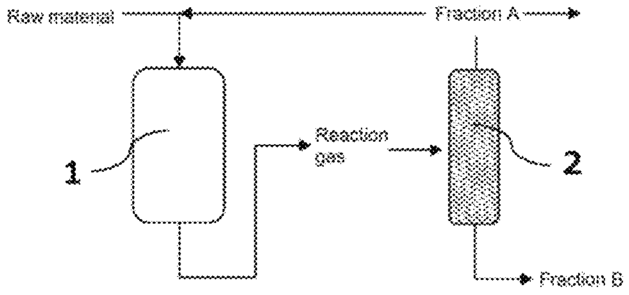
[Figure 8]
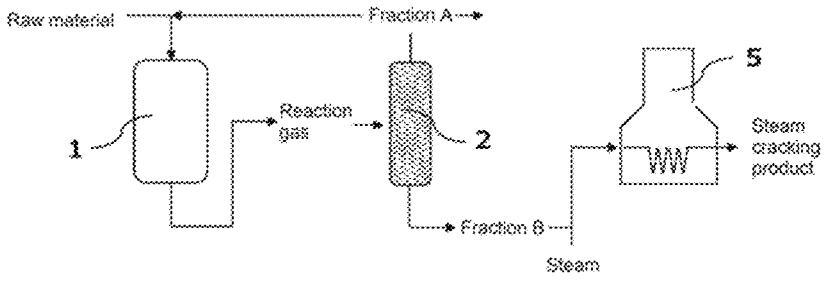
[Figure 9]
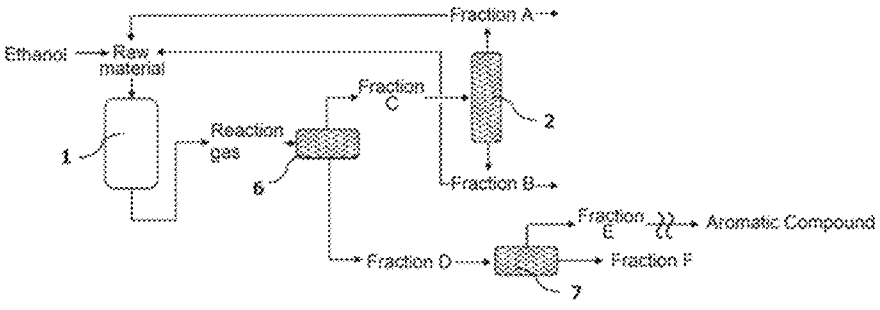

[Figure 10]
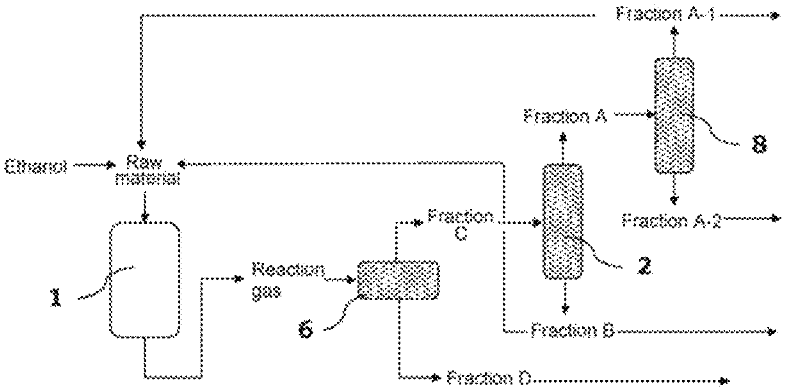
[Figure 11]
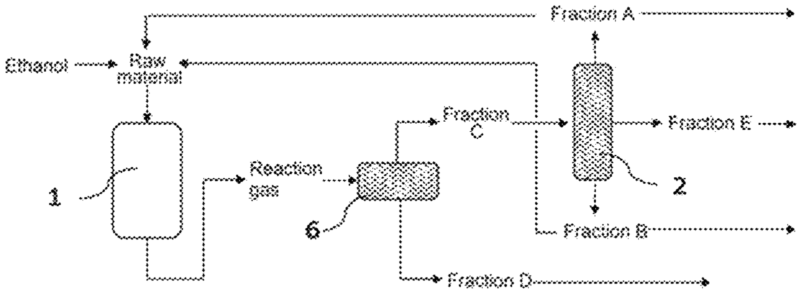
[Figure 12]
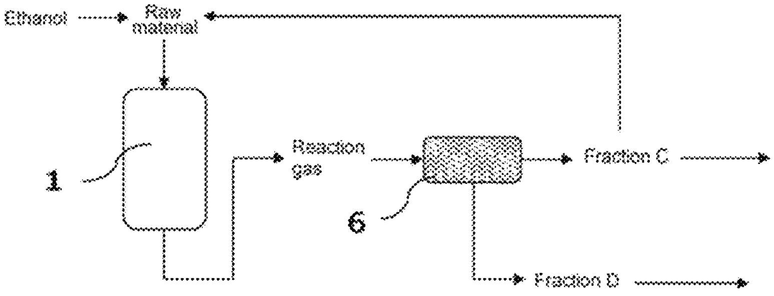

[Figure 13]
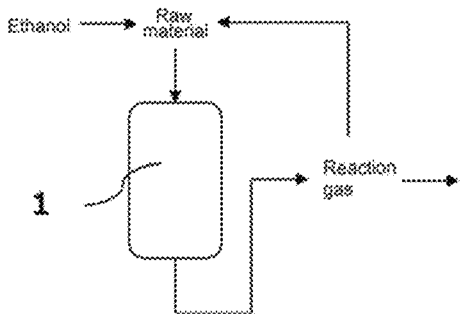

METHOD FOR CONVERTING ETHANOL AND METHODS FOR PRODUCING OTHER HYDROCARBONS

TECHNICAL FIELD

The present invention relates to a method for converting ethanol and other methods for producing hydrocarbons.

BACKGROUND ART

Hydrocarbons such as lower olefins are core raw materials important for chemical industry. Particularly, various methods for producing propylene have been actively developed or modified in anticipation of growing demand therefor. Among them, a method including contacting naphtha or olefins with a catalyst containing zeolite as an active species is known as a general process for producing propylene.

For example, Patent Literature 1 discloses a method for producing propylene from an ethylene as a raw material. Patent Literatures 2 and 3 disclose techniques of converting ethanol to propylene with pentasil zeolite and zeolite-supported zinc cerium oxide, respectively. For example, Patent Literature 4 discloses a method for producing a lower olefin by processing an oxygenate and an olefin having 4 or more carbon atoms as raw materials. Patent Literature 5 discloses a method for producing a lower olefin by converting a lower alcohol and naphtha as raw materials. For example, Patent Literature 6 discloses a method for producing propylene from a raw material containing methanol.

CITATION LIST

Patent Literature

Patent Literature 1: WO2014/025021A1
Patent Literature 2: WO2015/029355A1
Patent Literature 3: CN110560155A
Patent Literature 4: US2014/0018593A1
Patent Literature 5: CN110871107A
Patent Literature 6: WO2005/56504A1

SUMMARY OF INVENTION

The present invention encompasses the following embodiments.

[1]

A method for converting ethanol, comprising:

contacting a raw material mixture containing ethylene and ethanol with a catalyst in an adiabatic reactor to obtain a reaction gas containing an olefin having 3 or more carbon atoms.

[2]

The method for converting ethanol according to [1], wherein a molar ratio of ethylene/ethanol in the raw material mixture is 0.20 to 2.5.

[3]

The method for converting ethanol according to [1] or [2], wherein a molar ratio of ethylene/ethanol in the raw material mixture is 0.20 to 2.0.

[4]

The method for converting ethanol according to any of [1] to [3], further comprising:

separating ethylene and propylene from the reaction gas.

[5]

The method for converting ethanol according to any of [1] to [4], wherein the raw material mixture contains an olefin having 4 to 6 carbon atoms.

[6]

The method for converting ethanol according to [5], wherein a molar ratio of olefin having 4 to 6 carbon atoms/ethylene in the raw material mixture is 3.0 or less.

[7]

A method for converting ethanol, comprising:

contacting a raw material mixture containing methanol and ethanol with a catalyst in an adiabatic reactor to obtain a reaction gas containing an olefin having 3 or more carbon atoms.

[8]

The method for converting ethanol according to any of [1] to [6], wherein the raw material mixture comprises methanol.

[9]

The method for converting ethanol according to [7] or [8], wherein a molar ratio of methanol/ethanol in the raw material mixture is 0.050 to 2.0.

[10]

The method for converting ethanol according to any of [7] to [9], wherein a molar ratio of methanol/ethanol in the raw material mixture is 0.20 to 1.5.

[11]

The method for converting ethanol according to any of [7] to [10], further comprising:

separating ethylene and propylene from the reaction gas.

[12]

The method for converting ethanol according to any of [7] to [11], wherein the raw material mixture contains an olefin having 4 to 6 carbon atoms.

[13]

The method for converting ethanol according to any of [7] to [12], wherein a molar ratio of olefin having 4 to 6 carbon atoms/methanol in the raw material mixture is 3.0 or less.

[14]

The method for converting ethanol according to any of [7] to [13], further comprising:

recycling at least a portion of the reaction gas or a fraction obtained by separating the reaction gas to the reactor to use it as a portion of the raw material mixture.

[15]

A method for converting ethanol, comprising:

contacting a raw material mixture containing ethanol and ethylene with a catalyst in an adiabatic reactor to obtain a reaction gas containing an olefin having 3 or more carbon atoms;

separating the reaction gas into fraction A mainly containing a hydrocarbon having 2 to 3 carbon atoms and fraction B mainly containing a hydrocarbon having 4 to 6 carbon atoms by a first distillation column; and recycling at least a portion of the fraction A as a portion of the raw material mixture to the reaction step.

[16]

The method for converting ethanol according to any of [1] to [14], further comprising:

separating the reaction gas into fraction A mainly containing a hydrocarbon having 2 to 3 carbon atoms and fraction B mainly containing a hydrocarbon having 4 to 6 carbon atoms by a first distillation column; and recycling at least a portion of the fraction A as a portion of the raw material mixture to the reaction step.

[17]

The method for converting ethanol according to [15] or [16], further comprising:

separating the fraction A into fraction A-1 mainly containing a hydrocarbon having 2 carbon atoms and fraction A-2 mainly containing a hydrocarbon having 3 carbon atoms by a second distillation column, wherein the recycling comprises recycling at least a portion of the fraction A-1 to the contacting to use it as a portion of the raw material mixture.

[18]

The method for converting ethanol according to any of [15] to [17], wherein the recycling comprises recycling at least a portion of the fraction B to the obtainment of the reaction gas to use it as a portion of the raw material mixture.

[19]

The method for converting ethanol according to any of [15] to [18], further comprising:

separating the reaction gas, by cooling, into fraction C mainly containing a hydrocarbon having 6 or less carbon atoms and fraction D mainly containing water and a hydrocarbon compound having 7 or more carbon atoms.

[20]

The method for converting ethanol according to any of [15] to [19], wherein the separating by the first distillation column comprises obtaining an intermediately discharged outflow by preparing a side-cut stage in the first distillation column.

[21]

The method for converting ethanol according to any of [1] to [20], further comprising:

separating the reaction gas into fraction A mainly containing a hydrocarbon having 1 to 3 carbon atoms and fraction B mainly containing a hydrocarbon having 4 to 8 carbon atoms; and separating ethylene and propylene from the fraction A.

[22]

The method for converting ethanol according to [21], further comprising recycling at least a portion of the fraction B to the reactor to use it as a portion of the raw material mixture.

[23]

The method for converting ethanol according to [21] or [22], further comprising:

separating the fraction B into fraction B1 mainly containing an aliphatic hydrocarbon having 4 to 6 carbon atoms and fraction B2 mainly containing an aromatic compound; and recycling at least a portion of the fraction B1 to the reactor to use it as a portion of the raw material mixture.

[24]

The method for converting ethanol according to any of [21] to [23], further comprising:

subjecting the fraction B to steam cracking to obtain a steam cracking product containing ethylene and propylene; and separating ethylene and propylene from the steam cracking product.

[25]

The method for converting ethanol according to any of [1] to [24], wherein the reactor is a fixed-bed adiabatic reactor.

[26]

The method for converting ethanol according to any of [1] to [25], wherein the reactor is a fixed-bed single-stage adiabatic reactor.

[27]

The method for converting ethanol according to any of [1] to [26], further comprising combusting coke deposited on the catalyst.

[28]

The method for converting ethanol according to any of [1] to [27], wherein a catalyst bed outlet temperature is 450 °C to 590 °C.

[29]

The method for converting ethanol according to any of [1] to [28], wherein a catalyst bed inlet temperature is 450 °C to 590 °C.

[30]

The method for converting ethanol according to any of [1] to [29], wherein a temperature difference between a catalyst bed outlet temperature and a catalyst bed inlet temperature is −80 K to 80 K.

[31]

The method for converting ethanol according to any of [1] to [30], wherein the catalyst is a zeolite-containing catalyst.

[32]

The method for converting ethanol according to [31], wherein the zeolite-containing catalyst comprises medium pore-size zeolite.

[33]

The method for converting ethanol according to [31] or [32], wherein a molar ratio of silica/alumina of zeolite in the zeolite-containing catalyst is 20 to 2000.

[34]

The method for converting ethanol according to any of [31] to [33], wherein the zeolite-containing catalyst comprises a phosphorus element or a silver element.

[35]

A method for producing a hydrocarbon, comprising:

contacting a raw material mixture containing ethylene and ethanol with a catalyst in an adiabatic reactor to obtain a reaction gas containing an olefin having 3 or more carbon atoms.

[36]

A method for producing a hydrocarbon, comprising:

a cracking step of decomposing a hydrocarbon having 2 or more carbon atoms; and a refining step of refining a component obtained in the cracking step, wherein in the refining step, the reaction gas obtained by the method for converting ethanol according to any of [1] to [34] or a refined fraction thereof is combined with the component.

[37]

A method for producing a monomer, comprising:

an unsaturated hydrocarbon-separating step of separating a fraction mainly containing an unsaturated hydrocarbon from a reaction gas obtained by a method for converting ethanol according to any of [1] to [34].

[38]

A method for producing an olefin, comprising:

an olefin-separating step of separating a fraction mainly containing an olefin from the reaction gas obtained by the method for converting ethanol according to any of [1] to [34].

[39]

A method for producing propylene, comprising:

a propylene-separating step of separating a fraction mainly containing propylene from the reaction gas obtained by the method for converting ethanol according to any of [1] to [34].

[40]

A method for producing ethylene, comprising:

an ethylene-separating step of separating a fraction mainly containing ethylene from the reaction gas obtained by the method for converting ethanol according to any of [1] to [34].

[41]

A method for producing a diene, comprising:

a diene-separating step of separating a fraction mainly containing a diene from the reaction gas obtained by the method for converting ethanol according to any of [1] to [34].

[42]

A method for producing an acrylic monomer, comprising:

an unsaturated hydrocarbon-separating step of separating a fraction mainly containing an unsaturated hydrocarbon from the reaction gas obtained by the method for converting ethanol according to any of [1] to [34]; and an acrylic monomer-producing step of obtaining an acrylic monomer from the unsaturated hydrocarbon obtained by the unsaturated hydrocarbon-separating step.

[43]

A method for producing acrylonitrile, comprising:

a propylene-separating step of separating a fraction mainly containing propylene from the reaction gas obtained by the method for converting ethanol according to any of [1] to [34]; and an acrylonitrile-producing step of obtaining acrylonitrile from the propylene obtained by the propylene-separating step.

[44]

A method for producing styrene, comprising:

an ethylene-separating step of separating a fraction mainly containing ethylene from the reaction gas obtained by the method for converting ethanol according to any of [1] to [34]; and a styrene-producing step of obtaining styrene from the ethylene obtained by the ethylene-separating step.

[45]

A method for producing a polymer, comprising:

a step of polymerizing a monomer obtained by the method according to [37].

[46]

A method for producing an olefin-based polymer, comprising:

a step of polymerizing a polymerizable composition comprising the olefin obtained by the method according to [38].

[47]

A method for producing a polypropylene-based polymer, comprising:

a step of polymerizing a polymerizable composition comprising the propylene obtained by the method according to [39].

[48]

A method for producing a polyethylene-based polymer, comprising:

a step of polymerizing a polymerizable composition comprising the ethylene obtained by the method according to [40].

[49]

A method for producing a diene-based polymer, comprising:

a step of polymerizing a polymerizable composition comprising the diene obtained by the method according to [41].

[50]

A method for producing an acrylic monomer-based polymer, comprising:

a step of polymerizing a polymerizable composition comprising the acrylic monomer obtained by the method according to [42].

[51]

A method for producing an acrylonitrile-based polymer, comprising:

a step of polymerizing a polymerizable composition comprising the acrylonitrile obtained by the method according to [43].

[52]

A method for producing a styrene-based polymer, comprising:

a step of polymerizing a polymerizable composition comprising the styrene obtained by the method according to [44].

[53]

A method for producing an aromatic compound, comprising:

an aromatic compound-separating step of separating a fraction mainly containing an aromatic compound from the reaction gas obtained by the method for converting ethanol according to any of [1] to [34].

[54]

A method for producing an aromatic monomer, comprising:

an aromatic monomer-producing step of obtaining an aromatic monomer from the aromatic compound obtained by the method according to [53].

[55]

A method for producing an aromatic monomer-based polymer, comprising:

a step of polymerizing a polymerizable composition comprising the aromatic monomer obtained by the method according to [53].

[56]

An apparatus for converting ethanol, comprising:

a reactor which contacts a raw material mixture containing ethanol and ethylene with a catalyst in an adiabatic reactor to obtain a reaction gas containing an olefin having 3 or more carbon atoms; and a first distillation column which separates the reaction gas into fraction A mainly containing a hydrocarbon having 2 to 3 carbon atoms and fraction B mainly containing a hydrocarbon having 4 to 6 carbon atoms, wherein at least a portion of the fraction A is recycled to the reactor to be used as a portion of the raw material mixture.

[57]

The apparatus for converting ethanol according to [57], further comprising:

a second distillation column which separates the fraction A into fraction A-1 mainly containing a hydrocarbon having 2 carbon atoms and fraction A-2 mainly containing a hydrocarbon having 3 carbon atoms, wherein at least a portion of the fraction A-2 is recycled to the reactor to be used as a portion of the raw material mixture.

[58]

The apparatus for converting ethanol according to [58], wherein the first distillation column has a side-cut stage for obtaining an intermediately discharged outflow.

BRIEF DESCRIPTION OF DRAWINGS

FIG. 1 shows a schematic view of one embodiment of a fixed-bed single-stage adiabatic reactor.

FIG. 2 shows one embodiment of a flow in the reaction step and the separation step.

FIG. 3 shows one embodiment of a flow in the reaction step, the separation step, and steam cracking.

FIG. 4 shows one embodiment of a flow in the reaction step and the separation step.

FIG. 5 shows one embodiment of a flow in the reaction step and the separation step.

FIG. 6 shows one embodiment of a flow in the reaction step and the separation step.

FIG. 7 shows a schematic view of one embodiment of an apparatus for converting ethanol and ethylene.

FIG. 8 shows a schematic view of one embodiment of an apparatus for converting ethanol and ethylene.

FIG. 9 shows a schematic view of one embodiment of an apparatus for converting ethanol and ethylene.

FIG. 10 shows a schematic view of one embodiment of an apparatus for converting ethanol and ethylene.

FIG. 11 shows a schematic view of one embodiment of an apparatus for converting ethanol and ethylene.

FIG. 12 shows a schematic view of a conversion apparatus, for comparison with the apparatus for converting ethanol and ethylene according to the present embodiment in terms of their effects.

FIG. 13 shows a schematic view of a conversion apparatus, for comparison with the apparatus for converting ethanol and ethylene according to the present embodiment in terms of their effects.

DESCRIPTION OF EMBODIMENTS

Hereinafter, the present invention will be specifically described. The present invention is not limited by the following embodiments (present embodiment) and can be carried out through various changes or modification without departing from the gist of the present invention.

Herein, a numerical range represented by using "to" means a range including the numerical values described before and after "to" as the minimum value and the maximum value, respectively. In numerical ranges described in stages herein, the upper limit value or the lower limit value of a numerical range at a certain stage may be arbitrarily combined with the upper limit value or the lower limit value of a numerical range at a different stage.

Herein, the "target compound" is a hydrocarbon such as an olefin or an aromatic compound. Examples of the olefin include ethylene, propylene, butene, and butadiene. Examples of the aromatic compound include benzene, toluene, and xylene.

The target compound may be appropriately changed according to a status such as a demand. In the method for converting ethanol according to the present embodiment, propylene, which has 3 carbon atoms, or an aromatic compound, which has 6 or more carbon atoms, can also be obtained from ethanol having 2 carbon atoms.

First Embodiment

First, the method for converting ethanol according to the first embodiment will be described.

Method for Converting Ethanol

First Embodiment

The method for converting ethanol according to the first embodiment comprises:

- contacting a raw material mixture containing ethylene and ethanol with a catalyst in an adiabatic reactor to obtain a reaction gas containing an olefin having 3 or more carbon atoms (hereinafter, also referred to as a "reaction step").

Heretofore, production of chemical product by using not only olefins but also alcohols, as raw materials, such as ethanol produced from biomass raw materials, has received attention due to a rising demand for environmental protection in recent years. Among them, ethanol is a compound having the same number of carbon atoms as that of ethylene, i.e., 2 carbon atoms. Therefore, early development of an efficient method for producing a hydrocarbon compound such as propylene by converting ethanol has been awaited.

In a chemical process, the selection of a reactor and its mode is a factor that largely influences the ease of operation or the size of an environmental load. A fixed-bed adiabatic reactor is an ideal reactor having small loads of design, construction, and operation because the reactor is neither heated nor cooled and furthermore, is free from a complicated structure as compared with a fluidized-bed reactor or the like. If a fixed-bed single-stage adiabatic reactor, for example, can be adopted, its advantage is further enhanced. However, the reactor cannot be applied to a largely endothermic or exothermic reaction system disadvantageously.

As a method for suppressing change in internal temperature of the reactor caused by the influence of heat of reaction, it is effective to mix a plurality of compounds and to use the mixture as a raw material to cause different reactions, i.e., endothermic and exothermic reactions to thereby allow the exotherm and the endotherm to cancel each other out in the system, i.e., to create a thermally neutralized state. However, for selecting different raw materials that provide a single target substance with the aim of thermally neutralizing the reaction system, it is necessary to carefully select the raw materials so as not to inhibit their respective reactions, and it is also necessary to develop a combination in consideration of the respective properties of the raw materials. Therefore, the raw materials are difficult to select by focusing on mere heat of reaction from each elementary reaction.

Patent Literatures 1 to 3 each disclose a technique of converting each raw material to a target olefin with a zeolite catalyst. However, these techniques cannot be applied to an adiabatic reactor due to large endotherm and exotherm.

Patent Literatures 4 and 5 each disclose a thermal neutralization technique that exploits exothermic reaction involving conversion of an oxygenate such as an alcohol as a raw material. However, reaction involving use of ethanol, which induces endothermic reaction, as a raw material cannot be carried out in an adiabatic reactor.

Accordingly, an object of the present embodiment is to provide a method for converting ethanol to a target compound in good yield by using an adiabatic reactor and controlling an internal temperature of the reactor.

The present inventors have conducted diligent studies to attain the object described above, and consequently found that ethanol can be converted to a target compound in good yield by using an adiabatic reactor and controlling an internal temperature of the reactor, when controlling heat of reaction as the whole reaction system for the conversion of ethanol to an olefin having 3 or more carbon atoms and the conversion of ethylene to an olefin having 3 or more carbon atoms.

According to the present embodiment, a target compound such as propylene can be produced in good yield by using an adiabatic reactor and controlling an internal temperature of the reactor. According to the present embodiment, environmentally friendly conversion of ethanol having a small load of operation and high energy efficiency can be carried out by using an adiabatic reactor. Even in the case of using an adiabatic reactor, a target compound such as propylene can be provided in good yield, and coking deactivation can be suppressed. Therefore, the method of the present embodiment is suitable as a method for converting ethanol.

The present inventors have gained the finding that in an attempt to produce propylene from ethylene or ethanol alone as a raw material in an adiabatic reactor, as mentioned above, the yield of a target compound such as propylene is decreased, or the coking deactivation of a catalyst proceeds. The coking deactivation of a catalyst means that coke is deposited on catalyst surface to reduce the activity of the catalyst.

On the basis of such a finding, the present inventors have found that when a raw material mixture containing ethylene and ethanol is contacted with a catalyst filled into an adiabatic reactor, a target compound such as propylene can be provided in good yield and coking deactivation can be suppressed.

This is presumably because thermal neutralization can be achieved by combining endothermic reaction and exothermic reaction that do not inhibit each other. The conversion of ethylene to propylene is exothermic reaction. The conversion of ethanol to propylene is endothermic reaction composed of two-stage reaction, the dehydration reaction of ethanol to ethylene and the conversion reaction of ethylene to propylene, in the presence of a catalyst. The conversion of ethylene to propylene and the conversion of ethanol to propylene have been found to proceed without inhibiting each other, and the combination of the exothermic and the endothermic reactions has presumably enabled reaction conditions to be easily controlled even for an adiabatic reactor in the present embodiment. However, the cause is not limited thereto.

(Raw Material)

The method for converting ethanol according to the present embodiment employs a raw material mixture containing ethylene and ethanol. By use of the raw material mixture, propylene can be produced in good yield by using an adiabatic reactor and controlling an internal temperature of the reactor.

The molar ratio of ethylene/ethanol in the raw material mixture is preferably 0.20 to 2.5, more preferably 0.20 to 2.0, further preferably 0.30 to 1.8, particularly preferably 0.30 to 1.5.

Ethylene produced by any of various production methods can be used. For example, ethylene obtained through thermal cracking of naphtha and/or ethane, direct or oxidative dehydrogenation of ethane, or dehydration of ethanol can be used. Likewise, ethanol produced by any of various methods can be used. Among them, bioethanol or waste-derived ethanol is preferably used in view of excellent environmental friendliness. Such ethylene and ethanol often undergo a step in which water is produced as a by-product or coexists in a reactor in their production process. Thus, in the method for converting ethanol according to the present embodiment, ethylene and ethanol as a raw material may contain water.

In the method for converting ethanol according to the present embodiment, the raw material mixture may further comprise an olefin having 4 to 6 carbon atoms. The olefin having 4 to 6 carbon atoms can provide a target compound such as propylene by contact with a catalyst, as in ethylene and ethanol. Examples of the olefin having 4 to 6 carbon atoms include butene, pentene, and hexene. Herein, the term "olefin" includes linear, branched, and cyclic olefins as well as cycloparaffin.

The molar ratio of olefin having 4 to 6 carbon atoms/ethylene in the raw material mixture is preferably 3.0 or less, more preferably 1.0 or less, further preferably 0.5 or less, further preferably 0.15 to 0.5.

In the method for converting ethanol according to the present embodiment, the raw material mixture may further comprise an oxygenate having 1 to 6 carbon atoms other than ethanol. The oxygenate having 1 to 6 carbon atoms can provide a target compound such as propylene by contact with a catalyst, as in ethylene and ethanol. Examples of the oxygenate having 1 to 6 carbon atoms other than ethanol include methanol, propanol, dimethyl ether, and diethyl ether.

The molar ratio of oxygenate having 1 to 6 carbon atoms other than ethanol/ethanol in the raw material mixture is preferably 1.0 or less, more preferably 0.5 or less.

Ethylene, ethanol, an olefin having 4 to 6 carbon atoms, and an oxygenate having 1 to 6 carbon atoms other than ethanol are also collectively referred to as an "effective raw material".

The raw material mixture may comprise, in addition to the effective raw material described above, a saturated aliphatic hydrocarbon such as paraffin, an olefin having 7 or more carbon atoms, and an oxygenate having 7 or more carbon atoms. The saturated aliphatic hydrocarbon, the olefin having 7 or more carbon atoms, and the oxygenate having 7 or more carbon atoms are capable of being converted to a target compound such as propylene through dehydrogenation reaction or dehydration reaction or combination thereof by contact with a catalyst, as in ethylene and ethanol, though their reactivity is lower than that of the effective raw material mentioned above.

The raw material mixture can comprise the whole amount or a portion of an olefin having 4 or more carbon atoms separated, in the separation step, from the reaction gas containing an olefin having 3 or more carbon atoms obtained by the reaction step. In this way, effective use of an olefin raw material can be achieved by using a so-called recycling reaction system.

The raw material mixture may comprise an inert gas such as nitrogen, in addition to the aforementioned raw material capable of being converted to a target compound such as propylene by the reaction step. The raw material mixture may also comprise hydrogen or methane as a dilution gas. It is however preferred to not dilute with hydrogen. Although hydrogen may be used for suppressing the coking deactivation of a catalyst, hydrogen also causes hydrogenation of produced propylene or the like, which has an adverse effect of reducing propylene purity (propylene/(propylene+propane)). The method of the present embodiment has a small coking deactivation rate of a catalyst and permits stable operation even if dilution with hydrogen is not performed. Therefore, it is preferred to not dilute with hydrogen. However, a small amount of hydrogen fed into a reactor, for example, by the recycling of a fraction separated from the reaction gas is free from such an adverse effect found in the dilution with hydrogen.

The total proportion of ethylene, an olefin having 4 to 6 carbon atoms, and ethanol in the raw material mixture is preferably 40% by mass or more, more preferably 50% by mass or more, based on a mass flow rate of the raw material mixture fed. The mass flow rate of the raw material mixture fed is the total flow rate of all compounds to be fed into a reactor, including an inert component.

The total content of ethylene and ethanol in the raw material mixture is preferably 30 to 100% by mass, more preferably 40 to 100% by mass, further preferably 50 to 100% by mass, based on the mass of the effective raw material fed. Here, as for ethanol, the mass thereof in terms of ethylene is used in the calculation of the mass of ethanol and the mass of the effective raw material fed.

The total content of olefins having 4 to 6 carbon atoms in the raw material mixture is preferably 65% by mass or less, more preferably 10 to 55% by mass, based on the mass of the effective raw material fed.

The mass of the effective raw material fed is the total mass per hour of the effective raw material fed. Here, as for ethanol, the mass thereof in terms of ethylene is used in the calculation.

In the method for converting ethanol according to the present embodiment, the raw material mixture may comprise water. Ethylene and ethanol contained in the raw material mixture are produced by various production methods and may therefore contain "water generated in the production process". In this context, the "water generated in the production process" refers to moisture that is generated in an ethylene and/or ethanol production process and remains unremoved.

In the method for converting ethanol according to the present embodiment, the raw material mixture can comprise water vapor in addition to the "water generated in the production process". The water vapor is effective for decreasing an olefin partial pressure, thereby suppressing coking deactivation and improving the yield of a lower olefin. On the other hand, the water vapor might promote dealumination of zeolite. Therefore, preferably, the raw material mixture comprises no water vapor in addition to the "water generated in the production process".

(Adiabatic Reactor)

The method for converting ethanol according to the present embodiment employs an adiabatic reactor. For the adiabatic reactor, see the description of Adiabatic Fixed-Bed Reactors (Elsevier, 2014, Ch. 1, P. 4, L. 5-24, ISBN:978-0-12-801306-9). Examples of the adiabatic reactor include fixed-bed adiabatic reactors, moving-bed adiabatic reactors, and fluidized-bed adiabatic reactors. In the method of the present embodiment, a fixed-bed adiabatic reactor is preferred. The fixed-bed adiabatic reactor is more preferably a fixed-bed single-stage adiabatic reactor, which has a single stage of a fixed catalyst bed. Since a carbonaceous material (coke) is deposited on a catalyst in association with reaction, a multi-column switchable fixed-bed single-stage adiabatic reactor, which is capable of removing this carbonaceous material by combustion while continuing the reaction, is preferred.

FIG. 1 is a schematic view of the configuration of the fixed-bed single-stage adiabatic reactor. Fixed-bed single-stage adiabatic reactor 1 has reaction housing 12 having heat insulation material 121 provided on its outer periphery, catalyst bed 13, reactor inlet 14, and reactor outlet 15. The reaction housing 12, which has the heat insulation material 121 provided on its outer periphery, does not allow the internal heat of the reactor to escape to the outside. In the production method according to the present embodiment, the internal temperature of the reactor can be controlled through exothermic and endothermic reactions.

The catalyst bed 13 is filled with a catalyst mentioned later. First sheathed thermocouple 161 is disposed immediately upstream of catalyst bed inlet 131 of the catalyst bed 13. Second sheathed thermocouple 162 is disposed immediately downstream of catalyst bed outlet 132 of the catalyst bed 13. These thermocouples measure the temperatures of the raw material mixture immediately before contact with the catalyst bed inlet 131 and the reaction gas immediately after passage through the catalyst bed outlet 132. The catalyst bed 13 may be of multi-column type and is preferably of single-stage type as shown in FIG. 1.

In the fixed-bed single-stage adiabatic reactor 1, the raw material mixture is introduced from the reactor inlet 14 and contacted with the catalyst bed 13, and the reaction gas is taken out of the reactor outlet 15.

(Conditions of Reaction Step)

In the method for converting ethanol according to the present embodiment, the reaction temperature may be 300 °C. or higher. Because of the presence of thermal equilibrium in a produced olefin, the reaction temperature is preferably 450 °C. or higher in view of higher improvement in a propylene yield. The reaction temperature is preferably lower than 600 °C. in view of suppressing coking deactivation, which is promoted at a high temperature. More specifically, the temperature of the reaction gas at the catalyst bed inlet is preferably 450 °C to 590 °C, and the temperature of the reaction gas at the catalyst outlet is preferably 450 °C to 590 °C.

The temperature difference between the catalyst bed outlet temperature and the catalyst bed inlet temperature is preferably −80 K to 80 K, more preferably −60 K to 60 K.

The catalyst bed inlet temperature is the temperature of the raw material mixture immediately before the raw material fluid comes into contact with the catalyst bed filled into the adiabatic reactor. The catalyst bed outlet temperature is the temperature of the reaction gas immediately after the reaction gas passes through the catalyst bed. In this context, the temperatures of the raw material mixture and the reaction gas refer to temperatures at 0 d to 0.8 d, wherein d represents the distance from the center of the reactor to the inner wall surface of the reactor when the center of the reactor in a plane perpendicular to the flow direction of a fluid is defined as 0. The inlet-outlet average reaction temperature (hereinafter, also simply referred to as a "reaction temperature") is defined as a value calculated according to the expression: [Catalyst bed inlet temperature+Catalyst bed outlet temperature]/2, wherein the catalyst bed inlet temperature and the catalyst bed outlet temperature are measured, as shown in FIG. 1.

The reaction pressure is preferably 0.01 to 3.0 MPaG, more preferably 0.01 to 1.0 MPaG.

The feed rate of the effective raw material is preferably 0.1 to 1000 $hr^{-1}$, more preferably 0.1 to 500 $hr^{-1}$, further preferably 0.5 to 100 $hr^{-1}$, in terms of the weight hourly space velocity (WHSV) of a catalyst. In the method for converting ethanol according to the present embodiment, WHSV is calculated by using an ethanol flow rate in terms of ethylene as shown in the expression given below. The mass flow rate of the effective raw material fed is preferably 1 kg/hr or more, more preferably 10 kg/hr or more, further preferably 1,000 kg/hr or more, in view of excellent productivity of a target compound such as propylene or an aromatic compound.

$$WHSV\,(\mathrm{hr}^{-1}) = \text{Mass flow rate of effective raw material fed (kg/hr)/Amount (kg) of catalyst}$$

$$\text{Mass flow rate of effective raw material fed (kg/hr)} = \text{Ethylene flow rate (kg/hr)} + \text{Ethanol flow rate in terms of ethylene (kg/hr)} + \text{Flow rate (kg/hr) of olefin having 4 to 6 carbon atoms} + \text{Flow rate (kg/hr) of oxygenate having 1 to 6 carbon atoms other than ehtanol}$$

$$\text{Ethanol flow rate in terms of ethylene (kg/hr)} = \text{Ehtanol flow rate (kg/hr)} \times \text{Molecular weight (g/mol) of ethylene/Molecular weight (g/mol) of ethanol}$$

(Catalyst)

In the method for converting ethanol according to the present embodiment, the catalyst is a solid catalyst that exhibits the ability to catalyze the conversion of an olefin and ethanol to a target compound such as propylene. Such a catalyst is preferably a zeolite-containing catalyst in view of excellent thermal durability of the catalyst and propylene selectivity. A common challenge to conventional olefin production involving use of zeolite is coking deactivation caused by a heavy carbonaceous material (coke) that accumulates inside zeolite pores through reaction with a hydrocarbon and deactivates the zeolite. For regenerating catalyst performance, it is preferred to remove coke by combustion in an atmosphere containing an oxygen molecule. In association with this combustion of coke, however, structural collapse of zeolite proceeds to induce permanent deterioration of the catalyst impossible to regenerate. According to the method for converting ethanol according to the present embodiment, the zeolite-containing catalyst used easily maintains its activity because the production of coke can be suppressed.

<<Zeolite-Containing Catalyst>>

The zeolite-containing catalyst is a catalyst powder or compact containing zeolite as an active species. In the method for converting ethanol according to the present embodiment, so-called medium pore-size zeolite, which has a pore size of 5 to 6 angstroms, is preferably used as zeolite in the zeolite-containing catalyst described above. The medium pore-size zeolite means "zeolite whose pore size range is in between the pore size of small pore-size zeolite typified by type A zeolite and the pore size of large pore-size zeolite typified by mordenite or type X or Y zeolite". The "medium pore-size zeolite" has a so-called oxygen 10-membered ring in its crystal structure.

Examples of the medium pore-size zeolite include ZSM-5, ZSM-8, ZSM-11, ZSM-12, ZSM-21, ZSM-23, ZSM-35, and ZSM-38. Among them, ZSM-5-type zeolite such as ZSM-5, ZSM-11, or ZSM-8, or ZSM-38 is preferred. Alternatively, zeolite similar to ZSM-5 or ZSM-11 described in Stud. Surf. Sci. Catal. 1987, 33, 167-215 can be used. Among them, MFI-type zeolite is preferred, and ZSM-5 is more preferred, in view of excellent catalyst performance (catalytic activity and durability against coking).

The silica/alumina ($SiO_2/Al_2O_3$) molar ratio of zeolite contained in the zeolite-containing catalyst of the present embodiment can be appropriately selected and is preferably 20 to 2000 in view of excellent catalytic activity and propylene selectivity, and more preferably 100 to 1500, further preferably 300 to 1200, still further preferably 800 to 1200, in view of enhancing the durability of the catalyst. The silica/alumina ($SiO_2/Al_2O_3$) molar ratio of zeolite contained in the zeolite-containing catalyst may be 20 to 400 or may be 100 to 300. The silica/alumina molar ratio of zeolite can be measured by a known method and can be determined, for example, by completely dissolving the zeolite in an aqueous alkali solution, and analyzing the resulting solution by plasma emission spectroscopy or the like.

A method for synthesizing the zeolite of the present embodiment is not particularly limited, and the zeolite can be produced by optimizing various conditions for a conventionally known hydrothermal synthesis method of MFI-type zeolite. In general, an approach of efficiently obtaining MFI-type zeolite by a hydrothermal synthesis method includes a method including hydrothermally synthesizing the zeolite with an appropriate organic structure-directing agent (SDA), a method including hydrothermally synthesizing the zeolite by adding hydrothermally synthesized MFI zeolite as seed crystals, or a method including hydrothermally synthesizing the zeolite by adding a seed slurry at a crystalline stage. In this context, examples of the organic structure-directing agent (SDA) used include ammonium salts, urea compounds, amine, and alcohols. Not only organic SDA but an inorganic cation or anion is known to be structurally involved, and the zeolite synthesis depends on complex work of individual components. The hydrothermal synthesis method of MFI-type zeolite as mentioned above can produce a suitable catalyst by appropriately optimizing synthesis conditions such as the type of a raw material or an additive (SDA), the amount of the additive, pH, a silica/alumina molar ratio, a medium, raw material charging composition (e.g., the abundance ratio of a cation or an anion), a synthesis temperature, and a synthesis time.

Specific examples thereof include a synthesis method involving use of a seed slurry described in Japanese Patent No. 5426983, and methods illustrated in The Hydrothermal Synthesis of Zeolites (Chemical Reviews, 2003, 103, 663-702).

Commercially available zeolite may be used as long as the zeolite is the aforementioned MFI zeolite having specific physical properties and composition.

The zeolite-containing catalyst according to the present embodiment preferably comprises a phosphorus element or a silver element.

Examples of the form of the phosphorus element include phosphorus polymers (e.g., polyphosphoric acid), phosphorus oxides (e.g., $P_2O_5$), and compounds having phosphorus added to aluminum of zeolite. A plurality thereof may be contained. The phosphorus element is effective for suppressing dealumination of zeolite when the zeolite contains aluminum, or is effective for improving a propylene yield in some cases. Particularly, in the case of an application involving exposure to a high-temperature water vapor atmosphere, the characteristics of the zeolite-containing catalyst are easily changed by dealumination, and therefore, the effect of suppressing dealumination is more improved.

The content of the phosphorus element contained in the zeolite-containing catalyst is preferably 0.01 to 2.0% by mass based on the mass of the whole catalyst, and is more preferably 0.05 to 2.0% by mass in view of the excellent effect of suppressing dealumination.

In the present embodiment, the content of the phosphorus element in the catalyst refers to a value found using an X-ray fluorescence analyzer. The content of the phosphorus element can be measured using a commercially available X-ray fluorescence analyzer under usual conditions in accordance with its instruction manual. In the case of using, for example, trade name “RIX3000” manufactured by Rigaku Corp., measurement conditions can involve a tube voltage of 50 kV and a tube current of 50 mA using P-Kα ray.

In the present embodiment, phosphoric acid and/or phosphate (hereinafter, also referred to as a “phosphorus raw material”) is used as a raw material for the phosphorus element contained in the zeolite-containing catalyst. The phosphorus raw material is more preferably phosphate, and the phosphate is more preferably a compound having a solubility of 1 g or more in 100 g of water at 25 °C.

Examples of the phosphoric acid include phosphoric acid and pyrophosphoric acid. Examples of the phosphate include phosphoric acid ammonium salts such as ammonium phosphate, diammonium hydrogen phosphate, ammonium dihydrogen phosphate, and ammonium sodium hydrogen phosphate, potassium hydrogen phosphate, aluminum hydrogen phosphate, sodium phosphate, and potassium phosphate. Among them, a phosphoric acid ammonium salt having a relatively high solubility in water is preferred, and at least one member selected from the group consisting of ammonium phosphate, diammonium hydrogen phosphate, and ammonium dihydrogen phosphate is more preferred. These compounds may each be used singly or may be used in combination of two or more.

The form of the silver element is, for example, a silver ion. The silver element is effective for controlling the acid site of zeolite, thereby improving the hydrothermal resistance of the zeolite.

The content of the silver element contained in the zeolite-containing catalyst is preferably 0.01 to 2.0% by mass based on the mass of the whole catalyst, and is more preferably 0.05 to 2.0% by mass in view of the excellent effect of improving hydrothermal resistance per content.

In the present embodiment, the content of the silver element in the catalyst refers to a value found using an X-ray fluorescence analyzer. The content of the silver element can be measured using a commercially available X-ray fluorescence analyzer under usual conditions in accordance with its instruction manual. In the case of using, for example, trade name “RIX3000” manufactured by Rigaku Corp., measurement conditions can involve a tube voltage of 50 kV and a tube current of 50 mA using P-Kα ray.

In the present embodiment, silver nitrate is used as a raw material for the silver element contained in the zeolite-containing catalyst. A zeolite-containing catalyst containing sodium as a counter cation is used in ion exchange with silver nitrate and the resultant is sintered to obtain a zeolite-containing catalyst containing a silver element. The ion exchange of sodium serving as a counter cation in zeolite with silver nitrate can be carried out by dipping the zeolite or the zeolite-containing catalyst in an aqueous solution of silver nitrate, followed by washing with water. In this respect, the ion exchange rate can be improved by carrying out the dipping and the washing with water a plurality of times.

The zeolite-containing catalyst of the present embodiment can be produced by using the aforementioned zeolite having specific physical properties and composition, and molding the zeolite, for example, as described below. The molding method is not particularly limited, and a general method can be used. Specific examples thereof include a method including compression-molding a catalytic component, a method including extrusion-molding a catalytic component, and a spray dry molding method optimal for a fluidized-bed reaction scheme.

A binder can be used in the molding. The binder is not particularly limited, and, for example, silica, alumina, and kaolin can each be used alone or can be used as a mixture. Commercially available products can be used as these binders. The mass ratio of zeolite/binder is preferably in the range of 10/90 to 90/10, more preferably in the range of 20/80 to 80/20. A silica binder is preferred in view of suppression of coking.

In the method for converting ethanol according to the present embodiment, the zeolite-containing catalyst may be subjected to a pretreatment step, prior to contacting the raw material with the zeolite-containing catalyst. The pretreatment step is preferably a heat treatment step at a temperature of 300 °C. or higher in the presence of water vapor. The pretreatment tends to more remarkably produce the effect of suppressing the deterioration of the catalyst or improving selectivity. In the case of the method described above, the treatment is preferably performed at a temperature of 300 °C. or higher and 900 °C. or lower in an atmosphere of, but not particularly limited to, a mixed gas of air or an inert gas (such as nitrogen) and steam (water vapor) circulated under conditions involving a water vapor partial pressure of 0.01 atm or more. The heat treatment temperature is more preferably a temperature of 400 °C. or higher and 700 °C. or lower. This pretreatment step can be performed using a reactor for converting ethanol.

(Product: Reaction Gas Comprising Olefin Having 3 or More Carbon Atoms)

In the method for converting ethanol according to the present embodiment, the raw material mixture is contacted with the catalyst to obtain a reaction gas comprising an olefin having 3 or more carbon atoms. The “reaction gas” means a gas composition after reaction caused by the contact of the raw material mixture with the catalyst. The reaction gas may comprise ethylene. The reaction gas may comprise hydrogen, an aliphatic hydrocarbon having 1 to 3 carbon atoms, an aliphatic hydrocarbon having 4 to 8 carbon atoms, an aromatic compound, and a hydrocarbon having 9 or more carbon atoms.

[Regeneration Step]

When a catalyst is used in reaction for a long period, coke may be deposited onto the catalyst, causing coking deactivation. If the catalyst has undergone coking deactivation, for example, coke on the catalyst can be contacted with an oxygen-containing gas and removed by combustion at a temperature of 400 to 700 °C to regenerate the catalyst that has undergone coking deactivation (hereinafter, also referred to as a “regeneration step”). Examples of the oxygen-containing gas include air and a mixed gas of air or oxygen and an inert gas. The oxygen concentration of the oxygen-containing gas is preferably 0.1 to 2.0% by volume. For the catalyst, any regeneration method may be adopted, including extra-reactor regeneration, which involves discharging the catalyst from the reactor and performing regeneration treatment outside the reactor, and intra-reactor regeneration, which involves performing regeneration treatment inside the reactor without discharging the catalyst from the reactor. Alternatively, reaction-regeneration switching operation may be performed by adopting a switchable reactor.

(Reaction-Regeneration Switching Operation)

The reaction-regeneration switching operation is an operational procedure of performing the reaction step and the regeneration step at the same time using a double-column or multi-column switchable adiabatic reactor. In the case of, for example, a triple-column switchable reactor, two columns are used in the reaction step while the remaining one column is used in the catalyst regeneration. Then, the reaction step of one of the columns used in the reaction step is terminated, and the catalyst regeneration is performed instead. The reaction step is performed in the one column used in the catalyst regeneration. As a result, the catalyst regeneration can be performed while production capacity derived from two columns is maintained. Such a reaction format, also called merry-go-round scheme, is preferred in view of production efficiency because of the absence of the need of discontinuing the production process for catalyst regeneration.

[Separation Step]

The method for converting ethanol according to the present embodiment can comprise separating a target compound such as propylene from the reaction gas (hereinafter, also referred to as a "separation step"). By the separation step, ethylene and propylene can be separated from the reaction gas.

The method according to the present embodiment can be carried out by an apparatus having reactor 1, distillation column 2, distillation column 3, and distillation column 4, as shown in FIG. 2. The reaction gas obtained by the reaction step performed in the reactor 1 can be separated into fraction A mainly containing a hydrocarbon having 1 to 3 carbon atoms and fraction B mainly containing a hydrocarbon having 4 to 8 carbon atoms by the distillation column 2. Before distillation in the distillation column 2, condensed water may be removed from the reaction gas (not shown). In the distillation column 3 and the distillation column 4, the separation of ethylene and propylene from the reaction gas is efficiently performed by separating ethylene and propylene from the fraction A. At least a portion of the reaction gas and/or the fraction A may be introduced to the refining system of an ethylene plant, and ethylene and propylene can be separated from the reaction gas by the refining system. Various fractions including the fraction B obtained by the separation step can be recycled as a raw material to the reactor.

The method according to the present embodiment can be carried out by an apparatus having reactor 1, distillation column 2, and steam cracking apparatus 5, as shown in FIG. 3. The fraction B obtained by the separation step is subjected to steam cracking to obtain a steam cracking product containing ethylene and propylene. The efficiency of the whole process can be enhanced by separating ethylene and propylene from the steam cracking product. The steam cracking means thermal decomposition of a compound in a fraction, together with heating steam.

The method according to the present embodiment can be carried out by an apparatus having reactor 1, cooling apparatus 6, distillation column 2, and oily water separator 7, as shown in FIG. 4. A cooling step can be performed in which the reaction gas obtained by the reaction step performed in the reactor 1 is cooled by the cooling apparatus 6. By the cooling step, the reaction gas can be separated into fraction C mainly containing an aliphatic hydrocarbon having 2 to 6 carbon atoms and fraction D mainly containing water, an aliphatic hydrocarbon having 7 or more carbon atoms, and an aromatic compound. In the cooling step, the fraction C is obtained as a gas component, and the fraction D is recovered as a liquid component. The separation of an aromatic compound from the reaction gas is efficiently performed by separating the aromatic compound from the fraction D.

The fraction D recovered in the cooling step is separated into fraction E mainly containing a hydrocarbon and fraction F mainly containing water by the oily water separator 7. The separation of an aromatic compound from the reaction gas is efficiently performed by separating the aromatic compound from the fraction E. The separation of the aromatic compound is carried out by, for example, distillation, extractive distillation, extraction, crystallization, or a combination thereof.

The method according to the present embodiment can be carried out by an apparatus having reactor 1, distillation column 2, and distillation column 8, as shown in FIG. 5. When the fraction B is recycled by the distillation column 8, it is preferable to separate into fraction B1 mainly containing an aliphatic hydrocarbon, preferably an olefin, having 4 to 6 carbon atoms and fraction B2 mainly containing an aromatic compound and to recycle at least a portion of the fraction B1 to the reactor. The aromatic compound which is not converted to propylene can be removed from the raw material by using, as a recycled raw material, the fraction B1 from which the fraction B2 has been removed. Thus, propylene can be efficiently produced. In this way, the aromatic compound may be separated as the fraction B2 from the fraction B. Further separation and refining of the aromatic compound are carried out by, for example, distillation, extractive distillation, extraction, crystallization, or a combination thereof.

The method according to the present embodiment can be carried out by an apparatus having reactor 1, distillation column 2, and distillation column 9, as shown in FIG. 6. It is preferable to separate the fraction B, by the distillation column 9, into fraction B3 mainly containing a hydrocarbon having 4 to 8 carbon atoms and fraction B4 mainly containing a hydrocarbon having 9 or more carbon atoms and to recycle at least a portion of the fraction B3 to the reactor. A heavy material capable of promoting coking deactivation can be removed from the raw material by using, as a recycled raw material, the fraction B3 from which the fraction B4 has been removed. Thus, the coking deactivation of the catalyst can be suppressed.

The term "mainly containing" for various fractions means that the total mass of the component described with the term "mainly containing" exceeds 50% by mass based on the total amount of the fraction.

These separation steps can be carried out by combining various known methods such as distillation and extraction.

Second Embodiment

Next, the method for converting ethanol according to the second embodiment will be described.

Method for Converting Ethanol

Second Embodiment

The method for converting ethanol according to the second embodiment comprises contacting a raw material mixture containing methanol and ethanol with a catalyst in an adiabatic reactor to obtain a reaction gas containing an olefin having 3 or more carbon atoms (hereinafter, also referred to as a "reaction step").

Propylene can be obtained by separation from the reaction gas mentioned above, and an aromatic compound can also be obtained by separation from the reaction gas mentioned above.

In practical use of a conventional production process of a chemical product, the selection of a reactor and its mode is a factor that largely influences the ease of operation or the size of an environmental load. A fixed-bed adiabatic reactor is an ideal reactor having small loads of design, construction, and operation because the reactor is neither heated nor cooled and furthermore, is free from a complicated structure as compared with a fluidized-bed reactor or the like. If a fixed-bed single-stage adiabatic reactor, for example, can be adopted, its advantage is further enhanced. However, the reactor cannot be applied to a largely endothermic or exothermic reaction system disadvantageously.

Patent Literatures 2, 3, and 6 each disclose a technique of converting each raw material to a target olefin with a zeolite catalyst. However, these techniques cannot be applied to an adiabatic reactor due to large endotherm and exotherm.

Accordingly, an object of the present embodiment is to provide a method for converting an alcohol to a target compound in good yield, a method for producing propylene, and a method for producing an aromatic compound, by using an adiabatic reactor and controlling an internal temperature of the reactor.

The present inventors have conducted diligent studies to attain the object described above, and consequently found that an alcohol can be converted to a target compound in good yield by using an adiabatic reactor and controlling a reaction temperature, when controlling heat of reaction in the reactor for the conversion of a raw material mixture of ethanol and methanol to a target compound such as an olefin having 3 or more carbon atoms.

According to the present embodiment, an alcohol can be converted to a target compound in good yield by using an adiabatic reactor and controlling an internal temperature of the reactor. According to the present embodiment, an environmentally friendly conversion method of an alcohol having a small load of operation and high energy efficiency can be carried out by using an adiabatic reactor. Even in the case of using an adiabatic reactor, an alcohol can be converted to a target compound in good yield, and the coking deactivation of a catalyst can be suppressed. Therefore, the method of the present embodiment is suitable as a method for converting ethanol.

The present inventors have gained the finding that in an attempt to convert an alcohol in an adiabatic reactor using methanol or ethanol alone as a raw material, the yield of a high-value added target compound such as propylene or an aromatic compound is decreased, or the coking deactivation of a catalyst proceeds. The coking deactivation of a catalyst means that coke is deposited on catalyst surface to reduce the activity of the catalyst.

On the basis of such a finding, the present inventors have found that when a raw material mixture containing methanol and ethanol is contacted with a catalyst filled into an adiabatic reactor, the alcohol can be converted to a target compound in good yield and coking deactivation can be suppressed.

This is presumably because thermal neutralization can be achieved by combining endothermic reaction and exothermic reaction that do not inhibit each other. For example, the conversion of methanol to propylene is exothermic reaction, and the conversion of ethanol to propylene is endothermic reaction. The endothermic reaction and the exothermic reaction have been found to proceed without inhibiting each other in a reactor, and the combination of the exothermic reaction and the endothermic reaction has enabled reaction conditions to be easily controlled even for an adiabatic reactor in the present embodiment. However, the cause is not limited thereto.

(Raw Material)

The method for converting ethanol according to the present embodiment employs a raw material mixture containing methanol and ethanol. By use of the raw material mixture, a target compound such as propylene can be produced in good yield by using an adiabatic reactor and controlling an internal temperature of the reactor. At least one of methanol and ethanol is preferably derived from biomass in view of excellent environmental friendliness. The biomass refers to an organic resource other than a fossil resource originating from an animal or a plant. The term "derived from biomass" refers to a compound produced by using the biomass as a raw material.

The molar ratio of methanol/ethanol in the raw material mixture is preferably 0.050 to 2.0, more preferably 0.20 to 1.5, further preferably 0.30 to 1.5, still further preferably 0.30 to 1.0.

Methanol produced by any of various production methods can be used. For example, methanol obtained through hydrogenation of carbon monoxide obtained from a natural gas or coal, hydrogenation of carbon dioxide, or distillation of pyroligneous acid can be used. Likewise, ethanol produced by any of various production methods can be used. Among them, bioethanol or waste-derived ethanol is preferably used in view of excellent environmental friendliness. Such methanol and ethanol often undergo a step in which water is produced as a by-product or coexists in a reactor in their production process. Thus, in the method for converting ethanol according to the present embodiment, methanol and ethanol as the raw material may contain water.

In the method for converting ethanol according to the present embodiment, the raw material mixture may further comprise an olefin having 4 to 6 carbon atoms. The olefin having 4 to 6 carbon atoms can provide a target compound such as propylene by contact with a catalyst, as in methanol and ethanol. The term "olefin" described above includes linear, branched, and cyclic olefins as well as cycloparaffin.

Examples of the olefin having 4 to 6 carbon atoms include butene, pentene, and hexene. The molar ratio of olefin having 4 to 6 carbon atoms/methanol in the raw material mixture is preferably 3.0 or less, more preferably 1.0 or less, further preferably 0.5 or less, still further preferably 0.15 to 0.5.

The raw material mixture may further comprise ethylene. Ethylene can provide a target compound such as propylene by contact with a catalyst, as in methanol and ethanol. The molar ratio of ethylene/ethanol in the raw material mixture is preferably 0.05 or more, more preferably 0.1 or more, further preferably 0.1 to 2.0.

In the method for converting ethanol according to the present embodiment, the raw material mixture may further comprise an oxygenate having 1 to 6 carbon atoms other than methanol and ethanol. The oxygenate having 1 to 6 carbon atoms can provide a target compound such as propylene by contact with a catalyst, as in methanol and ethanol. Examples of the oxygenate having 1 to 6 carbon atoms other than methanol and ethanol include propanol, dimethyl ether, and diethyl ether.

The molar ratio of oxygenate having 1 to 6 carbon atoms other than methanol and ethanol/ethanol in the raw material mixture is preferably 1.0 or less, more preferably 0.5 or less.

Ethylene, ethanol, an olefin having 4 to 6 carbon atoms, and an oxygenate having 1 to 6 carbon atoms other than ethanol are also collectively referred to as an "effective raw material".

The raw material mixture can comprise, in addition to the effective raw material described above, a saturated aliphatic hydrocarbon such as paraffin, an olefin having 7 or more carbon atoms, and an oxygenate having 7 or more carbon atoms. The saturated aliphatic hydrocarbon, the olefin having 7 or more carbon atoms, and the oxygenate having 7 or more carbon atoms are capable of being converted to a target compound such as propylene by contact with a catalyst, as in methanol and ethanol, though their reactivity is lower than that of the effective raw material mentioned above.

The raw material mixture can comprise the whole amount or a portion of the reaction gas containing an olefin having 4 or more carbon atoms obtained by the reaction step or a fraction obtained by the refining of the reaction gas. In this way, effective use of a raw material can be achieved by using a so-called recycling reaction system.

The raw material mixture may comprise an inert gas such as nitrogen, in addition to the aforementioned raw material capable of being converted to a target compound such as propylene by the reaction step. The raw material mixture may also comprise hydrogen or methane as a dilution gas. It is however preferred to not comprise hydrogen (to not dilute with hydrogen). Although hydrogen may be used for suppressing the coking deactivation of a catalyst, hydrogen also causes hydrogenation of produced propylene or the like, which has an adverse effect of reducing propylene purity (propylene/(propylene+propane)) [mol/mol]. The method of the present embodiment has a small coking deactivation rate of a catalyst and permits stable operation even if dilution with hydrogen is not performed. Therefore, it is preferred to not dilute with hydrogen. However, a small amount of hydrogen fed into a reactor, for example, by the recycling of a fraction separated from the reaction gas is free from such an adverse effect found in the dilution with hydrogen.

The total proportion of methanol, an olefin having 4 to 6 carbon atoms, ethanol, and ethylene in the raw material mixture is preferably 40% by mass or more, more preferably 50% by mass or more, based on the total mass flow rate of the raw material mixture fed. The total mass flow rate of the raw material mixture fed is the total flow rate of all compounds to be fed into a reactor, including an inert gas.

The total content of methanol and ethanol in the raw material mixture is preferably 30 to 100% by mass, more preferably 40 to 100% by mass, further preferably 50 to 100% by mass, based on an mass of the effective raw material fed. Here, as for methanol and ethanol, the mass of methanol in terms of methylene and that of ethanol in terms of ethylene are used in the calculation of the mass of methanol, the mass of ethanol, and the mass of the effective raw material fed.

The total content of olefins having 4 to 6 carbon atoms in the raw material mixture is preferably 65% by mass or less, more preferably 10 to 55% by mass, based on the mass of the effective raw material fed.

The mass of the effective raw material fed is the total mass per hour of the effective raw material fed. Here, as for methanol and ethanol, the mass of methanol in terms of methylene and that of ethanol in terms of ethylene are used in the calculation.

In the method for converting ethanol according to the present embodiment, the raw material mixture may comprise water. Methanol and ethanol contained in the raw material mixture are produced by various production methods and therefore contain "water generated in the production process". In this context, the "water generated in the production process" refers to, for example, moisture that is generated in a methanol and/or ethanol production process and remains unremoved.

In the method for converting ethanol according to the present embodiment, the raw material mixture may comprise water vapor in addition to the "water generated in the production process". The water vapor is effective for decreasing an olefin partial pressure, thereby suppressing coking deactivation and improving the yield of a lower olefin. On the other hand, the water vapor might promote dealumination of zeolite. Therefore, preferably, the raw material mixture comprises no water vapor in addition to the "water generated in the production process".

(Adiabatic Reactor)

The method for converting ethanol according to the present embodiment employs an adiabatic reactor. For the adiabatic reactor, see the description of Adiabatic Fixed-Bed Reactors (Elsevier, 2014, Ch. 1, P. 4, L. 5-24, ISBN:978-0-12-801306-9). Examples of the adiabatic reactor include fixed-bed adiabatic reactors, moving-bed adiabatic reactors, and fluidized-bed adiabatic reactors. In the method of the present embodiment, a fixed-bed adiabatic reactor is preferred. The fixed-bed adiabatic reactor is more preferably a fixed-bed single-stage adiabatic reactor, which has a single stage of a fixed catalyst bed. Since a carbonaceous material (coke) is deposited on a catalyst in association with reaction, a multi-column switchable fixed-bed single-stage adiabatic reactor, which is capable of removing this carbonaceous material by combustion while continuing the reaction, is preferred.

FIG. 1 is a schematic view of the configuration of the fixed-bed single-stage adiabatic reactor. Fixed-bed single-stage adiabatic reactor 1 has reaction housing 12 having heat insulation material 121 provided on its outer periphery, catalyst bed 13, reactor inlet 14, and reactor outlet 15. The reaction housing 12, which has the heat insulation material 121 provided on its outer periphery, does not allow the internal heat of the reactor to escape to the outside. In the production method according to the present embodiment, the internal temperature of the reactor can be controlled through exothermic and endothermic reactions.

The catalyst bed 13 is filled with a catalyst mentioned later. First sheathed thermocouple 161 is disposed immediately upstream of catalyst bed inlet 131 of the catalyst bed 13. Second sheathed thermocouple 162 is disposed immediately downstream of catalyst bed outlet 132 of the catalyst bed 3. These thermocouples measure the temperatures of the raw material mixture immediately before contact with the catalyst bed inlet 131 and the reaction gas immediately after passage through the catalyst bed outlet 132. The catalyst bed 13 may be of multi-column type and is preferably of single-stage type as shown in FIG. 1.

In the fixed-bed single-stage adiabatic reactor 1, the raw material mixture is introduced from the reactor inlet 14 and contacted with the catalyst bed 13, and the reaction gas is taken out of the reactor outlet 15.

(Conditions of Reaction Step)

In the method for converting ethanol according to the present embodiment, the reaction temperature may be 300 °C. or higher. Because of the presence of thermal equilibrium in a produced olefin, the reaction temperature is preferably 450 °C. or higher in view of higher improvement in a propylene yield. The reaction temperature is preferably lower than 600 °C. in view of suppressing the acceleration of coking deactivation, which is promoted at a high temperature. More specifically, the temperature of the reaction gas at the catalyst bed inlet is preferably 450 °C to 590 °C, and the temperature of the reaction gas at the catalyst outlet is preferably 450 °C to 590 °C.

The temperature difference between the catalyst bed outlet temperature and the catalyst bed inlet temperature is preferably −70 K to 70 K, more preferably −60 K to 60 K.

The catalyst bed inlet temperature is the temperature of the raw material mixture immediately before the raw material fluid comes into contact with the catalyst bed filled into the adiabatic reactor. The catalyst bed outlet temperature is the temperature of the reaction gas immediately after the reaction gas passes through the catalyst bed. In this context, the temperatures of the raw material mixture and the reaction gas refer to temperatures at 0 d to 0.8 d, wherein d represents the distance from the center of the reactor to the inner wall surface of the reactor when the center of the reactor in a plane perpendicular to the flow direction of a fluid is defined as 0. The inlet-outlet average reaction temperature (hereinafter, also simply referred to as a "reaction temperature") is defined as a value calculated according to the expression: [Catalyst bed inlet temperature+Catalyst bed outlet temperature]/2, wherein the catalyst bed inlet temperature and the catalyst bed outlet temperature are measured, as shown in FIG. 1.

The reaction pressure is preferably in the range of 0.01 to 3.0 MPaG, more preferably in the range of 0.01 to 1.0 MPaG.

The feed rate of the effective raw material is preferably 0.1 to 1000 $hr^{-1}$, more preferably 0.1 to 500 $hr^{-1}$, further preferably 0.5 to 100 $hr^{-1}$, in terms of the weight hourly space velocity (WHSV) of a catalyst. In the method for converting ethanol according to the present embodiment, WHSV is calculated by converting ethanol to ethylene as shown in the expression given below. The mass flow rate of the effective raw material fed is preferably 1 kg/hr or more, more preferably 10 kg/hr or more, further preferably 1 t/hr or more, in view of excellent productivity of a target compound such as propylene or an aromatic compound.

$$WHSV\ (\text{hr}^{-1}) = \text{Mass flow rate of effective raw material fed (kg/hr)/Amount (kg) of catalyst}$$

$$\text{Mass flow rate of effective raw material fed (kg/hr)} = \text{Methanol flow rate in terms of methylene (kg/hr)} + \text{Ethanol flow rate in terms of ethylene (kg/hr)} + \text{Flow rate (kg/hr) of olefin having 4 to 6 carbon atoms} + \text{Ethylene flow rate (kg/hr)} + \text{Flow rate (kg/hr) of oxygenate having 1 to 6 carbon atoms other than ethanol}$$

$$\text{Methanol flow rate in terms of methylene (kg/hr)} = \text{Methanol flow rate (kg/hr)} \times 0.438$$

$$\text{Ethanol flow rate in terms of ethylene (kg/hr)} = \text{Ethanol flow rate (kg/hr)} \times 0.609$$

(Catalyst)

In the method for converting ethanol according to the present embodiment, the catalyst is a solid catalyst that exhibits the ability to catalyze the conversion of an olefin, methanol, and ethanol to a target compound such as propylene and an aromatic compound. Such a catalyst is preferably a zeolite-containing catalyst in view of excellent thermal durability of the catalyst and propylene selectivity. A common challenge to conventional olefin production involving use of zeolite is coking deactivation caused by a heavy carbonaceous material (coke) that accumulates inside zeolite pores through reaction with a hydrocarbon and deactivates the zeolite. For regenerating catalyst performance, it is necessary to remove coke by combustion in an atmosphere containing an oxygen molecule. In association with this combustion of coke, however, structural collapse of zeolite proceeds to induce permanent deterioration of the catalyst impossible to regenerate. According to the method for converting ethanol according to the present embodiment, the zeolite-containing catalyst used easily maintains its activity because the production of coke can be suppressed.

<<Zeolite-Containing Catalyst>>

The zeolite-containing catalyst is a catalyst powder or compact containing zeolite as an active species. In the method for converting ethanol according to the present embodiment, so-called medium pore-size zeolite, which has a pore size of 5 to 6 angstroms, is preferably used as zeolite in the zeolite-containing catalyst described above. The medium pore-size zeolite means "zeolite whose pore size range is in between the pore size of small pore-size zeolite typified by type A zeolite and the pore size of large pore-size zeolite typified by mordenite or type X or Y zeolite". The "medium pore-size zeolite" has a so-called oxygen 10-membered ring in its crystal structure.

Examples of the medium pore-size zeolite include ZSM-5, ZSM-8, ZSM-11, ZSM-12, ZSM-21, ZSM-23, ZSM-35, and ZSM-38. Among them, ZSM-5-type zeolite such as ZSM-5, ZSM-11, or ZSM-8, or ZSM-38 is preferred. Alternatively, zeolite similar to ZSM-5 or ZSM-11 described in Stud. Surf. Sci. Catal. 1987, 33, 167-215 can be used. Among them, MFI-type zeolite is preferred, and ZSM-5 is more preferred, in view of excellent catalyst performance (catalytic activity and durability against coking).

The silica/alumina ($SiO_2/Al_2O_3$) molar ratio of zeolite contained in the zeolite-containing catalyst of the present embodiment can be appropriately selected and is preferably 20 to 2000 in view of excellent catalytic activity and selectivity, and more preferably 100 to 1500, further preferably 300 to 1200, still further preferably 800 to 1200, in view of enhancing the durability of the catalyst. The silica/alumina ($SiO_2/Al_2O_3$) molar ratio of zeolite contained in the zeolite-containing catalyst may be 20 to 400 or may be 100 to 300. The silica/alumina molar ratio of zeolite can be measured by a known method and can be determined, for example, by completely dissolving the zeolite in an aqueous alkali solution, and analyzing the resulting solution by plasma emission spectroscopy or the like.

A method for synthesizing the zeolite of the present embodiment is not particularly limited, and the zeolite can be produced by optimizing various conditions for a conventionally known hydrothermal synthesis method of MFI-type zeolite. In general, an approach of efficiently obtaining MFI-type zeolite by a hydrothermal synthesis method includes a method including hydrothermally synthesizing the zeolite with an appropriate organic structure-directing agent (SDA), a method including hydrothermally synthesizing the zeolite by adding hydrothermally synthesized MFI zeolite as seed crystals, or a method including hydrothermally synthesizing the zeolite by adding a seed slurry at a crystalline stage. In this context, examples of the organic structure-directing agent (SDA) used include ammonium salts, urea compounds, amine, and alcohols. Not only organic SDA but an inorganic cation or anion is known to be structurally involved, and the zeolite synthesis depends on complex work of individual components. The hydrothermal synthesis method of MFI-type zeolite as mentioned above can produce a suitable catalyst by appropriately optimizing synthesis conditions such as the type of a raw material or an additive (SDA), the amount of the additive, pH, a silica/alumina molar ratio, a medium, raw material charging composition (e.g., the abundance ratio of a cation or an anion), a synthesis temperature, and a synthesis time.

Specific examples thereof include a synthesis method involving use of a seed slurry described in Japanese Patent No. 5426983, and methods illustrated in The Hydrothermal Synthesis of Zeolites (Chemical Reviews, 2003, 103, 663-702).

Commercially available zeolite may be used as long as the zeolite is the aforementioned MFI zeolite having specific physical properties and composition.

The zeolite-containing catalyst according to the present embodiment preferably comprises a phosphorus element or a silver element.

Examples of the form of the phosphorus element include phosphorus polymers (e.g., polyphosphoric acid), phosphorus oxides (e.g., $P_2O_5$), and compounds having phosphorus added to aluminum of zeolite. A plurality thereof may be contained. The phosphorus element is effective for suppressing dealumination of zeolite when the zeolite contains aluminum, or is effective for improving a propylene yield of propylene production reaction in some cases. In the method according to the present embodiment, water may be produced in a reactor through dehydration reaction of an alcohol and contained in methanol and ethanol as the raw material. Therefore, a high-temperature water vapor atmosphere is easily created in the reactor, and the characteristics of the zeolite-containing catalyst are easily changed by dealumination. However, the effect of suppressing dealumination of zeolite is more improved when the zeolite-containing catalyst contains the phosphorus element.

The content of the phosphorus element contained in the zeolite-containing catalyst is preferably 0.01 to 2.0% by mass based on the mass of the whole catalyst, and is more preferably 0.05 to 2.0% by mass in view of the excellent effect of suppressing dealumination.

In the present embodiment, the content of the phosphorus element in the catalyst refers to a value found using an X-ray fluorescence analyzer. The content of the phosphorus element can be measured using a commercially available X-ray fluorescence analyzer under usual conditions in accordance with its instruction manual. In the case of using, for example, trade name "RIX3000" manufactured by Rigaku Corp., measurement conditions can involve a tube voltage of 50 kV and a tube current of 50 mA using P-Kα ray.

In the present embodiment, phosphoric acid and/or phosphate (hereinafter, also referred to as a "phosphorus raw material") is used as a raw material for the phosphorus element contained in the zeolite-containing catalyst. The phosphorus raw material is more preferably phosphate, and the phosphate is more preferably a compound having a solubility of 1 g or more in 100 g of water at 25 °C.

Examples of the phosphoric acid include phosphoric acid and pyrophosphoric acid. Examples of the phosphate include phosphoric acid ammonium salts such as ammonium phosphate, diammonium hydrogen phosphate, ammonium dihydrogen phosphate, and ammonium sodium hydrogen phosphate, potassium hydrogen phosphate, aluminum hydrogen phosphate, sodium phosphate, and potassium phosphate. Among them, a phosphoric acid ammonium salt having a relatively high solubility in water is preferred, and at least one member selected from the group consisting of ammonium phosphate, diammonium hydrogen phosphate, and ammonium dihydrogen phosphate is more preferred. These compounds may each be used singly or may be used in combination of two or more.

The form of the silver element is, for example, a silver ion. The silver element is effective for controlling the acid site of zeolite, thereby improving the hydrothermal resistance of the zeolite.

The content of the silver element contained in the zeolite-containing catalyst is preferably 0.01 to 2.0% by mass based on the mass of the whole catalyst, and is more preferably 0.05 to 2.0% by mass in view of the excellent effect of improving hydrothermal resistance per content.

In the present embodiment, the content of the silver element in the catalyst refers to a value found using a X-ray fluorescence analyzer. The content of the silver element can be measured using a commercially available X-ray fluorescence analyzer under usual conditions in accordance with its instruction manual. In the case of using, for example, trade name "RIX3000" manufactured by Rigaku Corp., measurement conditions can involve a tube voltage of 50 kV and a tube current of 50 mA using P-Kα ray.

In the present embodiment, silver nitrate is used as a raw material for the silver element contained in the zeolite-containing catalyst. A zeolite-containing catalyst containing sodium as a counter cation is used in ion exchange with silver nitrate and the resultant is sintered to obtain a zeolite-containing catalyst containing a silver element. The ion exchange of sodium serving as a counter cation in zeolite with silver nitrate can be carried out by dipping the zeolite or the zeolite-containing catalyst in an aqueous solution of silver nitrate, followed by washing with water. In this respect, the ion exchange rate can be improved by carrying out the dipping and the washing with water a plurality of times.

The zeolite-containing catalyst of the present embodiment can be produced by using the aforementioned zeolite having specific physical properties and composition, and molding the zeolite, for example, as described below. The molding method is not particularly limited, and a general method can be used. Specific examples thereof include a method including compression-molding a catalytic component, a method including extrusion-molding a catalytic component, and a spray dry molding method optimal for a fluidized-bed reaction scheme.

A binder can be used in the molding. The binder is not particularly limited, and, for example, silica, alumina, and kaolin can each be used alone or can be used as a mixture. Commercially available products can be used as these binders. The mass ratio of zeolite/binder is preferably in the range of 10/90 to 90/10, more preferably in the range of 20/80 to 80/20. A silica binder is preferred in view of suppression of coking.

In the method for converting ethanol according to the present embodiment, the zeolite-containing catalyst may be subjected to a pretreatment step prior to contacting the raw material with the zeolite-containing catalyst. The pretreatment step is preferably a heat treatment step at a temperature of 300 °C. or higher in the presence of water vapor. The pretreatment tends to more remarkably produce the effect of suppressing the deterioration of the catalyst or improving selectivity. In the case of the method described above, the treatment is preferably performed at a temperature of 300 °C. or higher and 900 °C. or lower in an atmosphere of, but not particularly limited to, a mixed gas of air or an inert gas (such as nitrogen) and steam (water vapor) circulated under conditions involving a water vapor partial pressure of 0.01 atm or more. The heat treatment temperature is more preferably a temperature of 400 °C. or higher and 700 °C. or lower. This pretreatment step can be performed using a reactor for converting alcohol.

(Product: Reaction Gas Comprising Olefin Having 3 or More Carbon Atoms)

In the method for converting ethanol according to the present embodiment, the raw material mixture is contacted with the catalyst to obtain a reaction gas comprising an olefin having 3 or more carbon atoms. The "reaction gas"

means a gas composition after reaction caused by the contact of the raw material mixture with the catalyst. The reaction gas may comprise ethylene. The reaction gas may comprise hydrogen, an aliphatic hydrocarbon having 1 to 3 carbon atoms, an aliphatic hydrocarbon having 4 to 8 carbon atoms, an aromatic compound, and a hydrocarbon having 9 or more carbon atoms.

Herein, an aliphatic hydrocarbon having 1 to 3 carbon atoms, an aliphatic hydrocarbon having 4 to 8 carbon atoms, an aromatic compound, and a hydrocarbon having 9 or more carbon atoms are referred to as target compounds.

[Regeneration Step]

When a catalyst is used in reaction for a long period, coke may be deposited onto the catalyst, causing coking deactivation. If the catalyst has undergone coking deactivation, for example, coke on the catalyst can be contacted with an oxygen-containing gas and removed by combustion at a temperature of 400 to 700 °C to regenerate the catalyst that has undergone coking deactivation (hereinafter, also referred to as a "regeneration step"). Examples of the oxygen-containing gas include air and a mixed gas of air or oxygen and an inert gas. The oxygen concentration of the oxygen-containing gas is preferably 0.1 to 2.0% by volume. For the catalyst, any regeneration method may be adopted, including extra-reactor regeneration, which involves discharging the catalyst from the reactor and performing regeneration treatment outside the reactor, and intra-reactor regeneration, which involves performing regeneration treatment inside the reactor without discharging the catalyst from the reactor. Alternatively, reaction-regeneration switching operation may be performed by adopting a switchable reactor.

(Reaction-Regeneration Switching Operation)

The reaction-regeneration switching operation is an operational procedure of performing the reaction step and the regeneration step at the same time using a double-column or multi-column switchable adiabatic reactor. In the case of, for example, a triple-column switchable reactor, two columns are used in the reaction step while the remaining one column is used in the catalyst regeneration. Then, the reaction step of one of the columns used in the reaction step is terminated, and the catalyst regeneration is performed instead. The reaction step is performed in the one column used in the catalyst regeneration. As a result, the catalyst regeneration can be performed while production capacity derived from two columns is maintained. Such a reaction format, also called merry-go-round scheme, is preferred in view of production efficiency because of the absence of the need of discontinuing the production process for catalyst regeneration.

[Separation Step]

In a separation step, a target compound is separated from the reaction gas. By the separation step, ethylene, propylene, and an aromatic compound can be separated from the reaction gas.

The method according to the present embodiment can be carried out by an apparatus having reactor 1, distillation column 2, distillation column 3, and distillation column 4, as shown in FIG. 2. The reaction gas obtained by the reaction step performed in the reactor 1 can be separated into fraction A mainly containing a hydrocarbon having 1 to 3 carbon atoms and fraction B mainly containing a hydrocarbon having 4 to 8 carbon atoms by the distillation column 2. Before distillation in the distillation column 2, condensed water may be removed from the reaction gas (not shown). In the distillation column 3 and the distillation column 4, the separation of ethylene and propylene from the reaction gas is efficiently performed by separating ethylene and propylene from the fraction A. At least a portion of the reaction gas and/or the fraction A may be introduced to the refining system of an ethylene plant, and ethylene and propylene can be separated from the reaction gas by the refining system. Various fractions including the fraction B obtained by the separation step can be recycled as a raw material to the reactor.

The method according to the present embodiment can be carried out by an apparatus having reactor 1, distillation column 2, and steam cracking apparatus 5, as shown in FIG. 3. The fraction B obtained by the separation step is subjected to steam cracking to obtain a steam cracking product containing ethylene and propylene. The efficiency of the whole process can be enhanced by separating ethylene and propylene from the steam cracking product. The steam cracking means thermal decomposition of a compound in a fraction, together with heating steam.

The method according to the present embodiment can be carried out by an apparatus having reactor 1, cooling apparatus 6, distillation column 2, and oily water separator 7, as shown in FIG. 4. A cooling step can be performed in which the reaction gas obtained by the reaction step performed in the reactor 1 is cooled by the cooling apparatus 6. By the cooling step, the reaction gas can be separated into fraction C mainly containing an aliphatic hydrocarbon having 2 to 6 carbon atoms and fraction D mainly containing water, an aliphatic hydrocarbon having 7 or more carbon atoms, and an aromatic compound. In the cooling step, the fraction C is obtained as a gas component, and the fraction D is recovered as a liquid component. The separation of an aromatic compound from the reaction gas is efficiently performed by separating the aromatic compound from the fraction D.

The fraction D recovered in the cooling step is separated into fraction E mainly containing a hydrocarbon and fraction F mainly containing water by the oily water separator 7. The separation of an aromatic compound from the reaction gas is efficiently performed by separating the aromatic compound from the fraction E. The separation of the aromatic compound is carried out by, for example, distillation, extractive distillation, extraction, crystallization, or a combination thereof.

The method according to the present embodiment can be carried out by an apparatus having reactor 1, distillation column 2, and distillation column 8, as shown in FIG. 5. When the fraction B is recycled by the distillation column 8, it is preferable to separate into fraction B1 mainly containing an aliphatic hydrocarbon, preferably an olefin, having 4 to 6 carbon atoms and fraction B2 mainly containing an aromatic compound and to recycle at least a portion of the fraction B1 to the reactor. The aromatic compound which is not converted to propylene can be removed from the raw material by using, as a recycled raw material, the fraction B1 from which the fraction B2 has been removed. Thus, propylene can be efficiently produced. In this way, the aromatic compound may be separated as the fraction B2 from the fraction B. Further separation and refining of the aromatic compound are carried out by, for example, distillation, extractive distillation, extraction, crystallization, or a combination thereof.

The method according to the present embodiment can be carried out by an apparatus having reactor 1, distillation column 2, and distillation column 9, as shown in FIG. 6. it is preferable to separate the fraction B, by the distillation column 9, into fraction B3 mainly containing a hydrocarbon having 4 to 8 carbon atoms and fraction B4 mainly containing a hydrocarbon having 9 or more carbon atoms and to recycle at least a portion of the fraction B3 to the reactor. A heavy material capable of promoting coking deactivation can be removed from the raw material by using, as a recycled raw material, the fraction B3 from which the fraction B4 has been removed. Thus, the coking deactivation of the catalyst can be suppressed.

The term "mainly containing" for various fractions means that the total mass of the component described with the term "mainly containing" exceeds 50% by mass based on each fraction.

These separation steps can be carried out by combining various known methods such as distillation and extraction.

Third Embodiment

Next, the method for converting ethanol according to the third embodiment will be described.

Method for Converting Ethanol

Third Embodiment

The method for converting ethanol according to the present embodiment comprises:

- contacting a raw material mixture containing ethanol and ethylene with a conversion catalyst in an adiabatic reactor to obtain a reaction gas containing an olefin having 3 or more carbon atoms (hereinafter, also referred to as a "reaction step");
- separating the reaction gas into fraction A mainly containing a hydrocarbon having 2 to 3 carbon atoms and fraction B mainly containing a hydrocarbon having 4 to 6 carbon atoms by a first distillation column (hereinafter, also referred to as a "first separation step"); and
- recycling at least a portion of the fraction A as a portion of the raw material mixture to the reaction step (hereinafter, also referred to as a "recycling step").

The present embodiment described above can provide a method for converting ethanol to a target compound in good yield by using an adiabatic reactor and controlling an internal temperature of the reactor.

Propylene can be obtained by separation from the reaction gas mentioned above, and an aromatic compound can also be obtained by separation from the reaction gas mentioned above.

In practical use of a conventional production process of a chemical product, the selection of a reactor and its reaction mode is a factor that largely influences the ease of operation or the size of an environmental load. An adiabatic reactor is an ideal reactor that has no need of heating or cooling the reactor, has a convenient configuration, and has small loads of design, construction, and operation. If a fixed-bed single-stage adiabatic reactor, for example, can be adopted, its advantage is further enhanced. However, the adiabatic reactor has a problem associated with temperature control in a largely endothermic or exothermic reaction system.

Patent Literatures 1 to 3 each disclose a technique of converting each raw material to a target olefin with a zeolite catalyst. However, these techniques cannot be applied to an adiabatic reactor due to large endotherm and exotherm.

Patent Literatures 4 and 5 each disclose a thermal neutralization technique that exploits exothermic reaction involving use of an oxygenate such as an alcohol as a raw material. However, reaction involving use of ethanol, which induces endothermic reaction, as a raw material cannot be carried out in an adiabatic reactor.

When a raw material mixture containing ethanol and ethylene is converted with a catalyst, a reaction gas contains a target compound and also other compounds. A method for converting ethanol and ethylene to a target compound in good yield by effective use of such a compound as a raw material while solving the aforementioned problem associated with temperature control of the reactor will be discussed.

Accordingly, an object of the present invention is to provide a method for converting ethanol, comprising converting ethanol and ethylene to a target compound in good yield, a method for producing propylene, and a method for producing an aromatic compound, and an apparatus for converting ethanol and ethylene, by using an adiabatic reactor and controlling an internal temperature of the reactor.

The present inventors have conducted diligent studies to attain the object described above, and consequently found that heat of reaction for the conversion of ethanol and ethylene to an olefin having 3 or more carbon atoms, etc. can be controlled by subjecting a reaction gas obtained by the conversion of ethanol and ethylene to a separation step, followed by recycling to the reaction step, and ethanol and ethylene can be converted to a target compound in good yield by using an adiabatic reactor while controlling an internal temperature of the reactor.

The present embodiment can provide a method for converting ethanol, comprising converting ethanol to a target compound in good yield, a method for producing propylene, and a method for producing an aromatic compound, and an apparatus for converting ethanol and ethylene, by using an adiabatic reactor and controlling an internal temperature of the reactor.

<Reaction Step>

In the reaction step according to the present embodiment, a raw material mixture containing ethanol and ethylene is contacted with a catalyst in an adiabatic reactor to obtain a reaction gas containing an olefin having 3 or more carbon atoms. According to the present embodiment, an environmentally friendly conversion method having a small load of operation and high energy efficiency can be carried out by using an adiabatic reactor. Even in the case of using an adiabatic reactor, ethanol and ethylene can be converted to a target compound in good yield by a recycling step mentioned later, and the coking deactivation of a catalyst can be suppressed. Therefore, the method of the present embodiment is suitable as a method for converting ethanol.

The present inventors have gained the finding that in an attempt to produce propylene in an adiabatic reactor using ethylene or ethanol alone as a raw material, the yield of propylene is decreased, or the coking deactivation of a catalyst proceeds. The coking deactivation of a catalyst means that coke is deposited on catalyst surface to reduce the activity of the catalyst.

On the basis of such a finding, the present inventors have found that when a raw material mixture containing ethylene and ethanol is contacted with a catalyst filled into an adiabatic reactor, propylene can be provided in good yield and coking deactivation can be suppressed.

This is presumably because thermal neutralization can be achieved by combining endothermic reaction and exothermic reaction that do not inhibit each other. The conversion of ethylene to propylene is exothermic reaction. The conversion of ethanol to propylene is endothermic reaction based on two-stage reaction, the dehydration of ethanol to ethylene and the conversion of ethylene to propylene, in the presence of a catalyst. The conversion of ethylene to propylene and the conversion of ethanol to propylene have been found to proceed without inhibiting each other, and the combination of the exothermic reaction and the endothermic reaction has presumably enabled reaction conditions to be controlled even for an adiabatic reactor in the present embodiment. However, the cause is not limited thereto.

(Raw Material)

The method for converting ethanol according to the present embodiment employs a raw material mixture containing ethylene and ethanol. By use of the raw material mixture, a target compound such as propylene can be produced in good yield by using an adiabatic reactor and controlling an internal temperature of the reactor. Ethanol is preferably derived from biomass in view of excellent environmental friendliness. The biomass refers to an organic resource other than a fossil resource originating from an animal or a plant. The term "derived from biomass" refers to a compound produced by using the biomass as a raw material.

Ethylene contained in the raw material mixture is fed by recycling, as a raw material, a portion or the whole amount of ethylene contained in a fraction separated from the reaction gas. In this way, effective use of a raw material can be achieved by using a so-called recycling reaction system.

The raw material mixture can further comprise "additional ethylene" in addition to ethylene contained in a fraction separated from the reaction gas, in view of excellent variability of a raw material ratio. Ethylene produced by any of various production methods can be used as the "additional ethylene". For example, ethylene obtained through thermal cracking of naphtha and/or ethane, direct or oxidative dehydrogenation reaction of ethane, or dehydration reaction of ethanol can be used.

Such ethylene and ethanol often undergo a process in which water is produced as a by-product or coexists in a reactor in their production process. Thus, in the conversion method of the present embodiment, the raw material ethylene and ethanol may contain water.

The molar ratio of ethylene/ethanol in the raw material mixture is preferably 0.20 to 2.5, more preferably 0.20 to 2.0, further preferably 0.30 to 1.5, particularly preferably 0.30 to 1.0, in view of converting ethanol to a target compound in good yield by controlling an internal temperature of the reactor.

In the method for converting ethanol according to the present embodiment, the raw material mixture may further comprise methanol. Methanol produced by any of various production methods can be used. For example, methanol obtained through hydrogenation of carbon monoxide obtained from a natural gas or coal, hydrogenation of carbon dioxide, or distillation of pyroligneous acid can be used.

In the method for converting ethanol according to the present embodiment, the raw material mixture may further comprise an olefin having 4 to 6 carbon atoms. The olefin having 4 to 6 carbon atoms can provide a target compound such as propylene by contact with a catalyst, as in ethylene and ethanol. Examples of the olefin having 4 to 6 carbon atoms include butene, pentene, and hexene. Herein, the term "olefin" includes linear, branched, and cyclic olefins as well as cycloparaffin.

The molar ratio of olefin having 4 to 6 carbon atoms/ethylene in the raw material mixture is preferably 3.0 or less, more preferably 1.0 or less, further preferably 0.5 or less, further preferably 0.15 to 0.5.

In the method for converting ethanol according to the present embodiment, the raw material mixture may further comprise an oxygenate having 1 to 6 carbon atoms other than ethanol. The oxygenate having 1 to 6 carbon atoms can provide a target compound such as propylene by contact with a catalyst, as in ethylene and ethanol. Examples of the oxygenate having 1 to 6 carbon atoms other than ethanol include methanol, propanol, dimethyl ether, and diethyl ether.

The molar ratio of oxygenate having 1 to 6 carbon atoms other than ethanol/ethanol in the raw material mixture is preferably 1.0 or less, more preferably 0.5 or less.

Ethylene, ethanol, an olefin having 4 to 6 carbon atoms, and an oxygenate having 1 to 6 carbon atoms other than ethanol are also collectively referred to as an "effective raw material".

The raw material mixture may comprise, in addition to the effective raw material described above, a saturated aliphatic hydrocarbon such as paraffin, an olefin having 7 or more carbon atoms, and an oxygenate having 7 or more carbon atoms. The saturated aliphatic hydrocarbon, the olefin having 7 or more carbon atoms, and the oxygenate having 7 or more carbon atoms are capable of being converted to a target compound by contact with a catalyst, as in ethylene and ethanol, though their reactivity is lower than that of the effective raw material mentioned above.

The raw material mixture may comprise an inert gas such as nitrogen, in addition to the aforementioned raw material capable of being converted to propylene by the reaction step. In addition, the raw material mixture may comprise hydrogen or methane as a dilution gas. It is however preferred to not dilute with hydrogen. Although hydrogen may be used for suppressing the coking deactivation of a catalyst, hydrogen also causes hydrogenation of produced propylene or the like, which has an adverse effect of reducing propylene purity (propylene/(propylene+propane)) [mol/mol]. The method of the present embodiment has a small coking deactivation rate of a catalyst and permits stable operation even if dilution with hydrogen is not performed. Therefore, it is preferred to not dilute with hydrogen.

The total proportion of ethylene, an olefin having 4 to 6 carbon atoms, and ethanol in the raw material mixture is preferably 40% by mass or more, more preferably 50% by mass or more, based on a mass flow rate of the raw material mixture fed. The mass flow rate of the raw material mixture fed is the total flow rate of all compounds to be fed into a reactor, including an inert component.

The total content of ethylene and ethanol in the raw material mixture is preferably 30 to 100% by mass, more preferably 40 to 100% by mass, further preferably 50 to 100% by mass, based on the mass of the effective raw material fed. Here, as for ethanol, the mass thereof in terms of ethylene is used in the calculation of the mass of ethanol and the mass of the effective raw material fed.

The total content of olefins having 4 to 6 carbon atoms in the raw material mixture is preferably 65% by mass or less, more preferably 10 to 55% by mass, based on the mass of the effective raw material fed.

In the method for converting ethanol according to the present embodiment, the raw material mixture may comprise water. Ethylene and ethanol contained in the raw material mixture are produced by various production methods and may therefore contain "water generated in the production process". In this context, the "water generated in the production process" refers to moisture that is generated in an ethylene and/or ethanol production process and remains unremoved.

In the method for converting ethanol according to the present embodiment, the raw material mixture may comprise water vapor in addition to the "water generated in the production process". The water vapor is effective for decreasing an olefin partial pressure, thereby suppressing coking deactivation and improving the yield of a lower olefin. On the other hand, the water vapor might promote dealumination of zeolite. Therefore, preferably, the raw material mixture comprises no water vapor in addition to the "water generated in the production process".

(Adiabatic Reactor)

A feature of the method for converting ethanol according to the present embodiment is to employ an adiabatic reactor. For the adiabatic reactor, see the description of Adiabatic Fixed-Bed Reactors (Elsevier, 2014, Ch. 1, P. 4, L. 5-24, ISBN:978-0-12-801306-9). Examples of the adiabatic reactor include fixed-bed adiabatic reactors, moving-bed adiabatic reactors, and fluidized-bed adiabatic reactors. In the method of the present embodiment, a fixed-bed adiabatic reactor is preferred. The fixed-bed adiabatic reactor is more preferably a fixed-bed single-stage adiabatic reactor, which has a single stage of a fixed catalyst bed. Since a carbonaceous material (coke) is deposited on a catalyst in association with reaction, a multi-column switchable fixed-bed single-stage adiabatic reactor, which is capable of removing this carbonaceous material by combustion while continuing the reaction is preferred.

FIG. 1 is a schematic view of the configuration of the fixed-bed single-stage adiabatic reactor. Fixed-bed single-stage adiabatic reactor 1 has reaction housing 12 having heat insulation material 121 provided on its outer periphery, catalyst bed 13, reactor inlet 14, and reactor outlet 15. The reaction housing 12, which has the heat insulation material 121 provided on its outer periphery, does not allow the internal heat of the reactor to escape to the outside. In the production method according to the present embodiment, the internal temperature of the reactor can be controlled through exothermic and endothermic reactions.

The catalyst bed 13 is filled with a catalyst mentioned later. First sheathed thermocouple 161 is disposed immediately upstream of catalyst bed inlet 131 of the catalyst bed 13. Second sheathed thermocouple 162 is disposed immediately downstream of catalyst bed outlet 132 of the catalyst bed 3. These thermocouples measure the temperatures of the raw material mixture immediately before contact with the catalyst bed inlet 131 and the reaction gas immediately after passage through the catalyst bed outlet 132. The catalyst bed 13 may be of multi-column type and is preferably of single-stage type as shown in FIG. 1.

In the fixed-bed single-stage adiabatic reactor 1, the raw material mixture is introduced from the reactor inlet 14 and contacted with the catalyst bed 13, and the reaction gas is taken out of the reactor outlet 15.

(Conditions of Reaction Step)

In the method for converting ethanol according to the present embodiment, the reaction temperature may be 300 °C. or higher. Because of the presence of thermal equilibrium in a produced olefin, the reaction temperature is preferably 450 °C. or higher in view of higher improvement in a propylene yield. The reaction temperature is preferably lower than 600 °C. in view of suppressing the acceleration of coking deactivation, which is promoted at a high temperature. More specifically, the temperature of the reaction gas at the catalyst bed inlet is preferably 450 °C to 590 °C, and the temperature of the reaction gas at the catalyst outlet is preferably 450 °C to 590 °C.

The temperature difference between the catalyst bed outlet temperature and the catalyst bed inlet temperature is preferably −80 K to 80 K, more preferably −60 K to 60 K.

The catalyst bed inlet temperature is the temperature of the raw material mixture immediately before the raw material fluid comes into contact with the catalyst bed filled into the adiabatic reactor. The catalyst bed outlet temperature is the temperature of the reaction gas immediately after the reaction gas passes through the catalyst bed. In this context, the temperatures of the raw material mixture and the reaction gas refer to temperatures at 0 d to 0.8 d, wherein d represents the distance from the center of the reactor to the inner wall surface of the reactor when the center of the reactor in a plane perpendicular to the flow direction of a fluid is defined as 0. The inlet-outlet average reaction temperature (hereinafter, also simply referred to as a "reaction temperature") is defined as a value calculated according to the expression: [Catalyst bed inlet temperature+Catalyst bed outlet temperature]/2, wherein the catalyst bed inlet temperature and the catalyst bed outlet temperature are measured, as shown in FIG. 1.

The reaction pressure is preferably in the range of 0.01 to 3.0 MPaG, more preferably in the range of 0.01 to 1.0 MPaG.

The feed rate of the effective raw material is preferably 0.1 to 1000 $hr^{-1}$, more preferably 0.1 to 500 $hr^{-1}$, further preferably 0.5 to 100 $hr^{-1}$, in terms of the weight hourly space velocity (WHSV) of a catalyst. In the method for converting ethanol according to the present embodiment, WHSV is calculated by using an ethanol flow rate in terms of ethylene as shown in the expression given below. The mass flow rate of the effective raw material fed is preferably 1 kg/hr or more, more preferably 10 kg/hr or more, further preferably 1 t/hr or more, in view of being excellent in the productivity of a target compound.

$$WHSV\ (\mathrm{hr}^{-1}) = \text{Mass flow rate of effective raw material fed (kg/hr)/Amount (kg) of catalyst}$$

$$\text{Mass flow rate of effective raw material fed (kg/hr)} = \text{Ethylene flow rate (kg/hr)} + \text{Ethanol mass flow rate in terms of ethylene (kg/hr)} + \text{Flow rate (kg/hr) of olefin having 4 to 6 carbon atoms} + \text{Flow rate (kg/hr) of oxygenate having 1 to 6 carbon atoms other than ethanol}$$

$$\text{Ethanol flow rate in terms of ethylene (kg/hr)} = \text{Ethanol flow rate (kg/hr)} \times \text{Molecular weight (g/mol) of ethylene/Molecular weight (g/mol) of ethanol}$$

(Catalyst)

In the method for converting ethanol according to the present embodiment, the catalyst is a solid catalyst that exhibits the ability to catalyze the conversion of an olefin and ethanol to a target compound such as propylene. Such a catalyst is preferably a zeolite-containing catalyst in view of excellent thermal durability of the catalyst. A common challenge to conventional olefin production involving use of zeolite is coking deactivation caused by a heavy carbonaceous material (coke) that accumulates inside zeolite pores through reaction with a hydrocarbon and deactivates the zeolite. For regenerating catalyst performance, it is necessary to remove coke by combustion in an atmosphere containing an oxygen molecule. In association with this combustion of coke, structural collapse of zeolite proceeds to induce permanent deterioration of the catalyst impossible to regenerate. According to the method for converting ethanol according to the present embodiment, the zeolite-containing catalyst used easily maintains its activity because the production of coke can be suppressed.

<<Zeolite-Containing Catalyst>>

The zeolite-containing catalyst is a catalyst powder or compact containing zeolite as an active species. In the method for converting ethanol according to the present embodiment, so-called medium pore-size zeolite, which has a pore size of 5 to 6 angstroms, is preferably used as zeolite in the zeolite-containing catalyst described above. The medium pore-size zeolite means "zeolite whose pore size range is in between the pore size of small pore-size zeolite typified by type A zeolite and the pore size of large pore-size zeolite typified by mordenite or type X or Y zeolite". The "medium pore-size zeolite" has a so-called oxygen 10-membered ring in its crystal structure.

Examples of the medium pore-size zeolite include ZSM-5, ZSM-8, ZSM-11, ZSM-12, ZSM-21, ZSM-23, ZSM-35, and ZSM-38. Among them, ZSM-5-type zeolite such as ZSM-5, ZSM-11, or ZSM-8, or ZSM-38 is preferred. Alternatively, zeolite similar to ZSM-5 or ZSM-11 described in Stud. Surf. Sci. Catal. 1987, 33, 167-215 can be used. Among them, MFI-type zeolite is preferred, and ZSM-5 is more preferred, in view of excellent catalyst performance (catalytic activity and durability against coking).

The silica/alumina ($SiO_2/Al_2O_3$) molar ratio of zeolite contained in the zeolite-containing catalyst of the present embodiment can be appropriately selected and is preferably 20 to 2000 in view of excellent catalytic activity and selectivity, and more preferably 200 to 1500, further preferably 300 to 1200, still further preferably 800 to 1200, in view of enhancing the durability of the catalyst. The silica/alumina ($SiO_2/Al_2O_3$) molar ratio of zeolite contained in the zeolite-containing catalyst may be 20 to 1200 or may be 150 to 1000. The silica/alumina molar ratio of zeolite can be measured by a known method and can be determined, for example, by completely dissolving the zeolite in an aqueous alkali solution, and analyzing the resulting solution by plasma emission spectroscopy or the like.

A method for synthesizing the zeolite of the present embodiment is not particularly limited, and the zeolite can be produced by optimizing various conditions for a conventionally known hydrothermal synthesis method of MFI-type zeolite. In general, an approach of efficiently obtaining MFI-type zeolite by a hydrothermal synthesis method includes a method including hydrothermally synthesizing the zeolite with an appropriate organic structure-directing agent (SDA), a method including hydrothermally synthesizing the zeolite by adding hydrothermally synthesized MFI zeolite as seed crystals, or a method including hydrothermally synthesizing the zeolite by adding a seed slurry at a crystalline stage. In this context, examples of the organic structure-directing agent (SDA) used include ammonium salts, urea compounds, amine, and alcohols. Not only organic SDA but an inorganic cation or anion is known to be structurally involved, and the zeolite synthesis depends on complex work of individual components. The hydrothermal synthesis method of MFI-type zeolite as mentioned above can produce a suitable catalyst by appropriately optimizing synthesis conditions such as the type of a raw material or an additive (SDA), the amount of the additive, pH, a silica/alumina molar ratio, a medium, raw material charging composition (e.g., the abundance ratio of a cation or an anion), a synthesis temperature, and a synthesis time.

Specific examples thereof include a synthesis method involving use of a seed slurry described in Japanese Patent No. 5426983, and methods illustrated in The Hydrothermal Synthesis of Zeolites (Chemical Reviews, 2003, 103, 663-702).

Commercially available zeolite may be used as long as the zeolite is the aforementioned MFI zeolite having specific physical properties and composition.

The zeolite-containing catalyst according to the present embodiment preferably comprises a phosphorus element or a silver element.

Examples of the form of the phosphorus element include phosphorus polymers (e.g., polyphosphoric acid), phosphorus oxides (e.g., $P_2O_5$), and compounds having phosphorus added to aluminum of zeolite. A plurality thereof may be contained. The phosphorus element is effective for suppressing dealumination of zeolite when the zeolite contains aluminum, or is effective for improving a propylene yield of propylene production reaction in some cases. In the method according to the present embodiment, water may be produced in a reactor through dehydration reaction of an alcohol and contained in the raw material ethanol. Therefore, a high-temperature water vapor atmosphere, which causes dealumination, is easily created in the reactor. The dealumination causes deterioration in activity ascribable to structural collapse of the zeolite-containing catalyst. However, the effect of suppressing dealumination of zeolite is more improved when the zeolite-containing catalyst contains the phosphorus element.

The content of the phosphorus element contained in the zeolite-containing catalyst is preferably 0.01 to 2.0% by mass based on the mass of the whole catalyst, and is more preferably 0.05 to 2.0% by mass in view of the excellent effect of suppressing dealumination.

In the present embodiment, the content of the phosphorus element in the catalyst refers to a value found using an X-ray fluorescence analyzer. The content of the phosphorus element can be measured using a commercially available X-ray fluorescence analyzer under usual conditions in accordance with its instruction manual. In the case of using, for example, trade name "RIX3000" manufactured by Rigaku Corp., measurement conditions can involve a tube voltage of 50 kV and a tube current of 50 mA using P-Kα ray.

In the present embodiment, phosphoric acid and/or phosphate (hereinafter, also referred to as a "phosphorus raw material") is used as a raw material for the phosphorus element contained in the zeolite-containing catalyst. The phosphorus raw material is more preferably phosphate, and the phosphate is more preferably a compound having a solubility of 1 g or more in 100 g of water at 25 °C.

Examples of the phosphoric acid include phosphoric acid and pyrophosphoric acid. Examples of the phosphate include phosphoric acid ammonium salts such as ammonium phosphate, diammonium hydrogen phosphate, ammonium dihydrogen phosphate, and ammonium sodium hydrogen phosphate, potassium hydrogen phosphate, aluminum hydrogen phosphate, sodium phosphate, and potassium phosphate. Among them, a phosphoric acid ammonium salt having a relatively high solubility in water is preferred, and at least one member selected from the group consisting of ammonium phosphate, diammonium hydrogen phosphate, and ammonium dihydrogen phosphate is more preferred. These compounds may each be used singly or may be used in combination of two or more.

The form of the silver element is, for example, a silver ion. The silver element is effective for controlling the acid site of zeolite, thereby improving the hydrothermal resistance of the zeolite.

The content of the silver element contained in the zeolite-containing catalyst is preferably 0.01 to 2.0% by mass based on the mass of the whole catalyst, and is more preferably 0.05 to 2.0% by mass in view of the excellent effect of improving hydrothermal resistance per content.

In the present embodiment, the content of the silver element in the catalyst refers to a value found using an X-ray fluorescence analyzer. The content of the silver element can be measured using a commercially available X-ray fluorescence analyzer under usual conditions in accordance with its instruction manual. In the case of using, for example, trade name "RIX3000" manufactured by Rigaku Corp., measurement conditions can involve a tube voltage of 50 kV and a tube current of 50 mA using P-Kα ray.

In the present embodiment, silver nitrate is used as a raw material for the silver element contained in the zeolite-containing catalyst. A zeolite-containing catalyst containing sodium as a counter cation is used in ion exchange with silver nitrate and the resultant is sintered to obtain a zeolite-containing catalyst containing a silver element. The ion exchange of sodium serving as a counter cation in zeolite with silver nitrate can be carried out by dipping the zeolite or the zeolite-containing catalyst in an aqueous solution of silver nitrate, followed by washing with water. In this respect, the ion exchange rate can be improved by carrying out the dipping and the washing with water a plurality of times.

The zeolite-containing catalyst of the present embodiment can be produced by using the aforementioned zeolite having specific physical properties and composition, and molding the zeolite, for example, as described below. The molding method is not particularly limited, and a general method can be used. Specific examples thereof include a method including compression-molding a catalytic component, a method including extrusion-molding a catalytic component, and a spray dry molding method optimal for a fluidized-bed reaction scheme.

A binder can be used in the molding. The binder is not particularly limited, and, for example, silica, alumina, and kaolin can each be used alone or can be used as a mixture. Commercially available products can be used as these binders. The mass ratio of zeolite/binder is preferably in the range of 10/90 to 90/10, more preferably in the range of 20/80 to 80/20. Among them, a silica binder is preferably used in view of excellent coking resistance.

In the method for converting ethanol according to the present embodiment, the zeolite-containing catalyst may be subjected to a pretreatment step, prior to contacting the raw material with the zeolite-containing catalyst. The pretreatment step is preferably a heat treatment step at a temperature of 300 °C. or higher in the presence of water vapor. The pretreatment tends to more remarkably produce the effect of suppressing the deterioration of the catalyst or improving selectivity. In the case of the method described above, the treatment is preferably performed at a temperature of 300 °C. or higher and 900 °C. or lower in an atmosphere of, but not particularly limited to, a mixed gas of air or an inert gas (such as nitrogen) and steam (water vapor) circulated under conditions involving a water vapor partial pressure of 0.01 atm or more. The heat treatment temperature is more preferably a temperature of 400 °C. or higher and 700 °C. or lower. This pretreatment step can be performed using a reactor for converting ethanol and ethylene.

[Regeneration Step]

The method for converting ethanol according to the present embodiment may comprise the regeneration step of combusting coke deposited on the catalyst (hereinafter, also referred to as a "regeneration step"). When a catalyst is used in reaction for a long period, coke may be deposited onto the catalyst, causing coking deactivation. If the catalyst has undergone coking deactivation, for example, coke on the catalyst can be contacted with an oxygen-containing gas and removed by combustion at a temperature of 400 to 700 °C to regenerate the catalyst that has undergone coking deactivation. Examples of the oxygen-containing gas include air and a mixed gas of air or oxygen and an inert gas. The oxygen concentration of the oxygen-containing gas is preferably 0.1 to 2.0% by volume. For the catalyst, any regeneration method may be adopted, including extra-reactor regeneration, which involves discharging the catalyst from the reactor and performing regeneration treatment outside the reactor, and intra-reactor regeneration, which involves performing regeneration treatment inside the reactor without discharging the catalyst from the reactor. Alternatively, reaction-regeneration switching operation may be performed by adopting a switchable reactor.

(Reaction-Regeneration Switching Operation)

The reaction-regeneration switching operation is an operational procedure of performing the reaction step and the regeneration step at the same time using a double-column or multi-column switchable adiabatic reactor. In the case of, for example, a triple-column switchable reactor, two columns are used in the reaction step while the remaining one column is used in the catalyst regeneration. Then, the reaction step of one of the columns used in the reaction step is terminated, and the catalyst regeneration is performed instead. The reaction step is performed in the one column used in the catalyst regeneration. As a result, the catalyst regeneration can be performed while production capacity derived from two columns is maintained. Such a reaction format, also called merry-go-round scheme, is preferred in view of production efficiency because of the absence of the need of discontinuing the production step for catalyst regeneration.

(Product: Reaction Gas Comprising Olefin Having 3 or More Carbon Atoms)

In the method for converting ethanol according to the present embodiment, the raw material mixture is contacted with the catalyst to obtain a reaction gas comprising an olefin having 3 or more carbon atoms. The "reaction gas" means a gas composition after reaction caused by the contact of the raw material mixture with the catalyst. The reaction gas may comprise ethylene. The reaction gas may comprise hydrogen, an aliphatic hydrocarbon having 1 to 3 carbon atoms, an aliphatic hydrocarbon having 4 to 6 carbon atoms, an aromatic compound, and a hydrocarbon having 9 or more carbon atoms.

Herein, an aliphatic hydrocarbon having 1 to 3 carbon atoms, an aliphatic hydrocarbon having 4 to 6 carbon atoms, an aromatic compound, and a hydrocarbon having 9 or more carbon atoms are referred to as target compounds.

<Separation Step and Recycling Step>

In the separation step according to the present embodiment, the reaction gas obtained in the reaction step mentioned above is separated into fraction A mainly containing a hydrocarbon having 2 to 3 carbon atoms and fraction B mainly containing a hydrocarbon having 4 to 6 carbon atoms by a first distillation column.

Then, in the recycling step, at least a portion of the fraction A is recycled as the raw material mixture to the reaction step.

The recycling means that the whole amount or a portion of a fraction obtained by subjecting the reaction gas to the separation step is subjected again to the reaction step and used as a raw material. In this respect, the fraction to be recycled refers to a recycling fraction. A carbon material derived from ethanol or the like can be efficiently converted to a target compound by subjecting the recycling fraction to the reaction step.

The method according to the present embodiment may be carried out by an apparatus having fixed-bed single-stage adiabatic reactor 1 (hereinafter, also simply referred to as "reactor 1") and first distillation column 2, as shown in FIG. 7. The reaction gas obtained by the reaction step performed in the reactor 1 can be separated into fraction A mainly containing a hydrocarbon having 1 to 3 carbon atoms and fraction B mainly containing a hydrocarbon having 4 to 6 carbon atoms by the first distillation column 2. The separation of ethylene and propylene from the reaction gas is efficiently performed by separating ethylene from the fraction A by a distillation column (not shown) and further separating propylene by a distillation column (not shown). Although not shown, at least a portion of the reaction gas and/or the fraction A may be introduced to the refining system of an ethylene plant, and a target compound such as ethylene or propylene can be separated from the reaction gas by the refining system. At least a portion of the fraction A is recycled as a raw material to the reactor. The fraction B may also be recycled as a raw material to the reactor 1.

The method according to the present embodiment can be carried out by an apparatus having reactor 1, first distillation column 2, and steam cracking apparatus 5, as shown in FIG. 8. The fraction B obtained by the separation step is subjected to steam cracking to obtain a steam cracking product containing ethylene and propylene. The efficiency of the whole process can be enhanced by separating ethylene and propylene from the steam cracking product. The steam cracking means thermal decomposition of a compound in a fraction, together with heating steam.

The method according to the present embodiment can be carried out by an apparatus having reactor 1, cooling apparatus 6, first distillation column 2, and oily water separator 7, as shown in FIG. 9. A cooling step is performed in which the reaction gas obtained by the reaction step performed in the reactor 1 is cooled by the cooling apparatus 6. As a result, the reaction gas can be separated into fraction C mainly containing an aliphatic hydrocarbon having 2 to 6 carbon atoms and fraction D mainly containing water, an aliphatic hydrocarbon having 7 or more carbon atoms, and an aromatic compound. In the cooling step, the fraction C is obtained as a gas component, and the fraction D is recovered as a liquid component. The cooling apparatus used can be a direct heat exchanger which performs heat exchange by directly contacting the reaction gas with a coolant, or an indirect (bulkhead) heat exchanger which performs heat exchange through a wall by circulating the reaction gas and a coolant into spaces separated by the wall.

The fraction C recovered in the cooling step is separated into fraction A mainly containing a hydrocarbon having 1 to 3 carbon atoms and fraction B mainly containing a hydrocarbon having 4 to 6 carbon atoms by the first distillation column 2. At least a portion of the fraction A may be recycled as a portion of the raw material mixture to the reactor 1. In addition, at least a portion of the fraction B may be recycled as a portion of the raw material mixture to the reactor 1.

The fraction D recovered in the cooling step is separated into fraction E mainly containing a hydrocarbon and fraction F mainly containing water by the oily water separator 7. The separation of an aromatic compound from the reaction gas is efficiently performed by separating the aromatic compound from the fraction E. The separation of the aromatic compound is carried out by, for example, distillation, extractive distillation, extraction, crystallization, or a combination thereof.

The method according to the present embodiment can be carried out by an apparatus having reactor 1, cooling apparatus 6, first distillation column 2, and second distillation column 8, as shown in FIG. 10. A cooling step is performed in which the reaction gas obtained by the reaction step performed in the reactor 1 is cooled by the cooling apparatus 6. As a result, the reaction gas can be separated into fraction C mainly containing an aliphatic hydrocarbon having 2 to 6 carbon atoms and fraction D mainly containing water, an aliphatic hydrocarbon having 7 or more carbon atoms, and an aromatic compound. In the cooling step, the fraction C is obtained as a gas component, and the fraction D is recovered as a liquid component. The separation of an aromatic compound from the reaction gas is efficiently performed by separating the aromatic compound from the fraction D recovered in the cooling step. The separation of the aromatic compound is carried out by, for example, distillation, extractive distillation, extraction, crystallization, or a combination thereof. The fraction C obtained in the cooling step is separated into fraction A mainly containing a hydrocarbon having 1 to 3 carbon atoms and fraction B mainly containing a hydrocarbon having 4 to 6 carbon atoms by the first distillation column 2. The fraction A is further fed into the second distillation column 8 so that the fraction A is separated into fraction A-1 mainly containing a hydrocarbon having 2 carbon atoms and fraction A-2 mainly containing a hydrocarbon having 3 carbon atoms. Propylene can be efficiently produced by using the fraction A-1 as a recycled raw material, thereby decreasing a propylene concentration in the raw material mixture.

In the method according to the present embodiment, a side-cut stage may be disposed in a distillation column, as shown in FIG. 11. An intermediately discharged fraction containing a target compound can be obtained through the side-cut stage to improve separation efficiency. The recovery yield of propylene is improved by disposing, in a distillation column, a side-cut stage for discharging fraction E mainly containing a hydrocarbon having 3 carbon atoms from an intermediate portion of the first distillation column 2.

The term "mainly containing" for various fractions means that the total mass of the component described with the term "mainly containing" exceeds 50% by mass based on each fraction. These separation steps can be carried out by combining various known methods such as distillation and extraction.

[Methods for Producing Hydrocarbon, Etc.]

Various chemical products are obtained by separating target compounds from the reaction gases obtained by the first to third embodiments.

In short, the method for producing a hydrocarbon according to the present embodiment comprises contacting a raw material mixture containing ethylene and ethanol with a catalyst in an adiabatic reactor to obtain a reaction gas containing an olefin having 3 or more carbon atoms. The details of the production method are as described for the aforementioned method for converting ethanol, and its preferred embodiments are the same as therein.

Examples of the hydrocarbon obtained by the production method include: aliphatic unsaturated hydrocarbons such as olefins such as propylene, ethylene, butene, pentene, hexene, and heptene, and dienes such as 1,3-butadiene and isoprene; aromatic hydrocarbons such as benzene and toluene; and aliphatic saturated hydrocarbons such as ethane, propane, butane, and pentane. The aromatic hydrocarbons preferably have a boiling point of 500 °C. or lower at normal pressure.

A target hydrocarbon compound can be efficiently refined by introducing the obtained hydrocarbon to a refining system of a cracker.

The method for producing a hydrocarbon according to the present embodiment comprises:

a cracking step of decomposing a hydrocarbon having 2 or more carbon atoms; and a refining step of refining a component obtained in the cracking step, wherein in the refining step, a reaction gas obtained by the aforementioned method for converting ethanol or a refined fraction thereof is combined with the component.

Owing to the constitutional features described above, a target hydrocarbon can be obtained from an ethanol resource using a conventional cracker. For example, a bio-based hydrocarbon can be produced by using bioethanol as a raw material in the method for converting ethanol.

Examples of the hydrocarbon having 2 or more carbon atoms include ethylene, propylene, butene, paraffin, and aromatic hydrocarbons. Naphtha may be used as the hydrocarbon having 2 or more carbon atoms.

A pyrolytic furnace for use in an ethane cracker, a naphtha cracker, or the like may be used as the cracker.

In the refining step, a refining system for use in a conventional ethane cracker or naphtha cracker may be used, and distillation may be performed by a facility equipped with, for example, a distillation column and a quenching column.

The reaction gas obtained by the aforementioned method for converting ethanol or a refined fraction thereof is combined with the component in the refining step mentioned above. The location of combination is appropriately selected depending on the component to be combined therewith.

The method for producing a monomer according to the present embodiment comprises an unsaturated hydrocarbon-separating step of separating a fraction mainly containing an unsaturated hydrocarbon from a reaction gas obtained by the aforementioned method for converting ethanol.

Examples of the unsaturated hydrocarbon include aliphatic unsaturated hydrocarbons such as olefins such as propylene, ethylene, butene, butane, pentene, hexene, and heptene, and dienes such as 1,3-butadiene and isoprene.

The method for producing an olefin according to the present embodiment comprises an olefin-separating step of separating a fraction mainly containing an olefin from a reaction gas obtained by the aforementioned method for converting ethanol.

The method for producing propylene according to the present embodiment comprises a propylene-separating step of separating a fraction mainly containing propylene from a reaction gas obtained by the aforementioned method for converting ethanol.

The method for producing ethylene according to the present embodiment comprises an ethylene-separating step of separating a fraction mainly containing ethylene from a reaction gas obtained by the aforementioned method for converting ethanol.

The method for producing a diene according to the present embodiment comprises a diene-separating step of separating a fraction mainly containing a diene from a reaction gas obtained by the aforementioned method for converting ethanol.

The method for producing a monomer according to the present embodiment may further comprise the step of converting the unsaturated hydrocarbon.

The method for producing an acrylic monomer according to the present embodiment comprises:

an unsaturated hydrocarbon-separating step of separating a fraction mainly containing an unsaturated hydrocarbon from a reaction gas obtained by the aforementioned method for converting ethanol; and an acrylic monomer-producing step of obtaining an acrylic monomer from the unsaturated hydrocarbon obtained by the unsaturated hydrocarbon-separating step.

The acrylic monomer-producing step employs a known method for introducing the acrylic monomer from the unsaturated hydrocarbon.

The method for producing acrylonitrile according to the present embodiment comprises:

a propylene-separating step of separating a fraction mainly containing propylene from a reaction gas obtained by the aforementioned method for converting ethanol; and an acrylonitrile-producing step of obtaining acrylonitrile from the propylene obtained by the propylene-separating step.

The acrylic monomer-producing step employs a known method for introducing the acrylic monomer from the unsaturated hydrocarbon.

The method for producing styrene according to the present embodiment comprises:

an ethylene-separating step of separating a fraction mainly containing ethylene from a reaction gas obtained by the aforementioned method for converting ethanol; and a styrene-producing step of obtaining styrene from the ethylene obtained by the ethylene-separating step.

The monomers obtained by the production methods mentioned above may be further polymerized.

The method for producing a polymer according to the present embodiment comprises the step of polymerizing a monomer obtained by the aforementioned method for producing a monomer.

In the step of polymerizing a monomer, the polymerization can be performed by use of a conventional polymerization method and can be performed with various initiators and polymerization catalysts.

The method for producing an olefin-based polymer according to the present embodiment comprises the step of polymerizing a polymerizable composition comprising an olefin obtained by the aforementioned method for producing an olefin.

In this context, the polymerizable composition may be an olefin alone as a monomer or may contain an additional monomer having an unsaturated bond.

The method for producing a polypropylene-based polymer according to the present embodiment comprises the step of polymerizing a polymerizable composition comprising propylene obtained by the aforementioned method for producing propylene.

In this context, the polymerizable composition may be propylene alone as a monomer or may contain an additional monomer having an unsaturated bond.

The method for producing a polyethylene-based polymer according to the present embodiment comprises the step of polymerizing a polymerizable composition comprising ethylene obtained by the aforementioned method for producing ethylene.

In this context, the polymerizable composition may be ethylene alone as a monomer or may contain an additional monomer having an unsaturated bond.

The method for producing a diene-based polymer according to the present embodiment comprises the step of polymerizing a polymerizable composition comprising a diene obtained by the aforementioned method for producing a diene.

In this context, the polymerizable composition may be a diene alone as a monomer or may contain an additional monomer having an unsaturated bond.

The method for producing an acrylic monomer-based polymer according to the present embodiment comprises the step of polymerizing a polymerizable composition comprising an acrylic monomer obtained by the aforementioned method for producing an acrylic monomer.

In this context, the polymerizable composition may be an acrylic monomer alone as a monomer or may contain an additional monomer having an unsaturated bond.

The method for producing an acrylonitrile-based polymer according to the present embodiment comprises the step of polymerizing a polymerizable composition comprising acrylonitrile obtained by the aforementioned method for producing acrylonitrile.

In this context, the polymerizable composition may be acrylonitrile alone as a monomer or may contain an additional monomer having an unsaturated bond.

The method for producing a styrene-based polymer according to the present embodiment comprises the step of polymerizing a polymerizable composition comprising styrene obtained by the aforementioned method for producing styrene.

In this context, the polymerizable composition may be styrene alone as a monomer or may contain an additional monomer having an unsaturated bond.

An aromatic compound may be separated from the reaction gas obtained by the aforementioned method for converting ethanol.

The method for producing an aromatic compound according to the present embodiment comprises an aromatic compound separation step of separating a fraction mainly containing an aromatic compound from a reaction gas obtained by the aforementioned method for converting ethanol.

Examples of the aromatic hydrocarbon include benzene, toluene, and xylene.

EXAMPLES

Hereinafter, the present invention will be described in more detail with reference to Examples. The present invention is not limited by Examples described below.

[Methods for Measuring Various Physical Properties]

Methods for measuring various physical properties are as described below.

(1) Molar Ratio of Silica/Alumina of Zeolite in Zeolite-Containing Catalyst

Zeolite was completely dissolved in a sodium hydroxide solution to provide a solution. The amounts of Si and Al contained in the solution were measured by an ordinary method using an ICP (inductively coupled plasma) spectrometry apparatus (manufactured by Rigaku Corp., trade name "JY138"), and the molar ratio of silica/alumina was determined from the results. The measurement conditions were set to high-frequency power: 1 kw, plasma gas: 13 L/min, sheath gas: 0.15 L/min, nebulizer gas: 0.25 L/min, Si measurement wavelength: 251.60 nm, and Al measurement wavelength: 396.152 nm.

(2) Phosphorus Element Content and Silver Element Content of Zeolite-Containing Catalyst The contents of a phosphorus element and a silver element in a zeolite-containing catalyst were measured by a routine method using an X-ray fluorescence analyzer (manufactured by Rigaku Corp., trade name "RIX3000").

(3) Structural Type of Zeolite

The structural type of zeolite in a zeolite-containing catalyst was identified by measuring the X-ray diffraction pattern of the zeolite using an X-ray analysis apparatus (manufactured by Rigaku Corp., trade name "RINT"), and referring to the diffraction pattern of known zeolite. The measurement conditions are as follows.

Cu negative electrode

Tube voltage: 40 kV

Tube current: 30 mA

Scan speed: 1 deg/min

[Method for Preparing Zeolite-Containing Catalyst]

(Preparation of Zeolite-Containing Catalyst 1)

Clay obtained from 70 parts by mass of medium pore-size zeolite proton-type ZSM-5 (silica/alumina molar ratio: 200) and 30 parts by mass of silica (whose moisture content was adjusted using colloidal silica and fumed silica) was kneaded, followed by extrusion molding to obtain an extrudate adjusted to a diameter of 1.6 mm and a length of 4 to 6 mm. The obtained extrudate was allowed to support a predetermined amount of an aqueous diammonium hydrogen phosphate solution to obtain a phosphorus-supported product. The obtained phosphorus-supported product was calcined at 600 °C. for 5 hours in an air atmosphere using a calcination furnace. The calcined product was filled into a reactor, and a water vapor-nitrogen mixed gas containing 80% by volume of water vapor was fed and circulated thereinto under conditions involving a pressure of 0.1 MP and a temperature of 600 °C. for 24 hours to obtain zeolite-containing catalyst 1. The content of a phosphorus element contained in the zeolite-containing catalyst was measured and was found to be 0.36% by mass.

(Preparation of Zeolite-Containing Catalyst 2)

Clay obtained from 70 parts by mass of medium pore-size zeolite proton-type ZSM-5 (silica/alumina molar ratio: 980) and 30 parts by mass of silica (whose moisture content was adjusted using colloidal silica and fumed silica) was kneaded, followed by extrusion molding to obtain an extrudate adjusted to a diameter of 2.1 mm and a length of 4 to 6 mm. The obtained extrudate was calcined for 5 hours to obtain zeolite-containing catalyst 2.

(Preparation of Zeolite-Containing Catalyst 3)

Clay obtained from 70 parts by mass of medium pore-size zeolite proton-type ZSM-5 (silica/alumina molar ratio: 980) and 30 parts by mass of silica (whose moisture content was adjusted using colloidal silica and fumed silica) was kneaded, followed by extrusion molding to obtain an extrudate adjusted to a diameter of 2.1 mm and a length of 4 to 6 mm. The obtained extrudate was allowed to support a predetermined amount of an aqueous diammonium hydrogen phosphate solution to obtain a phosphorus-supported product. The obtained phosphorus-supported product was calcined at 600 °C. for 5 hours in an air atmosphere. The calcined product was filled into a reactor, and a water vapor-nitrogen mixed gas containing 80% by volume of water vapor was fed and circulated thereinto under conditions involving a pressure of 0.1 MP and a temperature of 600 °C. for 24 hours to obtain zeolite-containing catalyst 3. In this respect, the content of a phosphorus element contained in the zeolite-containing catalyst was 0.032% by mass.

(Preparation of Zeolite-Containing Catalyst 4)

Clay obtained from 70 parts by mass of medium pore-size zeolite proton-type ZSM-5 (silica/alumina molar ratio: 980) and 30 parts by mass of silica (whose moisture content was adjusted using colloidal silica and fumed silica) was kneaded, followed by extrusion molding to obtain an extrudate adjusted to a diameter of 2.1 mm and a length of 4 to 6 mm. The obtained extrudate was calcined at 600 °C. for 5 hours to obtain a catalyst precursor. The obtained catalyst precursor was stirred for 1 hour in a 0.1 N aqueous sodium nitrate solution, then filtered, washed, and calcined at 600 °C. for 5 hours to obtain a sodium-replaced product. The sodium-replaced product was stirred for 1 hour in a 0.01 N aqueous silver nitrate solution, subjected to filtration and washing three repeated times, and calcined at 600 °C. for 5 hours to obtain a silver-replaced product. A water vapor-air mixed gas containing 80% by volume of water vapor was fed and circulated into the silver-replaced product under conditions involving a pressure of 0.1 MP and a temperature of 600 °C. for 24 hours to obtain zeolite-containing catalyst 2. In this respect, the content of a silver element contained in the zeolite-containing catalyst was 0.16% by mass.

(Preparation of Zeolite-Containing Catalyst 5)

Clay obtained from 70 parts by mass of medium pore-size zeolite proton-type ZSM-5 (silica/alumina molar ratio: 302) and 30 parts by mass of silica (whose moisture content was adjusted using colloidal silica and fumed silica) was kneaded, followed by extrusion molding to obtain an extrudate adjusted to a diameter of 1.6 mm and a length of 4 to 6 mm. The obtained extrudate was calcined at 600 °C. for 5 hours in an air atmosphere to obtain zeolite-containing catalyst 5.

(Preparation of Zeolite-Containing Catalyst 6)

Clay obtained from 70 parts by mass of medium pore-size zeolite proton-type ZSM-5 (silica/alumina molar ratio: 302) and 30 parts by mass of silica (whose moisture content was adjusted using colloidal silica and fumed silica) was kneaded, followed by extrusion molding to obtain an extrudate adjusted to a diameter of 1.6 mm and a length of 4 to 6 mm. The obtained extrudate was allowed to support a predetermined amount of an aqueous diammonium hydrogen phosphate solution to obtain a phosphorus-supported product. The obtained phosphorus-supported product was calcined at 600 °C. for 5 hours in an air atmosphere. The calcined product was filled into a reactor, and a water vapor-nitrogen mixed gas containing 80% by volume of water vapor was fed and circulated thereinto under conditions involving a pressure of 0.1 MP and a temperature of 600 °C. for 24 hours to obtain zeolite-containing catalyst 5. In this respect, the content of a phosphorus element contained in the zeolite-containing catalyst was 0.085% by mass.

Examples of First Embodiment

Hereinafter, the present invention will be described in more detail with reference to Examples of the first embodiment. However, the present invention is not limited by Examples described below.

[Method for Converting Ethanol]

(Reaction Apparatus)

In Examples and Comparative Examples given below, evaluation was conducted using the fixed-bed single-stage adiabatic reactor 1 shown in FIG. 1.

(Raw Material)

The molar ratio of ethylene/ethanol and the molar ratio of olefin having 4 to 6 carbon atoms/ethylene in Examples and Comparative Examples were calculated according to the following expressions.

$$\text{Molar ratio } (-) \text{ of ethylene/ethanol} = \text{Molar flow rate (mol/hr) of ethylene/Molar flow rate (mol/hr) of ethanol}$$

$$\text{Molar ratio } (-) \text{ of ethylene/olefin having 4 to 6 carbon atoms} = \text{Molar flow rate (mol/hr) of ethylene/Flow rate (mol/hr) of olefin having 4 to 6 carbon atoms}$$

(Temperature Measurement)

The temperature of a catalyst bed inlet and the temperature of a catalyst bed outlet were measured by a thermocouple inserted from the outside of the reactor. Specifically, as shown in FIG. 1, temperatures at 0.5 d to 0.6 d were measured, wherein d represents the distance from the center of the reactor to the inner wall surface of the reactor when the center of the reactor in a plane perpendicular to the flow direction of a fluid was defined as 0. The influence of heat dissipation ascribable to the insertion of this thermocouple was negligibly small.

(Evaluation of Reaction)

Reaction was carried out in accordance with Examples and Comparative Examples given below such that an inlet-outlet average reaction temperature was 540 °C. A portion of a gas from the reactor outlet was sampled every 3 hours from the start of the reaction, introduced to a gas chromatograph (hereinafter, also simply referred to as "GC"; TCD and FID detectors), and analyzed for reaction gas composition. The reaction was terminated 48 hours after the start of the reaction. An average value of GC analysis results from the start of the reaction to the termination of the reaction was calculated. The inlet-outlet average reaction temperature was calculated according to the following expression and described as "Reaction temperature" in the tables.

$$\text{Inlet-outlet average reaction temperature (° C.)} = [\text{Catalyst bed inlet temperature (° C.)} + \text{Catalyst bed outlet temperature (° C.)}]/2$$

(Coke Yield)

In Examples and Comparative Examples given below, nitrogen was fed into a reactor after the termination of reaction to purge a hydrocarbon, and a catalyst bed was kept at 500 °C. Subsequently, air/nitrogen having an oxygen concentration of 2% by volume was circulated thereinto to remove coke on the catalyst by combustion. In this respect, a gas from the reactor outlet was regularly sampled as a regeneration gas, and the regeneration gas was analyzed using a gas chromatograph to measure $CO_2$ and CO concentrations. From the resulting values, the amount of carbon deposited on the catalyst was determined, and this amount was regarded as the amount of coke. The method for analyzing the regeneration gas using a gas chromatograph will be described below (Analysis conditions for gas chromatograph). The coke yield in Examples and Comparative Examples given below was determined according to the following expression.

$$\text{Coke yield (ppm by mass)} = \text{Amount of coke}/[\text{Mass flow rate of effective raw material fed (kg/hr)} \times \text{Reaction time (hr)}]$$

$$\text{Mass flow rate of effective raw material fed (kg/hr)} = \text{Ethylene flow rate (kg/hr)} + \text{Ethanol flow rate in terms of ethylene (kg/hr)} + \text{Flow rate (kg/hr) of olefin having 4 to 6 carbon atoms} + \text{Flow rate (kg/hr) of oxygenate having 1 to 6 carbon atoms other than ethanol}$$

$$\text{Ethanol flow rate in terms of ethylene (kg/hr)} = \text{Ethanol flow rate (kg/hr)} \times \text{Molecular weight (g/mol) of ethylene/Molecular weight (g/mol) of ethanol}$$

(Analysis Conditions for Gas Chromatograph)

[Analysis of Regeneration Gas]

Apparatus: GC-8A from Shimadzu Corp.

Column: The following columns (1) and (2) were connected in parallel and used.

Column (1): SUS column (inside diameter: 3 mm, length: 3 m) packed with 80- to 100-mesh molecular sieve 5A (manufactured by FUJIFILM Wako Pure Chemical Corp.)

Column (2): 80- to 100-mesh Porapac-Q (inside diameter: 3 mm, length: 2 m) manufactured by Waters Associates (USA) and SUS resistant column (inside diameter: 3 mm, length: 1 m) connected directly Column temperature: 70 °C.

Carrier gas (helium) flow rate: 60 mL/min

[Analysis of Reaction Gas]

Apparatus: GC-2030 manufactured by Shimadzu Corp.

Column: Custom capillary column SPB-1 (inside diameter: 0.25 mm, length: 60 m, film thickness: 3.0 μm) manufactured by Supelco, Inc. (USA)

Amount of sample gas: 1 mL (a sampling line was kept at 200 °C to 300 °C.)

Heating program: Held at 40 °C. for 12 minutes, subsequently heated to 200 °C. at 5 °C./min, and then held at 200 °C. for 22 minutes.

Split ratio: 200:1

Carrier gas (nitrogen) flow rate: 120 mL/min

FID detector: Air feed pressure of 50 kPa (approximately 500 mL/min), hydrogen feed pressure of 60 kPa (approximately 50 mL/min)

Measurement method: A TCD detector and an FID detector were connected in series. Compositional analysis was conducted on the basis of data on hydrogen detected in the TCD detector and data on oxygenates, such as hydrocarbons and ethanol, detected in the FID detector. The concentration of a target compound in a reaction gas was determined by use of the calibration curve method, and the mass per hour of the compound produced through reaction was determined. Yields were calculated according to the following expressions.

$$\text{Propylene yield (\%)} = \text{Mass per hour of propylene produced through reaction (kg/hr)/Mass flow rate of effective raw material fed (kg/hr)}$$

$$\text{Aromatic yield (\%)} = \text{Mass per hour of aromatic compound produced through reaction (kg/hr)/Mass flow rate of effective raw material fed (kg/hr)}$$

$$\text{Mass flow rate of effective raw material fed (kg/hr)} = \text{Ethylene flow rate (kg/hr)} + \text{Ethanol flow rate in terms of ethylene (kg/hr)} + \text{Flow rate (kg/hr) of olefin having 4 to 6 carbon atoms} + \text{Flow rate (kg/hr) of oxygenate having 1 to 6 carbon atoms other than ethanol}$$

$$\text{Ethanol flow rate in terms of ethylene (kg/hr)} = \text{Ethanol flow rate (kg/hr)} \times \text{Molecular weight (g/mol) of ethylene/Molecular weight (g/mol) of ethanol}$$

Example 1

A raw material mixture gas composed of ethylene, ethanol, and water vapor and having a molar ratio of ethylene/ethanol of 0.37 was heated, fed at WHSV=3.8 into a reactor filled with a zeolite-containing catalyst, and reacted. In this respect, the inlet temperature and the outlet temperature of the catalyst bed were 539 °C. and 542 °C, respectively, and the inlet-outlet average reaction temperature was 540 °C. The average propylene yield and the average aromatic yield from the start of the reaction to the termination of the reaction were 23.2% by mass and 2.7% by mass, respectively. The coke yield of the zeolite-containing catalyst after the completion of 48-hour operation was 270 ppm by mass. The details of reaction results and reaction conditions are shown in Table 1.

Comparative Example 1

The same reaction as in Example 1 was performed except that: an ethanol gas containing neither ethylene nor water vapor was used alone as a raw material gas; and the catalyst bed inlet temperature was adjusted to 588 °C. In this respect, the outlet temperature of the catalyst bed was 492 °C, and the inlet-outlet average reaction temperature was 540 °C. The average propylene yield and the average aromatic yield from the start of the reaction to the termination of the reaction were 19.3% by mass and 1.5% by mass, respectively. The coke yield of the zeolite-containing catalyst after the completion of 48-hour operation was 507 ppm by mass. Reaction results are shown together with reaction conditions in Table 1.

Comparative Example 2

The same reaction as in Example 1 was performed except that: an ethylene gas containing no ethanol was used alone as a raw material gas; and the catalyst bed inlet temperature was adjusted to 450 °C. As a result, the temperature of the catalyst bed outlet still continued to elevate beyond 650 °C. Therefore, the reaction was terminated after a lapse of 1 hour from a safety standpoint. From this Comparative Example, it is found that fiercely exothermic reaction is difficult to carry out efficiently in an adiabatic reactor.

Examples 2 to 6

The same reaction as in Example 1 was performed except that zeolite-containing catalyst 2, zeolite-containing catalyst 3, zeolite-containing catalyst 4, zeolite-containing catalyst 5, and zeolite-containing catalyst 6 were used, respectively. Their respective temperature differences between the inlet and the outlet and reaction results are shown in Table 1.

541 °C, and the inlet-outlet average reaction temperature was 540 °C. The average propylene yield and the average aromatic yield from the start of the reaction to the termination of the reaction were 23.7% by mass and 2.6% by mass, respectively. The coke yield of the zeolite-containing catalyst after the completion of 48-hour operation was 273 ppm by mass. Reaction results are shown together with reaction conditions in Table 3.

TABLE 1

| | | Example 1 | Example 2 | Example 3 | Example 4 | Example 5 | Example 6 | Comp. Ex. 1 | Comp. Ex. 2 |
|---|---|---|---|---|---|---|---|---|---|
| Zeolite-containing catalyst | | 1 | 2 | 3 | 4 | 5 | 6 | 1 | 1 |
| Molar ratio of ethylene/ethanol | | 0.37 | 0.37 | 0.37 | 0.37 | 0.37 | 0.37 | 0.00 | — |
| Ethylene | [kg/hr] | 1.0 | 1.0 | 1.0 | 1.0 | 1.0 | 1.0 | 0.0 | 3.8 |
| Ethanol | [kg/hr] | 4.6 | 4.6 | 4.6 | 4.6 | 4.6 | 4.6 | 6.3 | 0.0 |
| Water vapor (dilution) | [kg/hr] | 0.7 | 0.7 | 0.7 | 0.7 | 0.7 | 0.7 | 0.0 | 2.4 |
| Mass flow rate of raw material mixture fed | [kg/hr] | 6.3 | 6.3 | 6.3 | 6.3 | 6.3 | 6.3 | 6.3 | 6.3 |
| Mass flow rate of effective raw material fed | [kg/hr] | 3.8 | 3.8 | 3.8 | 3.8 | 3.8 | 3.8 | 3.8 | 3.8 |
| Pressure | [MPaG] | 0.15 | 0.15 | 0.15 | 0.15 | 0.15 | 0.15 | 0.15 | 0.15 |
| WHSV | [$hr^{-1}$] | 3.8 | 2.0 | 2.0 | 2.0 | 5.0 | 3.8 | 3.8 | 3.8 |
| Reaction time | [h] | 48 | 48 | 48 | 48 | 48 | 48 | 48 | 1 |
| Reaction temperature | [° C.] | 540 | 540 | 540 | 540 | 540 | 540 | 540 | — |
| Catalyst bed inlet temperature | [° C.] | 539 | 538 | 539 | 538 | 538 | 537 | 588 | 450 |
| Catalyst bed outlet temperature | [° C.] | 542 | 542 | 541 | 542 | 542 | 543 | 492 | — |
| Temperature difference between inlet and outlet | [K] | 3 | 4 | 2 | 4 | 4 | 6 | −96 | — |
| Propylene yield | [% by mass] | 23.2 | 21.2 | 20.2 | 22.5 | 23.5 | 23.2 | 19.3 | — |
| Aromatic yield | [% by mass] | 2.7 | 2.6 | 2.4 | 2.6 | 3.5 | 2.6 | 1.5 | — |
| Coke yield | [ppm by mass] | 270 | 251 | 257 | 240 | 351 | 280 | 507 | — |

The results of Example 1 and Comparative Examples 1 and 2 revealed that use of a raw material mixture having a molar ratio of ethylene/ethanol in a specific range can achieve both of a high propylene yield and suppression of coke deposition on a catalyst.

Example 7

A raw material mixture gas composed of ethylene, ethanol, hydrocarbons having 4 or more carbon atoms mainly containing hydrocarbons having 4 to 8 carbon atoms at the compositional ratio shown in Table 2, and water vapor, and having a molar ratio of ethylene/ethanol and that of olefin having 4 to 6 carbon atoms/ethylene of 0.25 and 0.7, respectively, was heated, fed at WHSV=4.9 into a reactor filled with a zeolite-containing catalyst, and reacted. In this respect, the inlet temperature and the outlet temperature of the catalyst bed were 568 °C. and 512 °C, respectively, and the inlet-outlet average reaction temperature was 540 °C. The average propylene yield and the average aromatic yield from the start of the reaction to the termination of the reaction were 22.5% by mass and 3.0% by mass, respectively. The coke yield of the zeolite-containing catalyst after the completion of 48-hour operation was 315 ppm by mass. The details of reaction results and reaction conditions are shown in Table 3.

Example 8

The same reaction as in Example 7 was performed except that: a raw material mixture gas having a molar ratio of ethylene/ethanol of 0.82 and a molar ratio of olefin having 4 to 6 carbon atoms/ethylene of 0.3 was used; and the inlet temperature of the catalyst bed was adjusted to 539 °C. In this respect, the outlet temperature of the catalyst bed was Example 9

The same reaction as in Example 7 was performed except that: a raw material mixture gas having a molar ratio of ethylene/ethanol of 1.5 and a molar ratio of olefin having 4 to 6 carbon atoms/ethylene of 0.2 was used; and the inlet temperature of the catalyst bed was adjusted to 522 °C. In this respect, the outlet temperature of the catalyst bed was 558 °C, and the inlet-outlet average reaction temperature was 540 °C. The average propylene yield and the average aromatic yield from the start of the reaction to the termination of the reaction were 23.2% by mass and 2.8% by mass, respectively. The coke yield of the zeolite-containing catalyst after the completion of 48-hour operation was 277 ppm by mass. Reaction results are shown together with reaction conditions in Table 3.

Example 10

The same reaction as in Example 7 was performed except that: a raw material mixture gas having an molar ratio of ethylene/ethanol of 2.3 and a molar ratio of olefin having 4 to 6 carbon atoms/ethylene of 0.2 was used; and the inlet temperature of the catalyst bed was adjusted to 511 °C. In this respect, the outlet temperature of the catalyst bed was 569 °C, and the inlet-outlet average reaction temperature was 540 °C. The average propylene yield and the average aromatic yield from the start of the reaction to the termination of the reaction were 22.7% by mass and 2.4% by mass, respectively. The coke yield of the zeolite-containing catalyst after the completion of 48-hour operation was 318 ppm by mass. Reaction results are shown together with reaction conditions in Table 3.

Example 11

The same reaction as in Example 7 was performed except that: a raw material mixture gas having a molar ratio of ethylene/ethanol of 0.25 and a molar ratio of olefin having 4 to 6 carbon atoms/ethylene of 2.00 was used; and the inlet temperature of the catalyst bed was adjusted to 572 °C. In this respect, the outlet temperature of the catalyst bed was 508 °C, and the inlet-outlet average reaction temperature was 540 °C. The average propylene yield and the average aromatic yield from the start of the reaction to the termination of the reaction were 20.4% by mass and 3.9% by mass, respectively. The coke yield of the zeolite-containing catalyst after the completion of 48-hour operation was 320 ppm by mass. Reaction results are shown together with reaction conditions in Table 3.

Comparative Example 3

The same reaction as in Example 7 was performed except that: ethanol and an olefin having 4 to 6 carbon atoms were used as a raw material gas without the use of ethylene; and the inlet temperature of the catalyst bed was adjusted to 590 °C. In this respect, the outlet temperature of the catalyst bed was 490 °C, and the inlet-outlet average reaction temperature was 540 °C. The average propylene yield and the average aromatic yield from the start of the reaction to the termination of the reaction were 17.6% by mass and 1.4% by mass, respectively. The coke yield of the zeolite-containing catalyst after the completion of 48-hour operation was 507 ppm by mass. Reaction results are shown together with reaction conditions in Table 3.

Comparative Example 4

The same reaction as in Example 7 was performed except that: a raw material mixture gas having a molar ratio of olefin having 4 to 6 carbon atoms/ethylene of 0.1 was used without the use of ethanol; and the catalyst bed inlet temperature was adjusted to 477 °C. In this respect, the outlet temperature of the catalyst bed was 603 °C, and the inlet-outlet average reaction temperature was 540 °C. The average propylene yield and the average aromatic yield from the start of the reaction to the termination of the reaction were 16.5% by mass and 1.2% by mass, respectively. The coke yield of the zeolite-containing catalyst after the completion of 48-hour operation was 565 ppm by mass. Reaction results are shown together with reaction conditions in Table 3.

TABLE 2

| | Content (% by mass) |
|---|---|
| Butene | 19.7 |
| Butane | 22.1 |
| Pentene | 10.5 |
| Pentane | 8.3 |
| Hexene | 2.8 |
| Benzene | 2.7 |
| Heptene | 1.0 |
| Toluene | 11.6 |
| Octene | 0.2 |
| Aromatic hydrocarbon having 8 carbon atoms | 15.3 |
| Hydrocarbon having 9 or more carbon atoms | 5.8 |
| Total | 100 |

TABLE 3

| | | Example 7 | Example 8 | Example 9 | Example 10 | Example 11 | Comp. Ex. 3 | Comp. Ex. 4 |
|---|---|---|---|---|---|---|---|---|
| Zeolite-containing catalyst | | 1 | 1 | 1 | 1 | 1 | 1 | 1 |
| Molar ratio of ethylene/ethanol | | 0.25 | 0.82 | 1.5 | 2.3 | 0.25 | 0.00 | — |
| Molar ratio of olefin having 4 to 6 carbon atoms/ethylene | | 0.7 | 0.3 | 0.2 | 0.2 | 2.00 | 0.00 | 0.1 |
| Ethylene | [kg/hr] | 0.8 | 1.7 | 2.3 | 2.7 | 0.3 | 0.0 | 3.8 |
| Ethanol | [kg/hr] | 5.0 | 3.4 | 2.5 | 1.9 | 1.7 | 6.3 | 0.0 |
| Hydrocarbon having 4 or more carbon atoms | [kg/hr] | 3.5 | 3.5 | 3.5 | 3.5 | 3.5 | 3.5 | 3.5 |
| Of which, olefin having 4 to 6 carbon atoms | [kg/hr] | 1.1 | 1.1 | 1.1 | 1.1 | 1.1 | 1.1 | 1.1 |
| Water vapor (dilution) | [kg/hr] | 0.5 | 1.1 | 1.5 | 1.7 | 0.2 | 0.0 | 2.4 |
| Mass flow rate of raw material mixture fed | [kg/hr] | 10.8 | 10.8 | 10.8 | 10.8 | 6.7 | 10.8 | 10.8 |
| Mass flow rate of effective raw material fed | [kg/hr] | 4.9 | 4.9 | 4.9 | 4.9 | 2.8 | 4.9 | 4.9 |
| Pressure | [MPaG] | 0.15 | 0.15 | 0.15 | 0.15 | 0.15 | 0.15 | 0.15 |
| WHSV | [$hr^{-1}$] | 4.9 | 4.9 | 4.9 | 4.9 | 4.9 | 4.9 | 4.9 |
| Reaction time | [h] | 48 | 48 | 48 | 48 | 48 | 48 | 48 |
| Reaction temperature | [° C.] | 540 | 540 | 540 | 540 | 540 | 540 | 540 |
| Catalyst bed inlet temperature | [° C.] | 568 | 539 | 522 | 511 | 572 | 590 | 477 |
| Catalyst bed outlet temperature | [° C.] | 512 | 541 | 558 | 569 | 508 | 490 | 603 |
| Temperature difference between inlet and outlet | [K] | −55 | 1 | 35 | 58 | −64 | −101 | 127 |
| Propylene yield | [% by mass] | 22.5 | 23.7 | 23.2 | 22.7 | 20.4 | 17.6 | 16.5 |
| Aromatic yield | [% by mass] | 3.0 | 2.6 | 2.8 | 2.4 | 3.9 | 1.4 | 1.2 |
| Coke yield | [ppm by mass] | 315 | 273 | 277 | 318 | 320 | 507 | 565 |

Examples of Second Embodiment

Hereinafter, the present invention will be described in more detail with reference to Examples of the second embodiment. However, the present invention is not limited by Examples described below.

[Method for Converting Ethanol]

(Reaction Apparatus)

In Examples and Comparative Examples given below, evaluation was conducted using the fixed-bed single-stage adiabatic reactor 1 shown in FIG. 1.

(Raw Material)

The molar ratio of methanol/ethanol, the molar ratio of olefin having 4 to 6 carbon atoms/methanol, and the molar ratio of ethylene/ethanol in Examples and Comparative Examples were calculated according to the following expressions.

$$\text{Molar ratio } (-) \text{ of methanol/ethanol} = \text{Molar flow rate (mol/hr) of methanol/Molar flow rate (mol/hr) of ethanol}$$

$$\text{Molar ratio } (-) \text{ of methanol/olefin having 4 to 6 carbon atoms} = \text{Molar flow rate (mol/hr) of methanol/Flow rate (mol/hr) of olefin having 4 to 6 carbon atoms}$$

$$\text{Molar ratio } (-) \text{ of ethylene/ethanol} = \text{Molar flow rate (mol/hr) of ethylene/Molar flow rate (mol/hr) of ethanol}$$

(Temperature Measurement)

The temperature of a catalyst bed inlet and the temperature of a catalyst bed outlet were measured by a thermocouple inserted from the outside of the reactor. Specifically, as shown in FIG. 1, temperatures at 0.5 d to 0.6 d were measured, wherein d represents the distance from the center of the reactor to the inner wall surface of the reactor when the center of the reactor in a plane perpendicular to the flow direction of a fluid was defined as 0. The influence of heat dissipation ascribable to the insertion of this thermocouple was negligibly small.

(Evaluation of Reaction)

Reaction was carried out in accordance with Examples and Comparative Examples given below such that an inlet-outlet average reaction temperature was 540 °C. A portion of a gas from the reactor outlet was sampled every 3 hours from the start of the reaction, introduced to a gas chromatograph (TCD and FID detectors), and analyzed for reaction gas composition. The reaction was terminated 48 hours after the start of the reaction. An average value of GC analysis results from the start of the reaction to the termination of the reaction was calculated. The inlet-outlet average reaction temperature was calculated according to the following expression and described as "Reaction temperature" in the tables.

$$\text{Inlet-outlet average reaction temperature } (^\circ\text{C.}) = [\text{Catalyst bed inlet temperature } (^\circ\text{C.}) + \text{Catalyst bed outlet temperature } (^\circ\text{C.})]/2$$

(Coke Yield)

In Examples and Comparative Examples given below, nitrogen was fed into a reactor after the termination of reaction to purge a hydrocarbon, and a catalyst bed was kept at 500 °C. Subsequently, air/nitrogen having an oxygen concentration of 2% by volume was circulated thereinto to remove coke on the catalyst by combustion. In this respect, a gas from the reactor outlet was regularly sampled, and the regeneration gas was analyzed using a gas chromatograph to measure $CO_2$ and CO concentrations. From the resulting values, the amount of carbon deposited on the catalyst was determined, and this amount was regarded as the amount of coke. The method for analyzing the regeneration gas using a gas chromatograph will be described below (Analysis conditions for gas chromatograph). The coke yield in Examples and Comparative Examples given below was determined according to the following expression.

$$\text{Coke yield (ppm by mass)} = \text{Amount of coke}/[\text{Mass flow rate of effective raw material fed (kg/hr)} \times \text{Reaction time (hr)}]$$

$$\text{Mass flow rate of effective raw material fed (kg/hr)} = \text{Ethylene flow rate (kg/hr)} + \text{Ethanol flow rate in terms of ethylene (kg/hr)} + \text{Methanol flow rate in terms of methylene} + \text{Flow rate (kg/hr) of olefin having 4 to 6 carbon atoms} + \text{Flow rate (kg/hr) of oxygenate having 1 to 6 carbon atoms other than methanol and ethanol}$$

$$\text{Ethanol flow rate in terms of ethylene (kg/hr)} = \text{Ethanol flow rate (kg/hr)} \times 0.609$$

$$\text{Methanol flow rate in terms of methylene (kg/hr)} = \text{Methanol flow rate (kg/hr)} \times 0.438$$

(Analysis Conditions for Gas Chromatograph)

<<Analysis of Regeneration Gas>>

Apparatus: GC-8A from Shimadzu Corp.

Column: The following columns (1) and (2) were connected in parallel and used.

Column (1): SUS column (inside diameter: 3 mm, length: 3 m) packed with 80- to 100-mesh molecular sieve 5A (manufactured by FUJIFILM Wako Pure Chemical Corp.)

Column (2): 80- to 100-mesh Porapac-Q (inside diameter: 3 mm, length: 2 m) manufactured by Waters Associates (USA) and SUS resistant column (inside diameter: 3 mm, length: 1 m) connected directly Column temperature: 70 °C.

Carrier gas (helium) flow rate: 60 mL/min

<<Analysis of Reaction Gas>>

Apparatus: GC-2030 manufactured by Shimadzu Corp.

Column: Custom capillary column SPB-1 (inside diameter: 0.25 mm, length: 60 m, film thickness: 3.0 μm) manufactured by Supelco, Inc. (USA)

Amount of sample gas: 1 mL (a sampling line was kept at 200 °C to 300 °C.)

Heating program: Held at 40 °C. for 12 minutes, subsequently heated to 200 °C. at 5 °C./min, and then held at 200 °C. for 22 minutes.

Split ratio: 200:1

Carrier gas (nitrogen) flow rate: 120 mL/min

FID detector: Air feed pressure of 50 kPa (approximately 500 mL/min), hydrogen feed pressure of 60 kPa (approximately 50 mL/min)

Measurement method: A TCD detector and an FID detector were connected in series. Compositional analysis was conducted on the basis of data on hydrogen detected in the TCD detector and data on oxygenates, such as hydrocarbons and ethanol, detected in the FID detector. The concentration of propylene, the concentration of benzene, the concentration of toluene, and the concentration of an aromatic hydrocarbon having 8 carbon atoms in a reaction gas were determined by use of the calibration curve method, and the masses per hour of propylene and aromatic compounds produced through reaction were determined. The mass per hour of aromatic compounds produced through reaction is the total mass per hour of benzene, toluene, and an aromatic hydrocarbon having 8 carbon atoms produced through reaction.

A propylene yield and an aromatic yield were calculated according to the following expressions.

Propylene yield (% by mass) = Mass per hour of propylene produced through reaction (kg/hr)/Mass flow rate of effective raw material fed (kg/hr)

Aromatic yield (% by mass) = Mass per hour of aromatic compound produced through reaction (kg/hr)/Mass flow rate of effective raw material fed (kg/hr)

Mass flow rate of effective raw material fed (kg/hr) = Ethylene flow rate (kg/hr) + Ethanol flow rate in terms of ethylene (kg/hr) + Methanol flow rate in terms of methylene (kg/hr) + Flow rate (kg/hr) of olefin having 4 to 6 carbon atoms + Flow rate (kg/hr) of oxygenate having 1 to 6 carbon atoms other than methanol and ethanol Ethanol flow rate in terms of ethylene (kg/hr) = Ethanol flow rate (kg/hr) × 0.609

Methanol flow rate in terms of methylene (kg/hr) = Methanol flow rate (kg/hr) × 0.438

Example B1

A raw material mixture gas composed of methanol and ethanol and having a molar ratio of methanol/ethanol of 0.22 was heated, fed at WHSV=3.8 into a reactor filled with zeolite-containing catalyst 1, and reacted. In this respect, the inlet temperature and the outlet temperature of the catalyst bed were 563 °C. and 518 °C, respectively, and the inlet-outlet average reaction temperature was 540 °C. The average propylene yield and the aromatic yield from the start of the reaction to the termination of the reaction were 19.5% by mass and 7.8% by mass, respectively. The coke yield of the zeolite-containing catalyst after the completion of 48-hour operation was 277 ppm by mass. The details of reaction results and reaction conditions are shown in Table 4.

Example B2

A raw material mixture gas composed of methanol and ethanol and having a molar ratio of methanol/ethanol of 0.50 was heated, fed at WHSV=3.8 into a reactor filled with zeolite-containing catalyst 1, and reacted. In this respect, the inlet temperature and the outlet temperature of the catalyst bed were 536 °C. and 544 °C, respectively, and the inlet-outlet average reaction temperature was 540 °C. The average propylene yield and the aromatic yield from the start of the reaction to the termination of the reaction were 20.1% by mass and 7.5% by mass, respectively. The coke yield of the zeolite-containing catalyst after the completion of 48-hour operation was 270 ppm by mass. The details of reaction results and reaction conditions are shown in Table 4.

Example B3

A raw material mixture gas composed of methanol and ethanol and having a molar ratio of methanol/ethanol of 0.86 was heated, fed at WHSV=3.8 into a reactor filled with zeolite-containing catalyst 1, and reacted. In this respect, the inlet temperature and the outlet temperature of the catalyst bed were 511 °C. and 569 °C, respectively, and the inlet-outlet average reaction temperature was 540 °C. The average propylene yield and the aromatic yield from the start of the reaction to the termination of the reaction were 19.3% by mass and 8.8% by mass, respectively. The coke yield of the zeolite-containing catalyst after the completion of 48-hour operation was 357 ppm by mass. The details of reaction results and reaction conditions are shown in Table 4.

Comparative Example B1

The same reaction as in Example B1 was performed except that: an ethanol gas containing no methanol was used alone as a raw material gas; and the catalyst bed inlet temperature was adjusted to 588 °C. In this respect, the outlet temperature of the catalyst bed was 492 °C, and the inlet-outlet average reaction temperature was 540 °C. The average propylene yield and the aromatic yield from the start of the reaction to the termination of the reaction were 18.3% by mass and 1.2% by mass, respectively. The coke yield of the zeolite-containing catalyst after the completion of 48-hour operation was 483 ppm by mass. Reaction results are shown together with reaction conditions in Table 4.

Comparative Example B2

The same reaction as in Example B1 was performed except that: a methanol containing no ethanol was used alone as a raw material gas; and the catalyst bed inlet temperature was adjusted to 450 °C. As a result, the temperature of the catalyst bed outlet still continued to elevate beyond 650 °C. Therefore, the reaction was terminated after a lapse of 1 hour from a safety standpoint. From this Comparative Example, it is found that fiercely exothermic reaction is difficult to carry out efficiently in an adiabatic reactor.

TABLE 4

| | | Example B1 | Example B2 | Example B3 | Comparative Example B1 | Comparative Example B2 |
|---|---|---|---|---|---|---|
| Molar ratio of methanol/ethanol | | 0.22 | 0.50 | 0.86 | 0.00 | — |
| Methanol | [kg/hr] | 0.87 | 1.74 | 2.60 | 0.00 | 8.67 |
| Ethanol | [kg/hr] | 5.62 | 4.99 | 4.37 | 6.24 | 0.00 |
| Mass flow rate of raw material mixture fed | [kg/hr] | 6.48 | 6.73 | 6.97 | 6.24 | 8.67 |
| Mass flow rate of effective raw material fed | [kg/hr] | 3.80 | 3.80 | 3.80 | 3.80 | 3.80 |
| Pressure | [MPaG] | 0.15 | 0.15 | 0.15 | 0.15 | 0.15 |
| WHSV | [$hr^{-1}$] | 3.8 | 3.8 | 3.8 | 3.8 | 3.8 |
| Reaction time | [h] | 48 | 48 | 48 | 48 | 1 |
| Reaction temperature | [° C.] | 540 | 540 | 540 | 540 | — |
| Catalyst bed inlet temperature | [° C.] | 563 | 536 | 511 | 588 | 450 |
| Catalyst bed outlet temperature | [° C.] | 518 | 544 | 569 | 492 | — |

TABLE 4-continued

| | | Example B1 | Example B2 | Example B3 | Comparative Example B1 | Comparative Example B2 |
|---|---|---|---|---|---|---|
| Temperature difference between inlet and outlet | [K] | −45 | 8 | 58 | −96 | — |
| Propylene yield | [% by mass] | 19.5 | 20.1 | 19.3 | 18.3 | — |
| Aromatic yield | [% by mass] | 7.8 | 7.5 | 8.8 | 1.2 | — |
| Coke yield | [ppm by mass] | 277 | 270 | 357 | 483 | — |

The results of Examples B1 to B3 and Comparative Examples B1 and B2 revealed that use of a raw material mixture having a molar ratio of methanol/ethanol in a specific range can achieve both of a high propylene yield and aromatic yield and suppression of coke deposition on a catalyst.

Example B4

A raw material mixture gas composed of methanol, ethanol, and hydrocarbons having 4 or more carbon atoms mainly containing hydrocarbons having 4 to 8 carbon atoms at the compositional ratio shown in Table 5, and having a molar ratio of methanol/ethanol and that of olefin having 4 to 6 carbon atoms/methanol of 0.35 and 0.97, respectively, was heated, fed at WHSV=4.9 into a reactor filled with a zeolite-containing catalyst, and reacted. In this respect, the inlet temperature and the outlet temperature of the catalyst bed were 566 °C. and 514 °C, respectively, and the inlet-outlet average reaction temperature was 540 °C. The average propylene yield and the aromatic yield from the start of the reaction to the termination of the reaction were 18.9% by mass and 8.3% by mass, respectively. The coke yield of the zeolite-containing catalyst after the completion of 48-hour operation was 315 ppm by mass. The details of reaction results and reaction conditions are shown in Table 6. In this Example, the aromatic yield was calculated from the difference between the aromatic concentration of the raw material and the aromatic concentration of the reaction gas.

Example B5

The same reaction as in Example B4 was performed except that: a raw material mixture gas having a molar ratio of methanol/ethanol of 0.50 and a molar ratio of olefin having 4 to 6 carbon atoms/methanol of 0.49 was used; and the inlet temperature of the catalyst bed was adjusted to 558 °C. In this respect, the outlet temperature of the catalyst bed was 522 °C, and the inlet-outlet average reaction temperature was 540 °C. The average propylene yield and the aromatic yield from the start of the reaction to the termination of the reaction were 19.5% by mass and 7.8% by mass, respectively. The coke yield of the zeolite-containing catalyst after the completion of 48-hour operation was 297 ppm by mass. Reaction results are shown together with reaction conditions in Table 6.

Example B6

The same reaction as in Example B4 was performed except that: a raw material mixture gas having a molar ratio of methanol/ethanol of 0.86 and a molar ratio of olefin having 4 to 6 carbon atoms/methanol of 0.32 was used; and the inlet temperature of the catalyst bed was adjusted to 541 °C. In this respect, the outlet temperature of the catalyst bed was 539 °C, and the inlet-outlet average reaction temperature was 540 °C. The average propylene yield and the aromatic yield from the start of the reaction to the termination of the reaction were 19.9% by mass and 7.6% by mass, respectively. The coke yield of the zeolite-containing catalyst after the completion of 48-hour operation was 270 ppm by mass. Reaction results are shown together with reaction conditions in Table 6.

Example B7

The same reaction as in Example B4 was performed except that: a raw material mixture gas having a molar ratio of methanol/ethanol of 1.33 and a molar ratio of olefin having 4 to 6 carbon atoms/methanol of 0.24 was used; and the inlet temperature of the catalyst bed was adjusted to 526 °C. In this respect, the outlet temperature of the catalyst bed was 554 °C, and the inlet-outlet average reaction temperature was 540 °C. The average propylene yield and the aromatic yield from the start of the reaction to the termination of the reaction were 19.5% by mass and 7.6% by mass, respectively. The coke yield of the zeolite-containing catalyst after the completion of 48-hour operation was 266 ppm by mass. Reaction results are shown together with reaction conditions in Table 6.

Comparative Example B3

The same reaction as in Example B2 was performed except that: methanol and an olefin having 4 to 6 carbon atoms were used as a raw material gas without the use of ethanol; and the inlet temperature of the catalyst bed was adjusted to 441 °C. In this respect, the outlet temperature of the catalyst bed was 639 °C, and the inlet-outlet average reaction temperature was 540 °C. The average propylene yield and the aromatic yield from the start of the reaction to the termination of the reaction were 14.8% by mass and 11.3% by mass, respectively. The coke yield of the zeolite-containing catalyst after the completion of 48-hour operation was 684 ppm by mass. Reaction results are shown together with reaction conditions in Table 6.

TABLE 5

| | Content (% by mass) |
|---|---|
| Butene | 34.3 |
| Butane | 3.7 |
| Pentene | 21.1 |
| Pentane | 2.1 |
| Hexene | 9.5 |
| Benzene | 0.6 |
| Heptene | 5.4 |
| Toluene | 3.8 |
| Octene | 2.0 |
| Aromatic hydrocarbon having 8 carbon atoms | 15.3 |
| Hydrocarbon having 9 or more carbon atoms | 5.8 |
| Total | 100 |

TABLE 6

| | | Example B4 | Example B5 | Example B6 | Example B7 | Comparative Example B3 |
|---|---|---|---|---|---|---|
| Molar ratio of methanol/ethanol | | 0.35 | 0.50 | 0.86 | 1.33 | — |
| Molar ratio of olefin having 4 to 6 carbon atoms/methanol | | 0.97 | 0.49 | 0.32 | 0.24 | 0.10 |
| Methanol | [kg/hr] | 1.30 | 1.74 | 2.60 | 3.47 | 8.67 |
| Ethanol | [kg/hr] | 5.30 | 4.99 | 4.37 | 3.74 | 0.0 |
| Hydrocarbon having 4 or more carbon atoms | [kg/hr] | 3.46 | 3.46 | 3.46 | 3.46 | 3.46 |
| Of which, olefin having 4 to 6 carbon atoms | [kg/hr] | 1.14 | 1.14 | 1.14 | 1.14 | 1.14 |
| Mass flow rate of raw material mixture fed | [kg/hr] | 10.07 | 10.19 | 10.44 | 10.68 | 12.13 |
| Mass flow rate of effective raw material fed | [kg/hr] | 4.94 | 4.94 | 4.94 | 4.94 | 4.94 |
| Pressure | [MPaG] | 0.15 | 0.15 | 0.15 | 0.15 | 0.15 |
| WHSV | [$hr^{-1}$] | 4.9 | 4.9 | 4.9 | 4.9 | 4.9 |
| Reaction time | [h] | 48 | 48 | 48 | 48 | 48 |
| Reaction temperature | [° C.] | 540 | 540 | 540 | 540 | 540 |
| Catalyst bed inlet temperature | [° C.] | 566 | 558 | 541 | 526 | 441 |
| Catalyst bed outlet temperature | [° C.] | 514 | 522 | 539 | 554 | 639 |
| Temperature difference between inlet and outlet | [K] | −52 | −36 | 2 | 28 | 198 |
| Propylene yield | [% by mass] | 18.9 | 19.5 | 19.9 | 19.5 | 14.8 |
| Aromatic yield | [% by mass] | 8.3 | 7.8 | 7.6 | 7.6 | 11.3 |
| Coke yield | [ppm by mass] | 315 | 297 | 270 | 266 | 684 |

Example B8

The same reaction as in Example B4 was performed except that: a raw material mixture gas having a molar ratio of methanol/ethanol of 0.40, a molar ratio of olefin having 4 to 6 carbon atoms/methanol of 0.24, and a molar ratio of ethylene/ethanol of 0.13 was used; and the inlet temperature of the catalyst bed was adjusted to 555 °C. In this respect, the outlet temperature of the catalyst bed was 525 °C, and the inlet-outlet average reaction temperature was 540 °C. The average propylene yield and the aromatic yield from the start of the reaction to the termination of the reaction were 19.5% by mass and 7.4% by mass, respectively. The coke yield of the zeolite-containing catalyst after the completion of 48-hour operation was 251 ppm by mass. Reaction results are shown together with reaction conditions in Table 7.

Example B9

The same reaction as in Example B4 was performed except that: a raw material mixture gas having a molar ratio of methanol/ethanol of 0.46, a molar ratio of olefin having 4 to 6 carbon atoms/methanol of 0.20, and a molar ratio of ethylene/ethanol of 0.31 was used; and the inlet temperature of the catalyst bed was adjusted to 544 °C. In this respect, the outlet temperature of the catalyst bed was 536 °C, and the inlet-outlet average reaction temperature was 540 °C. The average propylene yield and the aromatic yield from the start of the reaction to the termination of the reaction were 19.8% by mass and 7.7% by mass, respectively. The coke yield of the zeolite-containing catalyst after the completion of 48-hour operation was 280 ppm by mass. Reaction results are shown together with reaction conditions in Table 7.

Example B10

The same reaction as in Example B1 was performed except that: a raw material mixture gas having a molar ratio of methanol/ethanol of 0.078 and a molar ratio of ethylene/ethanol of 0.26 was used; and the inlet temperature of the catalyst bed was adjusted to 546 °C. In this respect, the outlet temperature of the catalyst bed was 534 °C, and the inlet-outlet average reaction temperature was 540 °C. The average propylene yield and the aromatic yield from the start of the reaction to the termination of the reaction were 19.8% by mass and 7.7% by mass, respectively. The coke yield of the zeolite-containing catalyst after the completion of 48-hour operation was 291 ppm by mass. Reaction results are shown together with reaction conditions in Table 7.

TABLE 7

| | | Example B8 | Example B9 | Example B10 |
|---|---|---|---|---|
| Molar ratio of methanol/ethanol | | 0.40 | 0.46 | 0.078 |
| Molar ratio of olefin having 4 to 6 carbon atoms/methanol | | 0.24 | 0.20 | 0.16 |
| Molar ratio of ethylene/ethanol | | 0.13 | 0.31 | 0.26 |
| Methanol | [kg/hr] | 1.30 | 1.30 | 0.26 |
| Ethanol | [kg/hr] | 4.68 | 4.06 | 4.80 |
| Ethylene | [kg/hr] | 0.38 | 0.76 | 0.76 |
| Hydrocarbon having 4 or more carbon atoms | [kg/hr] | 3.46 | 3.46 | — |
| Of which, olefin having 4 to 6 carbon atoms | [kg/hr] | 1.14 | 1.14 | — |
| Mass flow rate of raw material mixture fed | [kg/hr] | 9.45 | 8.82 | 5.06 |
| Mass flow rate of effective raw material fed | [kg/hr] | 4.94 | 4.94 | 3.80 |
| Pressure | [MPaG] | 0.15 | 0.15 | 0.15 |
| WHSV | [$hr^{-1}$] | 4.9 | 4.9 | 3.8 |
| Reaction time | [h] | 48 | 48 | 48 |
| Reaction temperature | [° C.] | 540 | 540 | 540 |
| Catalyst bed inlet temperature | [° C.] | 555 | 544 | 546 |
| Catalyst bed outlet temperature | [° C.] | 525 | 536 | 534 |
| Temperature difference between inlet and outlet | [K] | −30 | −8 | −12 |
| Propylene yield | [% by mass] | 19.5 | 19.8 | 19.8 |

TABLE 7-continued

| | | Example B8 | Example B9 | Example B10 |
|---|---|---|---|---|
| Aromatic yield | [% by mass] | 7.4 | 7.7 | 7.7 |
| Coke yield | [ppm by mass] | 251 | 280 | 291 |

Examples of Third Embodiment

Hereinafter, the present invention will be described in more detail with reference to Examples of the third embodiment. However, the present invention is not limited by Examples described below.

[Method for Converting Ethanol]

(Reaction Apparatus)

In Examples and Comparative Examples given below, evaluation is conducted using the fixed-bed single-stage adiabatic reactor 1 shown in FIG. 1.

(Raw Material)

The molar ratio of ethylene/ethanol and the molar ratio of olefin having 4 to 6 carbon atoms/ethylene in Examples and Comparative Examples are calculated according to the following expressions.

$$\text{Molar ratio } (-) \text{ of ethylene/ethanol} = \text{Molar flow rate (mol/hr) of ethylene/Molar flow rate (mol/hr) of ethanol}$$

$$\text{Molar ratio } (-) \text{ of olefin having 4 to 6 carbon atoms/ethylene} = \text{Flow rate (mol/hr) of olefin having 4 to 6 carbon atoms/Molar flow rate (mol/hr) of ethylene}$$

(Temperature Measurement)

The temperature of a catalyst bed inlet and the temperature of a catalyst bed outlet are measured by a thermocouple inserted from the outside of the reactor. Specifically, as shown in FIG. 1, temperatures at 0.5 d to 0.6 d are measured, wherein d represents the distance from the center of the reactor to the inner wall surface of the reactor when the center of the reactor in a plane perpendicular to the flow direction of a fluid is defined as 0. The influence of heat dissipation ascribable to the insertion of this thermocouple is negligibly small.

(Evaluation of Reaction)

Reaction is carried out in accordance with Examples and Comparative Examples given below such that an inlet-outlet average reaction temperature is 540 °C. A portion of a gas from the reactor outlet is sampled every 3 hours from the start of the reaction, introduced to a gas chromatograph (TCD and FID detectors), and analyzed for reaction gas composition. The reaction was terminated 48 hours after the start of the reaction. An average value of GC analysis results from the start of the reaction to the termination of the reaction is calculated. The inlet-outlet average reaction temperature is calculated according to the following expression and described as "Reaction temperature" in the tables.

$$\text{Inlet-outlet average reaction temperature } (^\circ\text{ C.}) = [\text{Catalyst bed inlet temperature } (^\circ\text{ C.}) + \text{Catalyst bed outlet temperature } (^\circ\text{ C.})]/2$$

(Coke Yield)

In Examples and Comparative Examples given below, nitrogen is fed into a reactor after the termination of reaction to purge a hydrocarbon, and a catalyst bed is kept at 500 °C. Subsequently, air/nitrogen having an oxygen concentration of 2% by volume is circulated thereinto to remove coke on the catalyst by combustion. In this respect, a gas from the reactor outlet is regularly sampled, and the regeneration gas is analyzed using a gas chromatograph to measure $CO_2$ and CO concentrations. From the resulting values, the amount of carbon deposited on the catalyst is determined, and this amount is regarded as the amount of coke. The method for analyzing the regeneration gas using a gas chromatograph will be described below (Analysis conditions for gas chromatograph). The coke yield in Examples and Comparative Examples given below is determined according to the following expression.

$$\text{Coke yield (ppm by mass)} = \text{Amount of coke}/[\text{Mass flow rate of effective raw material fed (kg/hr)} \times \text{Reaction time (hr)})$$

$$\text{Mass flow rate of effective raw material fed (kg/hr)} = \text{Ethylene flow rate (kg/hr)} + \text{Ethanol flow rate in terms of ethylene (kg/hr)} + \text{Flow rate (kg/hr) of olefin having 4 to 6 carbon atoms} + \text{Flow rate (kg/hr) of oxygenate having 1 to 6 carbon atoms other than ethanol}$$

$$\text{Ethanol flow rate in terms of ethylene (kg/hr)} = \text{Ethanol flow rate (kg/hr)} \times \text{Molecular weight (g/mol) of ethylene/Molecular weight (g/mol) of ethanol}$$

[Analysis Conditions for Gas Chromatograph]

(Analysis of Regeneration Gas)

- Apparatus: GC-8A from Shimadzu Corp.
- Column: The following columns (1) and (2) were connected in parallel and used.
- Column (1): SUS column (inside diameter: 3 mm, length: 3 m) packed with 80- to 100-mesh molecular sieve 5A (manufactured by FUJIFILM Wako Pure Chemical Corp.)
- Column (2): 80- to 100-mesh Porapac-Q (inside diameter: 3 mm, length: 2 m) manufactured by Waters Associates (USA) and SUS resistant column (inside diameter: 3 mm, length: 1 m) connected directly
- Column temperature: 70 °C.
- Carrier gas (helium) flow rate: 60 mL/min (Analysis of Reaction Gas)

- Apparatus: GC-2030 manufactured by Shimadzu Corp.
- Column: Custom capillary column SPB-1 (inside diameter: 0.25 mm, length: 60 m, film thickness: 3.0 μm) manufactured by Supelco, Inc. (USA)
- Amount of sample gas: 1 mL (a sampling line was kept at 200 °C to 300 °C.)
- Heating program: Held at 40 °C. for 12 minutes, subsequently heated to 200 °C. at 5 °C./min, and then held at 200 °C. for 22 minutes.

Split ratio: 200:1

Carrier gas (nitrogen) flow rate: 120 mL/min

FID detector: Air feed pressure of 50 kPa (approximately 500 mL/min), hydrogen feed pressure of 60 kPa (approximately 50 mL/min)

Measurement method: A TCD detector and an FID detector are connected in series. Compositional analysis is conducted on the basis of data on hydrogen detected in the TCD detector and data on oxygenates such as hydrocarbons and ethanol detected in the FID detector. The concentration of a target compound in a reaction gas is determined by use of the calibration curve method, and the mass per hour of the compound produced through reaction is determined.

(Propylene Yield)

The propylene yield indicates the selectivity of reaction for propylene and is calculated according to the following expression.

Propylene yield (% by mass) = Mass per hour of propylene produced through reaction (kg/hr)/Mass flow rate of effective raw material fed (kg/hr)

Mass flow rate of effective raw material fed (kg/hr) = Ethylene flow rate (kg/hr) + Ethanol flow rate in terms of ethylene (kg/hr) + Flow rate (kg/hr) of olefin having 4 to 6 carbon atoms + Flow rate (kg/hr) of oxygenate having 1 to 6 carbon atoms other than ethanol Ethanol flow rate in terms of ethylene (kg/hr) = Ethanol flow rate (kg/hr) × Molecular weight (g/mol) of ethylene/Molecular weight (g/mol) of ethanol (Recovery Yield)

The recovery yields of propylene and an aromatic compound are calculated according to the expressions given below. The recovery yield of each component refers to the amount of each component discharged with respect to a raw material introduced to a reactor. The amount of each component discharged is the mass per hour of each component discharged to the outside of the system through a separation step.

Recovery yield (% by mass) of propylene = Amount (kg/hr) of propylene discharged/Mass flow rate of raw material mixture fed (kg/hr)

Recovery yield (% by mass) of aromatic compound = Amount (kg/hr) of aromatic compound discharged/Mass flow rate of raw material mixture fed (kg/hr)

Reference Example 1

A raw material mixture gas (ethylene: 1.0 kg/hr, ethanol: 4.6 kg/hr, and water vapor: 0.7 kg/hr) having a molar ratio of ethylene/ethanol of 0.37 was heated, fed at WHSV=3.8 into a reactor filled with zeolite-containing catalyst 1, and reacted. In this respect, the inlet temperature and the outlet temperature of the catalyst bed were 539 °C. and 542 °C, respectively, and the inlet-outlet average reaction temperature was 540 °C. The average propylene yield and the aromatic yield from the start of the reaction to the termination of the reaction were 23.2% by mass and 2.7% by mass, respectively. The coke yield of the zeolite-containing catalyst after the completion of 48-hour operation was 270 ppm by mass.

From this Reference Example, it was found that, by controlling the molar ratio between ethylene and ethanol, ethylene and ethanol can be converted to a target compound while controlling a reaction temperature.

Reference Example 2

A raw material mixture gas (ethylene: 1.7 kg/hr, ethanol: 3.4 kg/hr, olefin having 4 to 6 carbon atoms: 1.1 kg/hr, and water vapor: 1.1 kg/hr) having a molar ratio of ethylene/ethanol of 0.82 and a molar ratio of ethylene/olefin having 4 to 6 carbon atoms of 0.3 was heated, fed at WHSV=4.9 into a reactor filled with zeolite-containing catalyst 1, and reacted. In this respect, the inlet temperature and the outlet temperature of the catalyst bed were 539 °C. and 541 °C, respectively, and the inlet-outlet average reaction temperature was 540 °C. The average propylene yield and the aromatic yield from the start of the reaction to the termination of the reaction were 22.5% by mass and 13.1% by mass, respectively. The coke yield of the zeolite-containing catalyst after the completion of 48-hour operation was 273 ppm by mass.

Example C1

The method for converting ethanol according to the present embodiment is examined for its effect by the apparatus shown in FIG. 9. A raw material is fed into reactor 1 filled with zeolite-containing catalyst 1 to obtain a reaction gas. The obtained reaction gas is applied to cooling apparatus 6 to thereby separate it into fraction C mainly containing a hydrocarbon having 6 or less carbon atoms and fraction D mainly containing water and a hydrocarbon having 7 or more carbon atoms. The fraction C is applied to first distillation column 2 to thereby separate it into fraction A mainly containing a hydrocarbon having 3 or less carbon atoms and fraction B mainly containing a hydrocarbon having 4 or more carbon atoms. These fractions are used as a raw material such that the recycling ratio of the fraction A and that of the fraction B are 0.60 and 0.90, respectively. As for the process described above, the yield of propylene, etc. by steady operation are shown in Table 8 on the basis of the results of Reference Examples 1 and 2 mentioned above.

In the raw material introduced to the reactor 1, the molar ratio of ethylene/ethanol is 0.40, and the molar ratio of olefin having 4 to 6 carbon atoms/ethylene is 0.43. The composition of components (mainly hydrocarbons having 4 or more carbon atoms) recycled from the fraction B contained in the raw material is shown in Table 9. When the feed rate of the raw material into the reactor is set to WHSV=3.8 at an inlet temperature of the catalyst bed of 553 °C, the outlet temperature is 527 °C. and the inlet-outlet average reaction temperature is 540 °C. The average propylene yield from the start of the reaction to the termination of the reaction is 22.1% by mass, and the coke yield of the zeolite-containing catalyst after the completion of 48-hour operation is 251 ppm by mass. The recovery yield of propylene and the recovery yield of an aromatic compound obtained at the outlet in the separation step are 5.4% by mass and 12.3% by mass, respectively.

Example C2

The method for converting ethanol according to the present embodiment is examined for its effect by the apparatus shown in FIG. 10. A raw material is fed into reactor 1 filled with zeolite-containing catalyst 1 to obtain a reaction gas. The obtained reaction gas is applied to cooling apparatus 6 to thereby separate it into fraction C mainly containing a hydrocarbon having 6 or less carbon atoms and fraction D mainly containing water and a hydrocarbon having 7 or more carbon atoms. The fraction C is applied to first distillation column 2 to thereby separate it into fraction A mainly containing a hydrocarbon having 3 or less carbon atoms and fraction B mainly containing a hydrocarbon having 4 or more carbon atoms. The obtained fraction A is applied to second distillation column 8 to thereby separate it into fraction A-1 mainly containing a hydrocarbon having 2 or less carbon atoms and fraction A-2 mainly containing a hydrocarbon having 3 carbon atoms. These fractions are used as a raw material such that the recycling ratio of the fraction A-1 and that of the fraction B are 0.72 and 0.90, respectively. As for the process described above, the yield of propylene, etc. by steady operation are shown in Table 8 on the basis of the results of Reference Examples 1 and 2 mentioned above.

In the raw material introduced to the reactor 1, the molar ratio of ethylene/ethanol is 0.40, and the molar ratio of olefin having 4 to 6 carbon atoms/ethylene is 0.36. The composition of components (mainly hydrocarbons having 4 or more carbon atoms) recycled from the fraction B contained in the raw material is shown in Table 9. The feed rate of the raw material into the reactor 1 is set to WHSV=3.8, the inlet temperature of the catalyst bed is 547 °C, the outlet temperature is 533 °C, and the inlet-outlet average reaction temperature is 540 °C. The average propylene yield from the start of the reaction to the termination of the reaction is 23.5% by mass, and the coke yield of the zeolite-containing catalyst after the completion of 48-hour operation is 235 ppm by mass. The recovery yield of propylene and the recovery yield of an aromatic compound obtained at the outlet in the separation step are 15.5% by mass and 14.0% by mass, respectively.

As is evident from the comparison of Example C1 with Example C2, the recovery yield of propylene is improved by disposing a distillation column for separation between fraction A-1 mainly containing a hydrocarbon having 2 or less carbon atoms and fraction A-2 mainly containing a hydrocarbon having 3 carbon atoms.

Example C3

The conversion method according to the present embodiment is examined for its effect by the apparatus shown in FIG. 11. A raw material is fed into reactor 1 filled with zeolite-containing catalyst 1 to obtain a reaction gas. The obtained reaction gas is applied to cooling apparatus 6 to thereby separate it into fraction C mainly containing a hydrocarbon having 6 or less carbon atoms and fraction D mainly containing water and a hydrocarbon having 7 or more carbon atoms. The fraction C is applied to first distillation column 2 to thereby separate it into fraction A mainly containing a hydrocarbon having less than 3 carbon atoms, fraction B mainly containing hydrocarbon having 4 or more carbon atoms, and fraction E mainly containing a hydrocarbon having 3 carbon atoms. These fractions are used as a raw material such that the recycling ratio of the fraction A and that of the fraction B are 0.78 and 0.90, respectively. As for the process described above, the yield of propylene, etc. by steady operation are shown in Table 8 on the basis of the results of Reference Examples 1 and 2 mentioned above.

In the raw material introduced to the reactor 1, the molar ratio of ethylene/ethanol is 0.40, and the molar ratio of olefin having 4 to 6 carbon atoms/ethylene is 0.39. The composition of components (mainly hydrocarbons having 4 or more carbon atoms) recycled from the fraction B contained in the raw material is shown in Table 9. When the feed rate of the raw material into the reactor 1 is set to WHSV=3.8 at an inlet temperature of the catalyst bed of 549 °C, the outlet temperature is 531 °C. and the inlet-outlet average reaction temperature is 540 °C. The average propylene yield from the start of the reaction to the termination of the reaction is 23.8% by mass, and the coke yield of the zeolite-containing catalyst after the completion of 48-hour operation is 240 ppm by mass. The recovery yield of propylene and the recovery yield of an aromatic compound obtained at the outlet in the separation step are 12.1% by mass and 12.0% by mass, respectively.

As is evident from the comparison of Example C1 with Example C3, the recovery yield of propylene is improved by disposing, in a distillation column, a side-cut stage for discharging fraction E mainly containing a hydrocarbon having 3 carbon atoms from an intermediate portion of the first distillation column 2.

Comparative Example C1

A conversion method is performed by the apparatus having reactor 1 and cooling apparatus 6 shown in FIG. 12, to examine its effect. A raw material is fed into reactor 1 filled with zeolite-containing catalyst 1 to obtain a reaction gas. The obtained reaction gas is applied to cooling apparatus 6 to thereby separate it into fraction C mainly containing a hydrocarbon having 6 or less carbon atoms and fraction D mainly containing water and a hydrocarbon having 7 or more carbon atoms. These fractions are used as a raw material such that the recycling ratio of the fraction C is 0.67. As for the process described above, the yield of propylene, etc. by steady operation are shown in Table 8 on the basis of the results of Reference Examples 1 and 2 mentioned above.

In the raw material introduced to the reactor 1, the molar ratio of ethylene/ethanol is 0.40, and the molar ratio of olefin having 4 to 6 carbon atoms/ethylene is 0.29. When the feed rate of the raw material into the reactor 1 is set to WHSV=3.8 at an inlet temperature of the catalyst bed of 534 °C, the outlet temperature is 546 °C. and the inlet-outlet average reaction temperature is 540 °C. The average propylene yield from the start of the reaction to the termination of the reaction is 23.0% by mass, and the coke yield of the zeolite-containing catalyst after the completion of 48-hour operation is 255 ppm by mass. The recovery yield of propylene and the recovery yield of an aromatic compound obtained at the outlet in the separation step are 4.4% by mass and 12.1% by mass, respectively.

As is evident from the comparison of Example C1 with Comparative Example C1, the recovery yield of propylene is improved by performing the distillation step in recycling a reaction gas.

Comparative Example C2

A conversion method is performed by the apparatus having reactor 1 shown in FIG. 13, to examine its effect. A raw material is fed into reactor 1 filled with zeolite-containing catalyst 1 to obtain a reaction gas. The reaction gas is mixed with ethanol such that the recycling ratio of the reaction gas is 0.65 to obtain a raw material mixture having the same composition as that of the raw material.

In the raw material introduced to the reactor 1, the molar ratio of ethylene/ethanol is 0.40, and the molar ratio of olefin having 4 to 6 carbon atoms/ethylene is 0.15. When the feed rate of the raw material into the reactor 1 is set to WHSV=3.8 at an inlet temperature of the catalyst bed of 537 °C, the outlet temperature is 543 °C. and the inlet-outlet average reaction temperature is 540 °C. The average propylene yield from the start of the reaction to the termination of the reaction is 23.6% by mass, and the coke yield of the zeolite-containing catalyst after the completion of 48-hour operation is 310 ppm by mass. The recovery yield of propylene and the recovery yield of an aromatic compound obtained at the outlet in the separation step are 2.8% by mass and 7.4% by mass, respectively.

As is evident from the comparison of Example C1 with Comparative Examples C1 and C2, the recovery yield of propylene is improved by performing the distillation step and the cooling step in recycling a reaction gas.

introduced to the reactor 1 is changed. These fractions are used as a raw material such that the recycling ratio of the fraction A-1 and that of the fraction B are 0.42 and 0.90, respectively. The yield of propylene, etc. by steady operation are shown in Table 10 on the basis of the results of Reference Examples 1 and 2 mentioned above.

In the raw material introduced to the reactor 1, the molar ratio of ethylene/ethanol is set to 0.20, and the molar ratio of olefin having 4 to 6 carbon atoms/ethylene is set to 0.61. The composition of components (mainly hydrocarbons having 4 or more carbon atoms) recycled from the fraction B contained in the raw material is shown in Table 9. The feed rate of the raw material into the reactor 1 is set to WHSV=3.8, the inlet temperature of the catalyst bed is 563 °C, the outlet temperature is 517 °C. and the inlet-outlet average reaction temperature is 540 °C. The average propylene yield from the start of the reaction to the termination of the reaction is 22.1% by mass, and the coke yield of the zeolite-containing catalyst after the completion of 48-hour operation is 256 ppm by mass. The recovery yield of propylene and the recovery yield of an aromatic compound obtained at the outlet in the separation step are 13.8% by mass and 12.5% by mass, respectively.

TABLE 8

| | | Example C1 | Example C2 | Example C3 | Comparative Example C1 | Comparative Example C2 |
|---|---|---|---|---|---|---|
| Molar ratio of ethylene/ethanol | | 0.40 | 0.40 | 0.40 | 0.40 | 0.40 |
| Molar ratio of olefin having 4 to 6 carbon atoms/ethylene | | 0.43 | 0.36 | 0.39 | 0.29 | 0.15 |
| Ethylene | [kg/hr] | 10.9 | 10.9 | 10.9 | 10.9 | 10.9 |
| Ethanol | [kg/hr] | 44.6 | 44.6 | 44.6 | 44.6 | 44.6 |
| Olefin having 4 to 6 carbon atoms | [kg/hr] | 10.2 | 8.6 | 9.2 | 31.8 | 6.8 |
| Recycling ratio of fraction A (A-1) | | 0.60 | 0.72 | 0.78 | — | — |
| Ethylene percentage in fraction A (A-1) | [% by mass] | 58.3% | 94.2% | 78.5% | — | — |
| Propylene percentage in fraction A (A-1) | [% by mass] | 36.6% | 2.2% | 17.4% | — | — |
| Molar ratio of propylene/ethylene | | 0.63 | 0.02 | 0.22 | — | — |
| Recycling ratio of fraction B | | 0.90 | 0.90 | 0.90 | — | — |
| Mass flow rate of raw material mixture | [kg/hr] | 82.8 | 61.1 | 76.0 | 76.3 | 128.2 |
| Ethylene percentage in raw material mixture | [% by mass] | 13.1% | 17.8% | 14.3% | 14.2% | 8.5% |
| Pressure | [MPaG] | 0.15 | 0.15 | 0.15 | 0.15 | 0.15 |
| WHSV | [$hr^{-1}$] | 3.8 | 3.8 | 3.8 | 3.8 | 3.8 |
| Reaction time | [h] | 48 | 48 | 48 | 48 | 48 |
| Reaction temperature | [° C.] | 540 | 540 | 540 | 540 | 540 |
| Catalyst bed inlet temperature | [° C.] | 553 | 547 | 549 | 534 | 537 |
| Catalyst bed outlet temperature | [° C.] | 527 | 533 | 531 | 546 | 543 |
| Temperature difference between inlet and outlet | [K] | −26 | −16 | −18 | 10 | 6 |
| Composition at reactor outlet | | | | | | |
| Propylene yield | [% by mass] | 22.1 | 23.5 | 23.8 | 23.0 | 23.6 |
| Coke yield | [ppm by mass] | 251 | 235 | 240 | 255 | 310 |
| Recovery yield | | | | | | |
| Propylene yield | [% by mass] | 5.4 | 15.5 | 12.1 | 4.4 | 2.8 |
| Aromatic yield | [% by mass] | 12.3 | 14.0 | 12.0 | 12.1 | 7.4 |

TABLE 9

| | Content (% by mass) |
|---|---|
| Butene | 30.5 |
| Butane | 34.2 |
| Pentene | 16.2 |
| Pentane | 12.9 |
| Hexene | 4.3 |
| Heptene | 1.6 |
| Octene | 0.3 |
| Total | 100 |

Example C4

Operation is carried out in the same manner as in Example C2 except that the composition of the raw material to be Example C5

Operation is carried out in the same manner as in Example C2 except that the composition of the raw material to be introduced to the reactor 1 is changed. These fractions are used as a raw material such that the recycling ratio of the fraction A and that of the fraction B are 0.94 and 0.90, respectively. The yield of propylene, etc. by steady operation is shown in Table 10 on the basis of the results of Reference Examples 1 and 2 mentioned above.

In the raw material introduced to the reactor 1, the molar ratio of ethylene/ethanol is set to 0.60, and the molar ratio of olefin having 4 to 6 carbon atoms/ethylene is set to 0.27. The composition of components (mainly hydrocarbons having 4 or more carbon atoms) recycled from the fraction B contained in the raw material is shown in Table 9. The feed rate of the raw material into the reactor 1 is set to WHSV=3.8, the inlet temperature of the catalyst bed is 534 °C, the outlet temperature is 546 °C. and the inlet-outlet average reaction temperature is 540 °C. The average propylene yield from the start of the reaction to the termination of the reaction is 23.8% by mass, and the coke yield of the zeolite-containing catalyst after the completion of 48-hour operation is 220 ppm by mass. The recovery yield of propylene and the recovery yield of an aromatic compound obtained at the outlet in the separation step are 17.1% by mass and 15.5% by mass, respectively.

Example C6

Operation is carried out in the same manner as in Example C4 except that the recycling of the fraction B is not performed. A raw material is fed into reactor 1 filled with zeolite-containing catalyst 1 to obtain a reaction gas. The obtained reaction gas is applied to cooling apparatus 6 to thereby separate it into fraction C mainly containing a hydrocarbon having 6 or less carbon atoms and fraction D mainly containing water and a hydrocarbon having 7 or more carbon atoms. The fraction C is applied to first distillation column 2 to thereby separate it into fraction A mainly containing a hydrocarbon having 3 or less carbon atoms and fraction B mainly containing a hydrocarbon having 4 or more carbon atoms. The obtained fraction A is applied to second distillation column 8 to thereby separate it into fraction A-1 mainly containing a hydrocarbon having 2 or less carbon atoms and fraction A-2 mainly containing a hydrocarbon having 3 carbon atoms. The fraction A-1 is used as a raw material such that the recycling ratio of the fraction A-1 is 0.41. As for the process described above, the yield of propylene, etc. by steady operation are shown in Table 10 on the basis of the results of Reference Examples 1 and 2 mentioned above.

In the raw material introduced to the reactor 1, the molar ratio of ethylene/ethanol is 0.20. The feed rate of the raw material into the reactor 1 is set to WHSV=3.8, the inlet temperature of the catalyst bed is 563 °C, the outlet temperature is 517 °C and the inlet-outlet average reaction temperature is 540 °C. The average propylene yield from the start of the reaction to the termination of the reaction is 24.5% by mass, and the coke yield of the zeolite-containing catalyst after the completion of 48-hour operation is 210 ppm by mass. The recovery yield of propylene and the recovery yield of an aromatic compound obtained at the outlet in the separation step are 18.5% by mass and 1.7% by mass, respectively.

As is evident from the comparison of Example C2 with Example C6, the recovery yield of an aromatic compound is improved by recycling fraction B mainly containing a hydrocarbon having 4 or more carbon atoms.

Example C7

The conversion method according to the present embodiment is examined for its effect when ethylene is introduced as a raw material from the outside by the apparatus shown in FIG. 10. In this Example, additional ethylene is added to a raw material from the outside, in addition to ethylene contained in fraction A-1. A raw material is fed into reactor 1 filled with zeolite-containing catalyst 1 to obtain a reaction gas. The obtained reaction gas is applied to cooling apparatus 6 to thereby separate it into fraction C mainly containing a hydrocarbon having 6 or less carbon atoms and fraction D mainly containing water and a hydrocarbon having 7 or more carbon atoms. The fraction C is applied to first distillation column 2 to thereby separate it into fraction A mainly containing a hydrocarbon having 3 or less carbon atoms and fraction B mainly containing a hydrocarbon having 4 or more carbon atoms. The obtained fraction A is applied to second distillation column 8 to thereby separate it into fraction A-1 mainly containing a hydrocarbon having 2 or less carbon atoms and fraction A-2 mainly containing a hydrocarbon having 3 carbon atoms. These fractions are used as a raw material such that the recycling ratio of the fraction A-1 and that of the fraction B are 0.28 and 0.90, respectively. As for the process described above, the yield of propylene, etc. by steady operation are shown in Table 10 on the basis of the results of Reference Examples 1 and 2 mentioned above.

In the raw material introduced to the reactor 1, the molar ratio of ethylene/ethanol is 0.80, and the molar ratio of olefin having 4 to 6 carbon atoms/ethylene is 0.23. The composition of components (mainly hydrocarbons having 4 or more carbon atoms) recycled from the fraction B contained in the raw material is shown in Table 9. The feed rate of the raw material into the reactor 1 is set to WHSV=3.8, the inlet temperature of the catalyst bed is 520 °C, the outlet temperature is 560 °C and the inlet-outlet average reaction temperature is 540 °C. The average propylene yield from the start of the reaction to the termination of the reaction is 24.5% by mass, and the coke yield of the zeolite-containing catalyst after the completion of 48-hour operation is 321 ppm by mass. The recovery yield of propylene and the recovery yield of an aromatic compound obtained at the outlet in the separation step are 14.8% by mass and 13.4% by mass, respectively.

TABLE 10

| | | Example C2 | Example C4 | Example C5 | Example C6 | Example C7 |
|---|---|---|---|---|---|---|
| Molar ratio of ethylene/ethanol | | 0.40 | 0.20 | 0.60 | 0.20 | 0.80 |
| Molar ratio of olefin having 4 to 6 carbon atoms/ethylene | | 0.36 | 0.61 | 0.27 | 0.00 | 0.23 |
| Ethylene | [kg/hr] | 10.9 | 6.3 | 14.3 | 6.3 | 25.3 |
| Ethanol | [kg/hr] | 44.6 | 52.0 | 39.0 | 52.0 | 52.0 |
| Olefin having 4 to 6 carbon atoms | [kg/hr] | 8.6 | 8.5 | 8.6 | — | 12.8 |
| Recycling ratio of fraction A (A-1) | | 0.72 | 0.42 | 0.94 | 0.41 | 0.28 |
| Ethylene percentage in fraction A (A-1) | [% by mass] | 94.2% | 95.2% | 93.5% | 92.1% | 95.2% |
| Propylene percentage in fraction A (A-1) | [% by mass] | 2.2% | 1.8% | 2.4% | 3.1% | 2.9% |
| Molar ratio of propylene/ethylene | | 0.02 | 0.02 | 0.03 | 0.03 | 0.03 |
| Recycling ratio of fraction B | | 0.90 | 0.90 | 0.90 | 0.00 | 0.90 |
| Mass flow rate of raw material mixture | [kg/hr] | 61.1 | 68.4 | 76.0 | 38.2 | 95.6 |
| Ethylene percentage in raw material mixture | [% by mass] | 17.8% | 9.3% | 18.7% | 16.6% | 26.5% |

TABLE 10-continued

| | | Example C2 | Example C4 | Example C5 | Example C6 | Example C7 |
|---|---|---|---|---|---|---|
| Pressure | [MPaG] | 0.15 | 0.15 | 0.15 | 0.15 | 0.15 |
| WHSV | [$hr^{-1}$] | 3.8 | 3.8 | 3.8 | 3.8 | 3.8 |
| Reaction time | [h] | 48 | 48 | 48 | 48 | 48 |
| Reaction temperature | [° C.] | 540 | 540 | 540 | 540 | 540 |
| Catalyst bed inlet temperature | [° C.] | 547 | 563 | 534 | 563 | 520 |
| Catalyst bed outlet temperature | [° C.] | 533 | 517 | 546 | 517 | 560 |
| Temperature difference between inlet and outlet | [K] | −16 | −46 | 12 | −46 | 40 |
| Composition at reactor outlet | | | | | | |
| Propylene yield | [% by mass] | 23.5 | 22.1 | 23.8 | 24.5 | 24.5 |
| Coke yield | [ppm by mass] | 235 | 256 | 220 | 210 | 321 |
| Recovery yield | | | | | | |
| Propylene yield | [% by mass] | 15.5 | 13.8 | 17.1 | 18.5 | 14.8 |
| Aromatic yield | [% by mass] | 14.0 | 12.5 | 15.5 | 1.7 | 13.4 |

INDUSTRIAL APPLICABILITY

The present invention can provide a method for converting ethanol to a target compound in good yield by using an adiabatic reactor and controlling an internal temperature of the reactor, and as such, has industrial applicability because the target compound such as propylene or an aromatic compound can be used in chemical product synthesis and the like.

REFERENCE SIGNS LIST

1: adiabatic reactor, 12: reaction housing, 121: heat insulation material, 13: catalyst bed, 131: catalyst bed inlet, 132: catalyst bed outlet, 14: reactor inlet, 15: reactor outlet, 161: first sheathed thermocouple, 162: second sheathed thermocouple, 2, 3, 4, and 8: distillation column, 5: steam cracking apparatus, 6: cooling apparatus, 7: oily water separator

The invention claimed is:

1. A method for converting ethanol, comprising:

contacting a raw material mixture containing ethylene and ethanol with a catalyst in an adiabatic reactor to obtain a reaction gas containing an olefin having 3 or more carbon atoms, wherein a catalyst bed outlet temperature is 450 °C to 590 °C, and wherein a temperature difference between a catalyst bed outlet temperature and a catalyst bed inlet temperature is -80 K to 80 K.

2. The method for converting ethanol according to claim 1, wherein a molar ratio of ethylene/ethanol in the raw material mixture is 0.20 to 2.5.

3. The method for converting ethanol according to claim 1, wherein a molar ratio of ethylene/ethanol in the raw material mixture is 0.20 to 2.0.

4. The method for converting ethanol according to claim 1, further comprising:

separating ethylene and propylene from the reaction gas.

5. The method for converting ethanol according to claim 1, wherein the raw material mixture contains an olefin having 4 to 6 carbon atoms.

6. The method for converting ethanol according to claim 5, wherein a molar ratio of olefin having 4 to 6 carbon atoms/ethylene in the raw material mixture is 3.0 or less.

7. The method for converting ethanol according to claim 1, further comprising:

separating the reaction gas into fraction A mainly containing a hydrocarbon having 1 to 3 carbon atoms and fraction B mainly containing a hydrocarbon having 4 to 8 carbon atoms; and separating ethylene and propylene from the fraction A.

8. The method for converting ethanol according to claim 7, further comprising:

recycling at least a portion of the fraction B to the reactor to use it as a portion of the raw material mixture.

9. The method for converting ethanol according to claim 1, wherein the reactor is a fixed-bed adiabatic reactor.

10. The method for converting ethanol according to claim 1, wherein a catalyst bed inlet temperature is 450 °C to 590 °C.

11. The method for converting ethanol according to claim 1, wherein the catalyst is a zeolite-containing catalyst.

12. The method for converting ethanol according to claim 11, wherein the zeolite-containing catalyst comprises medium pore-size zeolite.

13. The method for converting ethanol according to claim 11, wherein a molar ratio of silica/alumina of zeolite in the zeolite-containing catalyst is 20 to 2000.

14. The method for converting ethanol according to claim 11, wherein the zeolite-containing catalyst comprises a phosphorus element or a silver element.

15. A method for producing a hydrocarbon, comprising:

a cracking step of decomposing a hydrocarbon having 2 or more carbon atoms; and a refining step of refining a component obtained in the cracking step, wherein in the refining step, the reaction gas obtained by the method for converting ethanol according to claim 1 or a refined fraction thereof is combined with the component.

16. A method for producing an aromatic compound, comprising:

an aromatic compound-separating step of separating a fraction mainly containing an aromatic compound from the reaction gas obtained by the method for converting ethanol according to claim 1.

17. A method for converting ethanol, comprising:

contacting a raw material mixture containing ethanol and ethylene with a catalyst in an adiabatic reactor to obtain a reaction gas containing an olefin having 3 or more carbon atoms;

separating the reaction gas into fraction A mainly containing a hydrocarbon having 2 to 3 carbon atoms and fraction B mainly containing a hydrocarbon having 4 to 6 carbon atoms by a first distillation column; and recycling at least a portion of the fraction A as a portion of the raw material mixture to the reaction step.

18. The method for converting ethanol according to claim 17, wherein the recycling comprises recycling at least a portion of the fraction B to the contacting to use it as a portion of the raw material mixture.

19. An apparatus for converting ethanol, comprising:

a reactor which contacts a raw material mixture containing ethanol and ethylene with a catalyst in an adiabatic reactor to obtain a reaction gas containing an olefin having 3 or more carbon atoms; and a first distillation column which separates the reaction gas into fraction A mainly containing a hydrocarbon having 2 to 3 carbon atoms and fraction B mainly containing a hydrocarbon having 4 to 6 carbon atoms, wherein at least a portion of the fraction A is recycled to the reactor to be used as a portion of the raw material mixture.

* * * * *